US006407141B1

(12) United States Patent
Hart

(10) Patent No.: US 6,407,141 B1
(45) Date of Patent: *Jun. 18, 2002

(54) OXALIC ACID OR OXALATE COMPOSITIONS AND METHODS FOR VASCULAR DISORDERS, DISEASES, AND CALCEROUS CONDITIONS

(76) Inventor: Francis J. Hart, 390 Ryan Rd., Pea Ridge, AR (US) 72751

( * ) Notice: Subject to any disclaimer, the term of this patent is extended or adjusted under 35 U.S.C. 154(b) by 0 days.

This patent is subject to a terminal disclaimer.

(21) Appl. No.: 09/535,572

(22) Filed: Mar. 27, 2000

Related U.S. Application Data

(63) Continuation-in-part of application No. 09/014,943, filed on Jan. 28, 1998, now Pat. No. 6,133,318, and a continuation-in-part of application No. 08/629,538, filed on Apr. 9, 1996, now Pat. No. 6,133,317.
(60) Provisional application No. 60/036,983, filed on Jan. 29, 1997, and provisional application No. 60/006,785, filed on Nov. 15, 1995.

(51) Int. Cl.$^7$ ................... A61K 31/194; A61K 31/225
(52) U.S. Cl. ........................... 514/574; 514/547
(58) Field of Search ................. 514/574, 547

(56) References Cited

U.S. PATENT DOCUMENTS

| | | | |
|---|---|---|---|
| 3,542,573 A | 11/1970 | Biland et al. | 106/186 |
| 3,787,589 A | 1/1974 | Stephens et al. | 426/325 |
| 4,156,067 A | 5/1979 | Gould | 528/73 |
| 4,285,972 A | 8/1981 | Chou et al. | 424/326 |
| 4,340,609 A | 7/1982 | Chou | 424/322 |
| 4,760,157 A | 7/1988 | Child et al. | 556/137 |
| 4,900,746 A | 2/1990 | Hanson et al. | 514/400 |
| 5,137,722 A | 8/1992 | Costello | 424/195 |
| 5,151,274 A | 9/1992 | Saltman et al. | 424/630 |
| 5,175,144 A | 12/1992 | Walser | 514/2 |
| 5,183,674 A | 2/1993 | Olin | 426/2 |
| 5,227,248 A | 7/1993 | Wullschleger et al. | 426/549 |
| 5,245,095 A | 9/1993 | Graves et al. | 585/351 |
| 5,292,511 A | 3/1994 | Kim et al. | 424/195.1 |
| 5,292,773 A | 3/1994 | Hirsch et al. | 514/554 |
| 5,310,554 A | 5/1994 | Haigh | 424/439 |
| 5,314,686 A | 5/1994 | Todd, Jr. | 424/401 |
| 5,324,443 A | 6/1994 | Arif et al. | 252/142 |
| 5,330,972 A | 7/1994 | Cope | 514/2 |
| 5,346,707 A | 9/1994 | Olin | 426/69 |
| 5,376,361 A | 12/1994 | Perricone | 424/59 |
| 5,401,325 A | 3/1995 | Mihelic et al. | 134/39 |
| 5,401,326 A | 3/1995 | Mihelic et al. | 134/40 |
| 5,455,372 A | 10/1995 | Hirai et al. | 560/179 |
| 5,470,874 A | 11/1995 | Lerner | 514/474 |
| 6,133,317 A | * 10/2000 | Hart | 514/574 |
| 6,133,318 A | * 10/2000 | Hart | 514/574 |

OTHER PUBLICATIONS

Hodgkinson, A. Oxalic Acid in Biology and Medicine, Academic Press, 1977—pp. 1–3, 16–17, 18–21, 23, 37–38, 49–51, 69–80, 84–88, 100–103, 110–111, 122–124, 130, 133–135, 153–156, 159–164, 168–174, 180–182, 196–207, 216–228, 238.

Davis, Adelle, Lets Get Well, Penquin Group, 1972—pp. 195, 204–205, 213, 299.

Cowdry, E. Croninger, A. Solaric, S. Suntzeff, V. Cancer, Journal of the American Cancer Society, Combined Action of Cigarette Tar & Beta Radiation of Mice—1961, vol. 14—pp. 344–352.

Bock, F. Moore, G. Journal of the National Cancer Institute, Carcinogenic Activity of Cigarette Smoke Condensate. I. Effect of Trauma & Remote X–Irriation. vol. 22 No. 2—1959—pp. 401–411.

Svendsen, L. Rattan Surech I.S. Clark, Brian F.C. Journal of Ethnopharmacology—1994 Testing Gar for Possible Anti–Ageing Effects on Long–term Growth Characteristics, Morphology and Macro Molecu Synthesis of Human Fibroblasts in Culture—pp. 125–133.

Ney, D.M. The Low Oxalate Diet Book for the Prevention of the Oxalate Kidney Stones—pp. 944–945 & Appendix Table 13, University of California, San Diego 1981.

U.S. Department of Health & Human Services Public Health Service National Institutes of Health, NIH Publication, Eat More Fruits & Vegetables, Oct. 1991.

Chem One Corporation. Product Data Sheet, 1995.

Occupational Health Services. msds on oxalic acid, 1994.

(List continued on next page.)

Primary Examiner—Richard L. Raymond

(57) ABSTRACT

A single medicine oxalic acid or oxalate compositions, or "magic bullet" and methods of treatment and prevention of warm-blooded animals including humans and pets for vascular diseases, disorders, and calcerous conditions, chemoprevention of vascular diseases, disorders, and calcerous conditions, is provided which includes at least one therapeutically effective form of oxalic acid or oxalate selected from oxalic acid in a free acid, ester, lactone or salt form and oxalate including sodium oxalate, oxalic acid dihydrate, anhydrous oxalic acid, oxamide, and oxalate salts, natural or processed foods including molds, plants or vegetables containing oxalic acid or oxalate, beverages, liquids or juices containing oxalic acid or oxalate, additives containing oxalic acid or oxalate, and combinations thereof. The compositions may also contain a pharmaceutically acceptable carrier or diluent for the therapeutically effective form of oxalic acid or oxalate. Methods are provided including the steps of periodically administering, by topical, oral, or parenteral application, a therapeutically effective dosage of a composition including at least one therapeutically effective form of oxalic acid or oxalate in less than a lethal dosage and improving chemotherapy by reducing the intake of oxalic acid or oxalate blockers such as citric acid, ascorbic acid (vitamin C), pyridoxine hydrochloride (vitamin B6), calcium, alcohol, resins, clays, foods containing calcium, beverages containing alcohol, citric, or ascorbic acid, red meat or white meat of fowl containing pyridoxine hydrochloride, or other foods, nutritional supplements or beverages containing oxalic acid or oxalate blockers.

20 Claims, 1 Drawing Sheet

OTHER PUBLICATIONS

The Merck Manual, Diagnosis and Therapy, 1987 pp. 2465–2466, Oncology pp. 1206–1228.
NIH Specification 11–133 Open Formula Rat and Mouse Ration 9NIH)0–07) Nov. 1, 1986.
NIH Specification 11–137 Crude Protein Autoclavable (NIH–31) Nov., 1986.
Organic Gardening Articles, Rodale Press, Inc. Hurley, J.B. Calcium From the Garden Apr. 1986, pp. 96–98 Duke, L.A. Weeds? or Wonder Drugs? Jul. 1994 pp. 38–39 Duke, J.A. Eat Your Weedies Jul. 1993 pp. 31–35 Mattern, V. Don't Weed 'em, Eat 'em Apr. 1994 pp. 71–74.
Better Nutrition—Veggie Corner—Broccoli and Watercress Are Rich Cancer Fighters, Aug. 1994 p. 22 Editors Desk— Novel Cancer Therapies Deserve a Fair Hearing, Aug. 1994 p. 6.
Parade Magazine Special Intelligence Report, man Should Think Twice Before Eating Steak, Oct. 1994, p. 16.
Ferguson, K. VA Hospital Fayetteville, AR. Low Oxalate Diet, undated.
Journal National Cancer Institute, No. 85, Explanation For Link Between Alcohol and Breast–Cancer risk 1993, abstract.
Readers Digest, News from the World of Medicine. Device Spots Colon Cancer & Indoor Tanning? Don't Do It. Mar. 1994. Sunscreen: Slather It On, Do Fats Fuel Prostate Cancer? May 1994. Folic Acid, Superstar, Jun. 1994.
Letters, Natural Health. Beta–Carotene Debate Continues, Nov. 1994.
Microsoft Internet Explorer/NECX From Gopher:// gopher.nih. gov/00/clin/cdcs/67. kidney–Prevention and Treatment of Kidney Stones national Institute of Health Consensus Development Conference Statement, Mar. 1988 pp. 1–14.
Microsoft Internet Explorer/Open Text Index From:http:// www/mcs/net/–joyce/new,html Essiac Tea From Canada Comes A Remedy Called Essiac, Or Ojibwa Tea 1995, pp. 1–7 From: gopher://wiretap/spies/com/oo/1Library/Fringe/ Pharm/essiac.txt Essiac: a natural herbal alternative cancer treatment. Glum, G.L. Calling of An Angel, Apr. 1993 pp. 1–15. From:http://www/envirolink/org/arrs/VRG/calcium. html Mangels, R. Calcium in the Vegan Diet 1991 pp. 1–6. Weil, Andrew Natural Health, Natural Medicine. hOW nOT to gET cANCER, hOUGHTON mIFFLIN cOMPANY 1990 pp. 169–189.
Robbins, J. Diet for a New America. Losing A War We Could Prevent, Stillpoint Publishing 1987, pp. 248–273, 403–409.
Berkely, B. Nutritional Protocol for HIV, Project Inform San Francisco 1994.
NAU, Jean–Yves Preventing Spread of BSE, The Lancet Sep. 1994 vol. 344, p. 808.
Carper, Jean, Foods That Fight Cancer, Reader's Digest, Jan. 1994, pp. 119–122.
America's Parmaceutical Research Companies, Health Guide–Seventh in a Series, HIV/AIDS, 1997.
Solaray, Inc., CranActin . . . the one that gurantees bacterial antiadherence properties, 1996.
Houple, Molina, Reamer, Lynch, Volante, and Reider, Towards the Sythesis of HIV–Protease Inhibitors. Synthesis of Optically Pure 3–Carboxyl–decahydroisoquinolines,Tetrahedron Letter, vol. 34, No. 16, pp. 2593–2596, 1993.
Cabbages and Cancer, KEND, Feb. 3–5, 1995.
Perspective, The Antioxidant Nutrients, p. 320–324, The Regulatory Nutrients, 1995.
News from the World of Medicine, p. 147, Feb. 1995.
The latest findings: Help for Headaches, Family circle, Mar. 14, 1995, p. 53.
Health & Healing, Tomorrow's Medicine Today, Feb. 1994, vol. 5, No. 2.
Health & Healing, Tomorrow's Medicine Today, May 1995, vol. 5, No. 5.
Health & Healing, Tomorrow's Medicine Today, Mar. 1995, vol. 5, No. 3.
Health & Healing, Tomorrow's Medicine Today, Feb. 1995 Supplement.
Breakthroughs In Cancer Research, Nathaniel Mead, Natural Health, Jan., Feb. 1996.
More power to the people? AARP Bulletin, Mar. 1995, vol. 36, No. 3, Washington, D.C.
Cancer Treatment Choices, News from the World of Medicine, American Heart Association, p. 139, Feb. 1996.
Breast Cancer Update, News from the World of Medicine, American Heart Association, p. 108, Sep. 1995.
Cancer Update, News from the World of Medicine, American Heart Association, p. 113, Apr. 1995.
Early Alzheimer's Warning? News from the World of Medicine, American Heart Association, pp. 105–106, Jul. 1995.
Reversing Bone Loss, News from the World of Medicine, American Heart Association, pp. 99–100, Jul. 1995.
Garlic's Breath of Health, LEND, Mar. 31–Apr. 2, 1995.
Older Women: Cut the Fat, Not the Protein! Food & Health, Organic Gardening, p. 20, Feb. 1996.
Mood Foods, Food & Health, Organic Gardening, p. 22, Jan. 1996.
New Method Proposed to Determine Efficacy of Both Retinoids and Antioxidants in Preventing Cancer, Primary Care & Cancer, Jan. 1996, p. 32.
Cancer Facts & Figures—1995, American Cancer Society, Revised Jan. 1995.
On the Cancer Front, News from the World of Medicine, p. 127, Nov. 1995.
Merch Manual Home Edition—1997—pp. 121–126.
Merch Manual Diagnosis and Therapy 1987—pp. 477–499.
Commercial Mixture of Flavonoids, Provex Plus™, Sep. 1997.
Journal of Investigative Medicine, Sep. 1997, vol. 45, No. 7.
Commercial Mixture of Flavonoids, Provex CV™, Mar. 1998.
Journal of Investigative Medicine, Mar., 1998, vol. 46, No. 3.

* cited by examiner

OXALIC ACID OR OXALATE COMPOSITIONS AND METHODS FOR VASCULAR DISORDERS, DISEASES, AND CALCEROUS CONDITIONS

CROSS-REFERENCE TO RELATED APPLICATIONS

This Application is a Continuation-in-Part of U.S. application Ser. No. 09/014,943, filed Jan. 28, 1998, now U.S. Pat. No. 6,133,318, hereby incorporated by reference. Also this Application is a Continuation-in-Part of U.S. Provisional Application Serial No. 60/036,983, filed Jan. 29, 1997, hereby incorporated by reference. Also, this Application is a Continuation-in-Part of U.S. application Ser. No. 08/629,538, filed Apr. 9, 1996, now U.S. Pat. No. 6,133,317 which is a Continuation-in-Part of U.S. Provisional Application Serial No. 60/006,785, filed Nov. 15, 1995, hereby incorporated by reference.

BACKGROUND OF THE INVENTION

The present invention is directed to oxalic acid or oxalate compositions and methods of producing such compositions and for the utilization of oxalic acid or oxalate compositions, including solutions, mixtures, products, rinses, and carriers in the treatment, control, remedy, and prevention of vascular disorders, diseases, and calcerous conditions in patients.

Conventional medicine treats vascular disorders, diseases, and calcerous conditions with cholesterol lowering drugs, diet, and exercise programs, as well as life style changes such as quitting smoking. Coronary artery bypass surgery is preformed when conditions are not suited to artery angioplasty. Angiography is used to determine which invasive treatment may be feasible. There has recently been developed a new procedure involving the placement of stints in restricted arteries.

The cause of Alzheimer's disease is currently not known, and treatment is limited to drugs that may slow the progression of the disease.

In the case of vascular disease, artherosclerosis plaque develops in the arteries causing blockage. Plaque results when calcification takes place in the cholesterol developed gummy substances in the inner lining of the arteries.

Recent news articles reveal researchers suspect that formation of plaque in the brain interferes with normal activity.

In the early stages of research and development of the parent patent, U.S. application Ser. No. 08/629,538, filed Apr. 9, 1996, now U.S. Pat. No. 6,133,317, the inventor became aware of the decalcifying effect of oxalic acid on calcerous matter.

Oxalic acid or ethanedioic acid ($C_2H_2O_4$) is a dicarboxylic acid and is present in many plants and vegetables, notably in those of the Oxalis and Rumex families, where it often occurs in the cell sap of the plants as the potassium or calcium salt (oxalate, Tables I–IV). Oxalic acid is also a product of the metabolism of many molds. Several species of Penicillum and Aspergillus convert sugar into calcium oxalate with a 90 percent yield under optimum conditions. Oxalic acid is also made by passing carbon monoxide into concentrated NaOH or heating sodium formate in the presence of NaOH.

Oxalic acid dihydrate, monoclinic tablets, prisms, and granules are considered poisonous. Anhydrous oxalic acid is crystallized from glacial acetic acid and is orthorhombic with the crystals being pyramidal or elongated octahedral.

Oxalic acid is listed as being caustic and corrosive to the skin and mucous membranes. Ingestion may cause severe gastroenteritis, with vomiting, diarrhea, or melena. Renal damage can occur as a result of formation of excessive calcium oxalate crystals. Convulsions, coma, or death from cardiovascular collapse can also occur.

Conventional uses of oxalic acid include as an analytical reagent, in calico printing and dying, for bleaching straw and leather, removing paint or varnish, rust or ink stains, cleaning wood, and manufacturing oxalates, blue ink, celluloid, intermediates and dyes, in metal polishes, in purifying methanol, for decolorizing crude gycerol, for stabilizing hydrocyanic acid, as a general reducing agent, in ceramics and pigments, in metallurgy as a cleanser, in the paper industry, in photography, in process engraving, in rubber manufacturing, in making glucose from starch, as a condensing agent in organic chemistry, and a veterinary hemostatic agent when mixed in 5 percent solution with 5 percent malonic acid.

As described in "Oxalic Acid in Biology and Medicine" by A. Hodgkinson, 1977, oxalic acid was formerly used intravenously as a hemostatic agent and topically as an antiseptic in man and other animals but this was discontinued because of its toxicity and the danger of precipitating insoluble calcium oxalate in the tissues. Oxalic acid is a relatively strong acid having a first dissociation constant being exceeded by that of only a few halogen-substituted carboxylic acids. Oxalic acid forms neutral and acid salts with monovalent metals and ammonia. Oxalic acid forms a number of oxalates or salts including calcium oxalate, potassium oxalate, sodium oxalate, strontium oxalate, magnesium oxalate, and the like. Oxalic acid also inhibits the activity of a number of enzymes possibly due to the competition between oxalate and a structurally similar substrate of the enzyme. Precipitation as the calcium salt is the classical method of separating oxalic acid from other substances. Although calcium oxalate is generally considered to be an insoluble salt this is a relative term and its solubility in water is actually 6–7 mg/l at room temperature. Biological fluids contain many substances that affect the solubility or rate of crystallization of calcium oxalate or co-precipitate with the salt For example, magnesium, polyphosphates and other polyelectrolytes affect the solubility or rate of crystallization of calcium oxalate while phosphate and sulphate ions, uric acid and citric acid co-precipitate with the salt.

Further, as reported in a literature including "Oxalic Acid in Biology and Medicine", poisoning from oxalic acid in animals and man has been recognized since the beginning of the $19^{th}$ Century. The death rate from oxalate poisoning has declined supposedly because of a decreased use of oxalic acid in domestic cleaning fluids. Examples of chronic poisoning by absorption of oxalic acid through the skin and by inhalation have been reported. The range of lethal doses in acute poisoning is wide, varying between 2 and 30 g and depending upon a variety of factors such as the form in which the acid or its salt is taken and the amount of food, particularly calcium, which is present in the stomach and intestine. Death has occurred as early as 3 minutes and as late as 14 days after ingestion. Symptoms of acute oxalic acid toxicity in man can be divided into those caused by a local corrosive action and those resulting from absorption and excretion of the soluble oxalate. If a high concentration or the solid form is taken, the local effects may be predominant and death may result from acute hemorrhagic gastroenteritis without development of symptoms depending on absorption. If death does not result from local corrosive action then symptoms develop from the systemic effects and from renal insufficiency. The cardiovascular, neuromuscular and central nervous systems are markedly affected. The skin is pale, cold and clammy, the pulse is weak and the blood pressure and temperature are low. Numbness and tingling may develop in the extremities and cramp-like muscular and abdominal pain may be extremely severe. Local or generalized muscular twitching occur and may progress to marked tetany and convulsive seizures. The central nervous system may show evidence of excitation or depression, varying from an acute maniacal state to stupor and coma. Death results from cardiovascular collapse or depression of the central nervous system. Renal involvement is frequent and even if the patient survives the severe local or systemic effects, death may ultimately occur from renal insufficiency, which dominates the picture from the second day. Oliguria develops and may progress to anuria. Hence, there is a need for oxalic acid or oxalate compositions and methods of producing such compositions and for treating, preventing, impeding, retarding, delaying, and controlling vascular disorders, diseases, and calcerous conditions in patients.

BRIEF SUMMARY OF THE INVENTION

Figure 1:
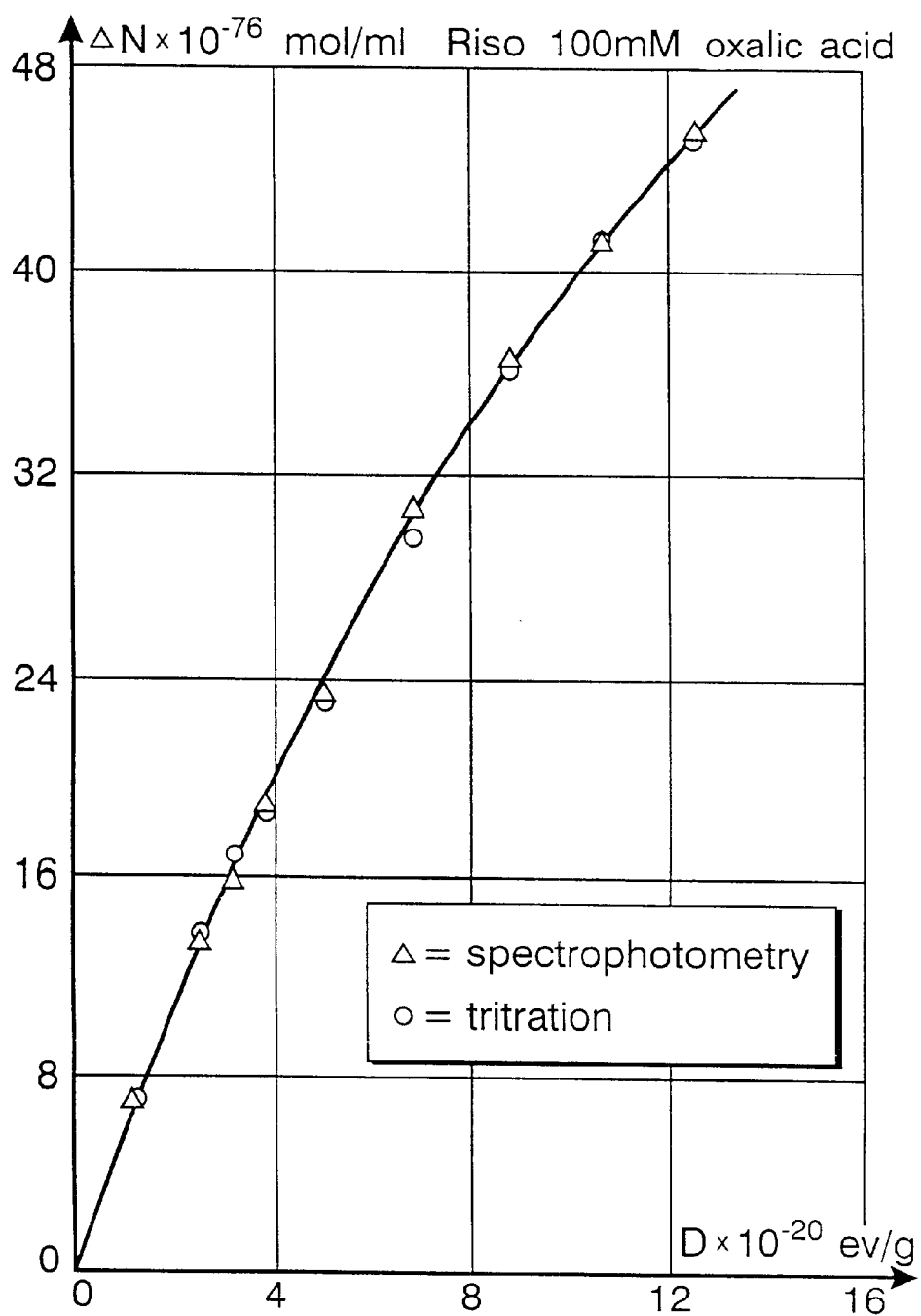
FIG. 1 is a graphical representation of the decomposition of oxalic acid.

In accordance with the present invention, oxalic acid or oxalate compositions and methods of producing such compositions and for treating, preventing, controlling, impeding, cardiovascular disorders, diseases, and calcerous conditions in warm-blooded animals is provided which includes an effective amount of at least one therapeutically effective form of oxalic acid or oxalate for controlling, treating, managing, preventing the diseases caused by other blood disorders, or for otherwise therapeutically treating patients including humans and pets.

The therapeutically effective form of oxalic acid or oxalate is an oxalic acid or oxalate which provides the beneficial effect and is selected, for example, from the group of oxalic acid in a free acid, ester, lactone or salt form, oxalate including sodium oxalate, a nutritional supplement containing at least one form of oxalic acid or oxalate, oxalic acid dihydrate, anhydrous oxalic acid, oxamide, oxalate salts, processed foods containing at least one form of oxalic acid or oxalate, beverages, liquids or juices containing at least one form of oxalic acid or oxalate additives containing one form of oxalic acid or oxalate, or combinations thereof, compositions including oxalic acid or oxalate, a therapeutic quantity of oxalic acid or oxalate composition, source of oxalic acid or oxalate, nutritional product, supplement, solution, agent, curative, remedy, control, impediment, food, feed stuff, rinse, mouthwash, mouth rinse, wash, formulation, dosage, pharmaceutical agent, dietary supplement, intermediate, product, composition, immune system stimulant, substance, drug, chemopreventive, chemical, chemosurgical agent, chemotherapy agent, chemotherapeutic agent, solution, solute, slurry, mixture, medicine, medication, analgesic, medicinal agent, treating agent, preventing agent, retarding agent, impeding agent, delaying agent, controlling agent, anabolic agent, health improving agent, health-supplementary food, enriched fraction, vascular disease treating agent, as ell as a supplemental composition or treatment to be used in conjunction with conventional compositions and treatments, and the composition may also contain a pharmaceutically acceptable carrier or diluent for the therapeutically effective form of oxalic acid or oxalate.

Also in accordance with the present invention a method is provided for controlling, treating, managing cardiovascular disorders in patients including the steps of administering an effective amount of a therapeutically effective form of oxalic add or oxalate. The method may include the further step of reducing the intake of oxalic acid or oxalate blockers such as citric acid, ascorbic acid (vitamin C), pyridoxine hydrochloride (vitamin B6), calcium, alcohol, resins, clays, and combinations thereof. Oxalic acid or oxalate blockers also include dairy products containing calcium, fruits, coconut, beverages containing alcohol, ascorbic acid or citric acid, red meat or white meat of fowl containing pyridoxine hydrochloride, or other foods, nutritional supplements or beverages containing alcohol, citric acid, ascorbic acid, pyridoxine hydrochloride, resins, and combinations thereof.

In accordance with the present invention, an oxalic add or oxalate blocker is any mineral, chemical, compound, material, plant, food, beverage, additive, supplement, or the like which blocks, inhibits, reduces, or binds with or otherwise reduces or eliminates the beneficial effect of oxalic acid or oxalate. For example, calcium from dairy products tends to bind with oxalic acid in the intestine (calcium oxalate) and prevents the oxalic acid from being absorbed into the blood stream.

In accordance with yet another embodiment of the present invention, a diet is provided for treating, controlling, preventing, impeding, cardiosclerosis in patients. The diet includes adding to the regular diet a dietary supplement of at least one therapeutically effective form of oxalic acid or oxalate. Further the diet may include reducing the intake of oxalic acid or oxalate blockers.

In accordance with another embodiment of the invention a composition and method for treating fatty substance and plaque related to dementia conditions of a patient.

In accordance with still another embodiment of the present invention, a veterinary composition includes conventional pet food ingredients except for the elimination or reduction of oxalic acid or oxalate blockers and the addition of a therapeutically effective quantity of at least one therapeutically effective form of oxalic acid or oxalate.

In accordance with yet another embodiment of the present invention, an oral rinse, pill, gel cap, tablet, powder, or capsule for controlling, treating or managing cardiovascular disorders and diseases is provided which includes a dilute concentration or solution of at least one therapeutically effective form of oxalate.

In accordance with yet another embodiment of the present invention, a pharmaceutical composition to be administered orally to patients is provided which includes a mixture of a nontoxic ingestible carrier and a therapeutically effective form of oxalic acid or oxalate in less than a lethal dosage.

In yet another embodiment of the present invention, a therapeutic composition in lozenge or cough drop form for oral administration of oxalic acid or oxalate is provided which includes at least one therapeutically form of oxalic acid or oxalate and an ingestible carrier of dextrose, microcrystalline cellulose, povidone, magnesium stearate, and the like.

In accordance with another embodiment of the present invention, a pharmaceutical composition to be administered orally to patients is provided which includes a mixture of nontoxic ingestible carrier such as sorbitol, fructose, sucrose, lactose or distilled water and a therapeutically effective form of oxalic acid or oxalate in less than a lethal dosage.

One object of the present invention is the provision of a novel therapeutic composition including a pharmaceutically acceptable carrier or diluent containing a therapeutically effective amount of at least one therapeutically effective form of oxalic acid or oxalate. Another object of the present invention is the provision of a method of therapeutically treating patients with such a therapeutic composition.

A further object of the present invention is the provision of an oxalic acid or oxalate pharmaceutical composition, a therapeutic quantity of oxalic acid or oxalate composition, source of oxalic acid or oxalate, nutritional product, supplement, solution, agent, curative, control, remedy, impediment, food, feed stuff, rinse, mouthwash, mouth rinse, formulation, dosage, pharmaceutical agent, dietary supplement, intermediate, product, composition, immune system stimulant, substance, drug, chemopreventative, chemical, chemosurgical agent, chemotherapy agent, chemotherapeutic agent, solution, solute, slurry, mixture, medicine, medication, analgesic, medicinal agent, treating agent, preventing agent, retarding agent, impeding agent, delaying agent, controlling agent, anabolic agent, health improving agent, health-supplementary food, enriched fraction, as well as a supplemental composition or treatment to be used in conjunction with conventional compositions and treatment.

Another object of the present invention is the provision of a method of treating patients with at least one form of oxalic acid or oxalate.

Yet another object of the present invention is the provision of a pharmaceutical composition to be administered orally to patients including a mixture of a non-toxic ingestible carrier and a therapeutically effective form of oxalic acid or oxalate in less than a lethal dosage.

A further object of the present invention is the provision of a multi-vitamin or multi-vitamin and mineral supplement including at least one therapeutically effective form of oxalic acid or oxalate.

Still another object of the present invention is the provision of a processed food item including a therapeutically effective amount of at least one therapeutically effective form of oxalic acid or oxalate.

Other objects and further scope of the applicability of the present invention will become apparent from the detailed description to follow.

DETAILED DESCRIPTION OF THE INVENTION

The story begins with two toy poodles, Turk and Taka. These animals lived a normal house life. Except for the occasional trip or walk to the nearby reservoir, their territory was the house and backyard. As young pups they were full of energy and, of course, very spoiled. Habits, mostly bad ones, were easily formed. such as eating people food, some of which, according to a veterinarian, would not hurt them. Turk became fond of SNICKERS® brand candy bars, especially the small bite-size kind, and also carrots and beets, both of which are appearing in some commercial dog foods today.

During this time, Turk's owner, the present applicant and inventor, was doing a great deal of traveling, averaging one trip a week, and he always kept a small SNICKERS® bar near the front door in case he returned home without one. Another one of Turk's favorite treats was the small soybean crackers in oriental cocktail mix, which Turk's owner ate constantly when he was home.

When Turk was about a year and six or seven months old, Turk began to slow down. Turk's eagerness to play left him, and his appetite diminished except for the little treats mentioned above. Turk was drinking much more water and had frequent accidents in the house, especially at night. Turk's color changed from a parfait tinge to a solid white, and just before his death, to a dull grayish-white.

When Turk began to vomit occasionally after eating or drinking, Turk's owner became concerned and took Turk to the veterinarian. The examination revealed nothing, and the veterinarian diagnosed Turk as having indigestion and gave Turk some medicine. Turk's condition worsened, and so Turk was returned to the veterinarian. Blood and urine samples were taken, and test results revealed that Turk's urine was watery, but otherwise all right. The blood however, showed a high white cell count, and the veterinarian thought there might be an infection and prescribed pills. One single pill brought on violent vomiting. Turk's owner stopped giving Turk the pills and started Turk on amoxicillin.

Turk's condition worsened, so Turk was taken to the animal hospital center where they determined Turk's kidneys were failing. Turk was put on an IV due to severe dehydration. The doctors stated that they could not treat Turk unless Turk's owner could tell them what poison or chemical Turk had ingested. For the next several days Turk's owner went on a frantic search for answers. Turk's owner contacted a number of agencies for possible clues to the poisoning: Tri-County Health Department; two toxicologists with the EPA; the U.S. Corps of Engineers, who assured him that they test the reservoir daily for contaminants; and UCLA and University of Illinois poison centers. Heavy rains would bring standing water into the backyard, so Turk's owner tracked down the owners of a stable and a nursery that used to operate in the area before the houses were built, to see if they had used any type of toxic sprays. Turk's owner contacted nurseries from which he had recently bought plants. Turk's owner even contacted the 3M Company, since new carpeting with SCOTCHGARD® had been installed. Turk's owner asked all neighbors who had pets to find out if their pets had become sick.

Turk's owner also called veterinary clinics to find out if they had diagnosed similar cases recently. He also searched every square foot of the house, garage, and storage building looking for chemicals, especially antifreeze. Out of desperation, Turk's owner pleaded with the veterinarians to list poisons that had the same fingerprint, and he would then choose one so veterinarians could begin treatment. The veterinarians declined. When blood began to appear in Turk's stool and vomit, and the kidneys had shut down, Turk was put to sleep. Turk's owner vowed that with God's help he would find out what had destroyed Turk.

The attending veterinarian at the veterinary hospital was an organ specialist and professor at Colorado State University. The veterinarian extended his sympathy and after a few other exchanges he informed Turk's owner that there is one substance very damaging to renal tissue—oxalates. The owner drove directly to his company's quality control department lab where he cornered a chemist and questioned him about oxalates. The chemist said that an oxalate is a compound found in trees, mainly oaks. The owner's curiosity was running high, and as soon as he could break away from work, he went straight for a dictionary. Oxalate is defined as a salt or ester of oxalic acid, and the acid definition refers back to the oak tree. Oxalic acid is further defined as an industrial chemical used in textile and dye manufacturing as a bleaching agent. From the dictionary, he went to the chemical books, found oxalic acid and got promptly lost in a maze of formulae and equations. The owner eliminated oxalates or oxalic acid from his mind as a cause of Turk's death. What did stay in his mind was Turk's death, and again he renewed his vow to find the answer. He could not get Turk out of his thoughts, because every time he looked at Taka, Turk's brother, he wondered why Turk had died and not Taka?

One outside activity of Turk's owner was, and still is, gardening. Naturally, he had a subscription for the organic gardening magazine, and perused through every article. In the April 1986 edition he came across an article by Judith Benn Hurley, "Calcium From Your Garden," and up popped the word oxalate. Imagine his surprise, an industrial chemical, a poison, in a magazine on organic gardening.

Once again the search was on. The owner wrote a letter to Ms. Hurley describing his research, the reason for it, and asked if she had anymore information on oxalates she could share. The reply he received provided him with more information than he could have hoped for. Her reply sent him to the library, to the section containing books on nutrition. He read many volumes and was amazed by the amount of information available on plant life and the effects of plant vitamins on maintaining human life. His effort was rewarded when he found a volume *Let's Get Well* by Adelle Davis, 1965. It contains the perfect finger print of Turk's death. Chapter 19, page 239 states the following:

When both vitamin B6 and magnesium are undersupplied, the kidneys are further damaged by sharp crystals of oxalic acid combined with calcium, and as much as three-quarters of the kidney may be replaced by scar tissue. Children with oxalic acid kidney stones frequently have high blood pressure and kidneys so damaged that they become progressively worse, causing death from kidney failure early in life.

The owner's mind went back to information he had gathered concerning the use of beagles in testing because their organs are more like those of a child than any other animal. How true the statements, "love them to death" and also "kill them with kindness." The owner believed that he had inadvertently killed Turk by feeding him candy bars, soybean crackers, beets, carrots, and who-knows-what-else that might have been very high in oxalate, oxalic acid or both. He believed that these snacks saturated Turk's system to a point where Turk's kidneys could no longer function. When that happened, the acid began to destroy renal tissue. As the tissue was being destroyed, Turk's condition worsened until other vital functions were affected. Turk's owner also believed that since oxalates and oxalic acid suppress calcium, no healthy red blood cells were being produced. The blood in Turk's system had to have been totally saturated with oxalic acid. When all the renal tissue was destroyed, the kidneys shut down and swelling began due to edema. There was no hope for recovery.

Taka was not affected because he did not crave or eat soybean crackers, beets or carrots, nor the SNICKERS® brand candy bars with peanuts. When the owner realized what caused Turk's death, he put Taka on an oxalate/oxalic acid-free diet. Some weeks after putting Taka on the diet, the color of Taka's coat, which had faded, began returning to normal. Knowing that a human could suffer from an excess of oxalates and oxalic acid, the owner put himself on a similar diet as well.

Several significant events occurred beginning with the return of the color of Taka's coat while on the oxalate-free diet. The owner began to watch for signs in his own hair and noticed that his graying seemed to have at least slowed down. Since the owner was due for a physical, he checked into a clinic and stated he had some minor pain in his chest on the left side where he had muscles torn in a car accident many years earlier. During the exam, the doctor decided to be safe and ordered an EKG. In prepping for the EKG, the nurse shaved his chest where the transducer cups would be placed, and then with a small orbital sander removed some of the dead skin for better contact. Weeks after the exam when the hair began growing out, it was black instead of gray or white.

Many mornings before starting the oxalate-free diet, the owner would get out of bed with a dull backache, and occasionally it would really spasm when he would lean over the wash basin while brushing his teeth. He complained and swore he would get a new mattress, believing it to be the cause of the backaches. By the end of the day the ache would be gone and out of mind. When the backaches stopped, he realized it was his kidneys and knew it was the soybean crackers and nuts in the oriental mix and other related items that had raised his oxalate level to the point it began bothering his kidneys.

After retirement, Turk's owner was planning to move and some friends stopped by to visit. One evening while having cocktails with the friends, they began talking about health and age, etc. One of the ladies mentioned she needed bypass surgery, but it could not be scheduled because her red blood cell count was low, and the doctors could not get it to rise, even though she was on a third medication. Turk's owner's research had paid off. He gave his organic gardening magazine to the lady and urged her to read the article by Judith Benn Hurley. He explained to her that the reason her red cell count was low was because of her diet. She ate very little meat, a primary source of pyridoxine (vitamin B6), did not drink much soda pop, orange or pineapple juice (all high in citric acid), and only consumed alcohol in moderate quantities. Her diet contained items high in oxalic acid, like spinach, her favorite salad. The owner mentioned that in his research he had discovered there were three chemicals that would counteract the oxalic acid—pyridoxine hydrochloride (vitamin B6), citric acid, and alcohol. He gave her a handful of 50 mg vitamin B6 pills and suggested she take one immediately and then one a day for the first week, and then one every other day. Three weeks later she told him that the doctor had just scheduled her operation.

Turk's owner had also noticed that he did not have the recurring attacks of heartburn he had prior to changing his diet and taking vitamin B6. He thought it a great discovery.

Then Turk's owner moved to Arkansas. His stepdaughter, who is married and living nearby, worked at a local hospital. One day she began running a high fever in the range of 104°–106°, went home, and went straight to bed. The fever fell, and the next couple of days she returned to work only to have the fever return after a couple of hours. She went home and the cycle repeated. She mentioned this to a doctor in the emergency room and a series of tests were ordered looking for a virus, an infection, even a tubular conception. Turk's owner became involved, because after listening to long, sometimes whispered conversations between his wife and stepdaughter, he asked what the trouble was. His wife explained what had happened and that the doctor was looking for some type of urinary tract or vaginal infection, but there were no positive cultures. When he heard that the stepdaughter experienced burning and irritation when urinating, he asked his wife why they did not think about diet. His stepdaughter was eating primarily salad bar meals loaded with oxalic acid. He had his wife immediately take a bottle of vitamin B6 pills to his stepdaughter with a suggestion to take two pills immediately, another one after twelve hours, and one a day after that for the next week. In two days her fever was gone, and she went back to work. After the third day all symptoms were gone and she was back to normal as best they could ascertain. Other people who complained of back pain without having muscle or spine problems found relief after Turk's owner suggested taking vitamin B6.

One day while drying off after a shower, Turk's owner noticed a mole-type growth on the inside of his right thigh. He had not noticed it before, and shortly after that, a growth began at the end of his right eyebrow near the bridge of his nose. As the growth on the thigh became bigger, so did his curiosity. He picked at the growth until some of it came off and it bled. Now curiosity turned to concern. A month later the growth on the thigh reappeared and the growth on the eyebrow grew larger. He would check both growths every day and they were always on his mind. He believes it was his obsession with Turk that guided his thoughts to oxalic acid. This acid is readily available in foods people eat, so why would God put a substance in food He provided to sustain life, if that same substance by assaulting the kidneys can kill life? It just did not make sense. That question constantly ran through his mind begging to be answered. Night after night, hours were spent turning and tossing in restless sleep, searching and searching for an answer. He had read every article in every magazine he could get his hands on about foods thought to help in the fight against cancer, antioxidants, free radicals, and anti-rust in the blood. One night his mind stopped on one particular item. It was a sentence he had read about foods, and the importance they play in health and healing. "The acid in strawberries is thought to help prevent prostate cancer." Acid—there it was, that is the word that halted his mental computer. When he woke up, questions began running through his mind. If oxalic acid would destroy healthy renal tissue, could it possibly destroy sick tissue first? Is cancer not considered to be sick cells? Are these free radicals sick cells? What about antioxidants? Are there really different types of cancer, or are they a similar type of sick cell just in different parts of the body? Why are there different types of chemotherapies?

There were just too many questions. He had to go back and start with his initial question. He asked a dear friend, a devout Christian, whether the Bible states that God put everything on earth that man needs? At the same time he went on a very high oxalic acid diet and avoided citric acid and reduced his intake of pyridoxines and alcohol to a minimum. His dear friend came back and said she told her Bible class of his request. They searched the Bible and noted three places that mention God providing for all of man's needs. What is significant is that articles describing food groups for cancer prevention, especially the vegetable groups, name those that have significant amounts of oxalic acid as per USDA Bulletin #11 (Table I). At this time he became convinced it was not the beta carotene, the vitamin C, or anything else that was the cancer fighter—it was oxalic acid. Once again he started asking himself questions. Would oxalic acid destroy sick cells before healthy cells?

The only answer he could come up with is the affirmative.

The story continues with the submittal of U.S. provisional application Serial No. 60/006,785, filed Nov. 15, 1995, U.S. patent application Ser. No. 08/629,538, filed Apr. 9, 1996, now U.S. Pat. No. 6,133,317 and U.S. provisional application Ser. No. 60/036,983, filed Jan. 29, 1997, entitled OXALIC ACID OR OXALATE COMPOSITIONS AND METHODS OF TREATMENT FOR BACTERIAL DISEASES AND VIRAL DISEASES IN HUMANS AND ANIMALS, by Francis J. Hart, all three applications being hereby incorporated by reference.

After placing himself on a high oxalic acid or oxalate diet, the growth on Turk's owner's thigh began to disappear and shortly thereafter the growth on his eyebrow as well. Eventually both growths were completely gone. Another sign of the result of the high oxalic acid diet was the disappearance of a couple of polyps around the anal orifice. These had appeared when he went on the low oxalate/low oxalic acid diet, and now when he reversed the diet these growths disappeared.

Later, his own daughter informed him that her mother was having a lot of stomach or digestive problems and was due for exploratory surgery. During the operation they discovered cancer in the abdominal cavity and removed all possible, estimated at 80 percent. There was cancer in the bladder, and they planned an extensive chemotherapy program. However, a specialty lab in California which received the tissue sample, determined it was a rare type of cancer, with no known treatment. His daughter, who was at her mother's side constantly, agreed to try his oxalic acid procedure. With his suggestion and the help of a juicer, she prepared a mixture of carrots, spinach, parsley, and chives. He suggested she try to get her mother to drink six to eight ounces of the mixture at least three times a day. At the start, her mother complained of the taste, so he suggested she mix some V8® juice with the mixture to enhance the flavor. This worked, and her mother began to drink the mixture. He felt that by having it in liquid form, more oxalic acid would enter her system more rapidly and begin to attack the sick cells. On the third day after her mother began drinking the mixture, his daughter talked with the nurse who said, "In the morning when she took the patient's vital signs they were the best since the patient had come to the hospital. Her temperature was down, blood pressure was down, and pulse rate was near normal." In addition, the yellowish skin color began to change. Then, for reasons unknown, her mother stopped drinking the mixture. Shortly after that her mother passed away.

Later, Turk's owner learned of a close friend who had prostate cancer, initially treated with a radiation implant which failed to keep the growth in check, and now would be undergoing chemotherapy. He urged his friend with prostate cancer to try his oxalic acid dietary treatment. He sent an explanatory letter with copies of articles about the vegetables along with a list of items containing oxalates and oxalic acid. Later, he talked with his friend who gave him some revealing data. Prior to starting the oxalic acid dietary treatment, his friend had been to an oncologist because the cancer was spreading into the pelvic area and his PSA count was 350. When his friend returned to his primary care physician months later after being on the oxalic acid diet, he was feeling better, his PSA was down to 246, and the doctor was surprised because he did not think his patient would survive long enough to see him again. It seemed the doctor knew the chemotherapy would not work and it may have been given just so his friend would not despair. Turk's owner sent a copy of the Judith Been Hurley article to his friend and believed that low calcium in the bone marrow was probably the reason his friend with prostate cancer was tired and felt pain in the thigh and pelvic area.

Turk's owner, the Applicant, further investigated to try to better establish the relationship between oxalic acid and pyridoxine hydrochloride (vitamin B6) and oxalic acid treatment for the reduction of tumors. An Irish Setter, a 70–75 lb., 14 year-old specimen, had a very noticeable tumor on the mouth, had been diagnosed with multiple tumors which a biopsy confirmed to be melanoma (skin cancer), and was to be euthanized. The oral tumor was in an area easily examined. The oral tumor had been removed several years ago, when it was confirmed as malignant, but it had grown back. The question was posed if a high oxalic acid or oxalate diet supposedly works on humans, would it not also work on this dog? They felt confident, since The Merck Manual does state that 90 percent of cancers are due to environment and nutrition. And so, they embarked on taking the Setter off canned dog food (high in pyridoxines) and feeding a regular dry high protein dog food mixed with three or four boiled carrots and topped with chopped parsley. The canine was started on a diet of three or four medium sized boiled carrots, mixed with approximately 1½ pounds of dry dog food. Three to five days after starting on the diet, the canine showed an improvement in appetite and energy. After three weeks of being on this diet, there was a noticeable reduction in size and appearance of the tumor on the canine's mouth. Almost a month after starting on the above diet, the canine's diet was changed to a mixture of about one pound of boiled carrots, one teaspoon of garlic, one-quarter cup chopped fresh parsley, and one and one-half pounds of dry dog food containing no citric acid. This diet was varied based on the canine's condition with the mouth tumor being measured and recorded by a veterinarian. The mouth tumor exhibited expansion or swelling and reduction cycles. The canine's urine was tested for oxalate count and a result showed about 50 mg per liter of oxalic acid.

After about five months on this diet, the canine produced feces including mucous and intestinal membrane. Upon this happening all oxalic acid or oxalate addition to the canine's diet was stopped. It is believed that a high level of oxalic acid or oxalate intake causes a sloughing off of the interior surface of the small intestine including old bacteria, food, waste, and intestinal cells and membrane. After about a month, urine was drawn from the canine to test for oxalate count the canine's oxalic acid urine count was reduced to 24 mg/L. Three days later, the canine was restarted on a diet having about 1 gram of oxalic acid added to one pound of dry dog food. A canine urine oxalic acid scale was calculated based on a scale of 0–40 mg/L for a 70 kg human, and adjusting this for a 25 kg canine to have a desired range of about 0–14 mg/L. The canine was started on a new diet of approximately one and one-half pounds of dry dog food to 1 gram of oxalic acid dihydrate dissolved in about three ounces of water and mixed together and adding one-half can of Pedigree° brand canned dog food (6½ oz. can) to add protein to the diet. A little more than two weeks later the diet was changed to reduce the oxalic acid dose to 500 mg per day and the canine was given four beef strips (approximately 25 grams) with 27 percent protein each evening. Thirty days later the dose was dropped to 300 mg oxalic acid/day. Two weeks later the dose was dropped to 50 mg oxalic acid/day. Two weeks later the dose was dropped to 20 mg oxalic acid per day which was maintained till the animal was euthanized. The canine's mouth tumor had reduced in size in an eleven month period. The oxalic acid dihydrate was purchased from Swift Chemical Company, Rogers, Ark., and dissolved in water to use as a food additive to the canine diet.

Much to their surprise, the dog seemed to crave the carrots and parsley. The Setter's activity increased steadily to the point where he actively competed with a four-year old Doberman and a nine-month old Rottweiler. The diet was working. What was once a large saggy sack of black tissue visibly hanging from the Setter's mouth changed to a considerably smaller and firmer growth. The reduction in the growth of the oral tumor slowed over time; however, it must be remembered that the tumor took nearly six years to achieve the mass it once was. They continued to monitor the Setter's condition, and felt that the reduction in the size of the tumor was a positive sign that the oxalic acid or oxalate was working. An autopsy of the Irish Setter revealed the malignant melanoma with metastasis, adrenal gland pheochromocytoma, acute cystitis, the urinary bladder mucosa appeared diffusely thickened, granular and hemorrhagic in appearance with the presence of moderate amounts of a turbid reddish-brown urine, a large encapsulated necrotic mass within the omental adipose tissue, with no other significant gross lesions noted within other areas of the oral cavity, larynx, esophagus, trachea, lungs, heart, spleen, kidneys, musculoskeletal system, and gastrointestinal tract. Hence, it appears that the oxalic acid or oxalate diet did not damage any of the dog's organs or kidneys. It is believed that the lesions (scars) in the lungs of the canine, may indicate that oxalic acid or oxalate had eliminated growths in the lungs.

In accordance with another case study, a dog at a pound was given one gram of oxalic acid dihydrate in a gel cap one hour prior to meal time for seven days with no adverse effects. The dog's appetite increased as well as energy and activity.

In accordance with another case study a human adult female subject with possible cervical cancer found multiple growths on her cervix by self-examination. The subject started on an increased oxalic acid or oxalate and reduced oxalic acid or oxalate blocker diet, and in less than one month she reported that the smallest growth was reducing in size. The subject remained very strictly on the diet and a week later reported that the smallest growth was gone with only a rough spot remaining. A few days later the subject reported that the next size growth seemed to be reducing. Less than a month later, the subject reported that the large growth was considerably reduced. This process continued and less than a year after starting on the increased oxalic acid or oxalate diet, the subject reported that one small growth remained which was only noticeable during her menstrual period.

In accordance with another case study, an adult male human subject suffering from a brain tumor, had been through all the different conventional treatments including surgery chemotherapy, and radiation treatment. The tumor was never totally removed and remained malignant. The subject was told of the possible beneficial effects of oxalic acid or oxalate and began on a treatment regimen of four heaping soup spoons of dried parsley daily and a reduction of oxalic acid or oxalate blockers. This should equate to approximately four grams of oxalic acid per day. Three to four months later, the subject had a CAT scan where the tumor was examined and did not show any growth. The subject also had visible signs of noticeable improvement in health. Approximately six months after starting on the enhanced oxalic acid or oxalate diet, the subject was much more active and friendly towards others. Approximately eight months after starting on the enhanced oxalic acid diet the subject was very excited about the diet, feeling much better. The subject had expected and experienced the toxic effects of indigestion, diarrhea, and the sloughing off of the interior surface of the intestine. The subject also indicated that the tumor was in the inactive stage. Also the subject indicated that his memory and thinking capability had returned and he could now accomplish functions he could not prior to following the diet. He was in the process of rebuilding an engine, replacing a carburetor, changing an oil pan. changing the oil and spark plugs, and other activities that prior to starting on the enhanced oxalic acid or oxalate diet were impossible.

Doctors had not given this patient much time to live, and it is believed that the enhanced oxalic acid or oxalate diet with reduced blockers had treated, controlled, or otherwise beneficially affected his brain tumor and overall health. He was still alive and functioning better after nine months.

An adult female in her sixties was terminally ill with leukemia with tumors in her lymph nodes and she had stopped chemotherapy treatment. She was told about the possible beneficial effect of oxalic acid or oxalate and started on a daily intake of about 1 to 1 ½ g/day oxalic acid or oxalate and almost no oxalic acid or oxalate blockers. It was hard for her to swallow so she was on a liquid diet because of the swelling of the lymph nodes in and around her mouth and throat. After 5–7 days of administration of oxalic acid or oxalate in dilute solution she was able to eat again due to the shrinkage of tumors in the lymph nodes. This dramatic effect in such a short time indicates that the intake of oxalic acid was treating her condition or disease and benefiting the individual.

In another case study, an adult female was diagnosed with a tumor (endometrial) in the uterus. The tumor was removed by laser and she was to undergo chemotherapy. She heard of the oxalic acid treatment of the present invention, and went on the diet having increased intake of oxalic acid or oxalate and reduced intake of oxalic acid or oxalate blockers. After several months of being on the diet, her blood tests were negative on cancer and she did not have to undergo conventional oncological chemotherapy.

In accordance with another case study, a Doberman pincher was diagnosed with bone cancer (sarcoma) of the left hind leg. The dog had previously been put on medication for arthritis because it would not use or lower its left hind leg. After being diagnosed with cancer confirmed with X-ray, the dog was placed on a diet of oxalic acid enhanced dogfood containing about 2 grams of oxalic acid dihydrate dissolved in water and added to conventional dry dogfood. Within 4 days, the dog had lowered its left hind leg and used it frequently in activity with a companion dog. A few days later, the dog began taking steps on the left hind leg with a slight limp. The dog's condition continued to improve and it's diet was changed to reduce the oxalic acid to about 1 gram of oxalic acid/per day. After a couple of weeks the dog's condition continued to improve so the dosage of oxalic acid was reduced to about 500 mg/per day. The dog appears to be walking with no pain and an X-ray revealed an increase in bone material in the area of the sarcoma and a decrease or reduction in the size of the area affected by the sarcoma. After being on the oxalic acid diet for about 30 days, the dog appeared to have no pain during physical exam and was walking normally.

In another case study, an adult female was diagnosed with stomach cancer and scheduled for surgery. She began the increased oxalic acid or oxalate and reduced oxalic acid or oxalate blocker diet and when she went in to have the surgery done, they discovered that her tumor had turned to liquid. Her diet or treatment regimen included a low intake of red meat or white meat of fowl, a low intake of soda pop or other beverages containing citric acid, a low intake of foods containing citric acid, an intake of about 4 ounces of carrot juice per day with 2 ounces taken in the morning and 2 ounces in the evening, and a low intake of alcohol. Apparently, the oxalic acid in the carrot juice may have turned the tumor cells into a liquid and all that was necessary was for the liquid to be drained.

In another case study, an adult female having breast cancer started on a high oxalic acid or oxalate and low oxalic acid or oxalate blocker diet. The growth of the cancer was reduced and in less than 2 months of being on the diet her blood work showed a large reduction in the cancer in the blood and that the cancer was in regression. Her condition improved so much so that the doctors stopped conventional chemotherapy treatment.

In another case study, an adult female with breast cancer went on a diet including an intake of about 4 ounces of carrot juice per day along with chicken broth. In about S weeks she was sent home from the hospital. she was walking, went to the mall and was eating potato chips. Previously, she had been hospitalized and on a liquid diet.

In accordance with another case study, an adult female suffering from breast cancer went on an increased oxalic acid diet, stopped using the microwave oven to cook foods, stopped chemotherapy treatments, cut CAT-scans down to once a month, and in a short time her blood was tested and showed that it was clean of cancer cells and the breast cancer appeared to have stopped growing.

Based on this history, it is believed that oxalic acid or oxalate will, at a minimum. reduce the size of tumors; especially if pyridoxine hydrochloride, citric acid, ascorbic acid. calcium and alcohol are eliminated from the diet as much as possible. This dietary procedure needs to be continued until the tumor or growth is eliminated. If the individual experiences backaches due to kidney irritation, urinary tract irritations, and/or severe heartburn, vitamin B6 (pyridoxine hydrochloride) can be taken to help eliminate the discomfort. Since calcium, pyridoxine hydrochloride, citric acid, ascorbic acid and alcohol block oxalic acid or oxalate, the individual should work his/her dietary therapy up to the point of experiencing the discomforts stated and then back off slightly from oxalic acid or oxalate intake. It is also believed that the converse is also true—insufficient oxalic acid or oxalate may allow tumors to grow.

Since certain cancers in animals are believed to be caused by viruses, it was postulated by the present inventor. that oxalic acid or oxalate may be useful in treating infectious or pathogenic bacterial, viral. or other microbial diseases in addition to treating cancers, tumors, neoplasms, and the like.

This invention relates generally to methods and compositions containing oxalic acid or oxalate or related compounds for providing therapeutic effects such as the control. prevention, or treatment of cancer, tumors, neoplasia, infectious or pathogenic bacterial, viral, or other microbial diseases, etc. It was initially discovered that a lack of oxalic acid or oxalate in the diet of a human, allowed or promoted the growth of tumors, growths, or other neoplasia. It was then discovered that the ingestion or administration of a therapeutic quantity of oxalic acid, oxalate or foods containing high levels of oxalic acid or oxalate can deter, reduce, or prevent the growth or spread of cancer, tumors, or other neoplasia. Then, it was discovered that an oxalic acid solution controlled, prevented, or treated infectious or pathogenic bacterial or viral diseases such as colds, flu, sore throat, and the like.

It has also been discovered that the therapeutic effect of oxalic acid or oxalate can be inhibited by an increased ingestion or administration of oxalic acid or oxalate blockers including, for example, calcium, alcohol, citric acid, ascorbic acid (vitamin C), pyridoxine hydrochloride (vitamin B6), etc. Other oxalic acid or oxalate blockers include binding agents such as clay, resins, and indigestible fibers. Radiation, strong electromagnetic waves or fields, electron bombardment, excessive heat, and bases such as sodium bicarbonate serve to decompose, neutralize or otherwise reduce the beneficial effect of oxalic acid. There may also be pharmaceuticals which interfere with the absorption or beneficial activity of oxalic acid or oxalates. Also, the therapeutic effect of oxalic acid or oxalate can be enhanced by decreasing or eliminating the ingestion or administration of one or more of these blockers and/or increasing the ingestion of oxalic acid or oxalate. Oxalic acid or oxalate enhancers which increase the beneficial effect of oxalic acid or oxalate include long chain fatty acids and the like which bind with or otherwise eliminate oxalic acid blockers such as calcium.

High levels of oxalic acid or oxalate can produce side effects of diarrhea, indigestion, damage to the digestive tract, and kidney damage or renal failure. Hence, prolonged ingestion or administration of high quantities of oxalic acid or oxalate should be avoided so that the beneficial therapeutic effect of the reduction, control, or treatment of tumors, cancers, neoplasia, neoplasms, infectious or pathogenic bacterial, viral, or other disease can be enjoyed without harm to other systems or parts of the body.

As mentioned above, oxalic acid or ethanedioic acid ($C_2H_2O_4$), is a dicarboxylic acid and is present in many plants and vegetables, notably in those of the Oxalis and Rumex families, where it often occurs in the cell sap of the plants as the potassium or calcium salt (oxalate, Tables I–IV). Oxalic acid is also a product of the metabolism of many molds. Several species of Penicillim and Aspergillis convert sugar into calcium oxalate with a 90 percent yield under optimum conditions. Oxalic acid is also made by passing carbon monoxide into concentrated NaOH or heating sodium formate in the presence of NaOH.

Oxalic acid dihydrate, monoclinic tablets, prisms, and granules are considered poisonous. Anhydrous oxalic acid is crystallized from glacial acetic acid and is orthorhombic with the crystals being pyramidal or elongated octahedral.

Oxalic acid is listed as being caustic and corrosive to the skin and mucous membranes. Ingestion may cause severe gastroenteritis, with vomiting, diarrhea, or melena. Renal damage can occur as a result of formation of excessive calcium oxalate crystals. Convulsions, coma. or death from cardiovascular collapse can also occur.

Common uses of oxalic acid include as an analytical reagent, in calico printing and dying, for bleaching straw and leather, removing paint or varnish, rust or ink stains, cleaning wood, and manufacturing oxalates, blue ink, celluloid, intermediates and dyes, in metal polishes, in purifying methanol, for decolorizing crude glycerol, for stabilizing hydrocyanic acid, as a general reducing agent, in ceramics and pigments, in metallurgy as a cleanser, in the paper industry, in photography, in process engraving, in rubber manufacturing, in making glucose from starch, as a condensing agent in organic chemistry, and as a veterinary hemostatic agent when mixed in 5 percent solution with 5 percent malonic acid.

As described in "Oxalic Acid in Biology and Medicine" by A. Hodgkinson, 1977, oxalic acid was formerly used intravenously as a hemostatic agent and topically as an antiseptic in man and other animals but this was discontinued because of its toxicity and the danger of precipitating insoluble calcium oxalate in the tissues. Oxalic acid is a relatively strong acid having a first dissociation constant being exceeded by that of only a few halogen-substituted carboxylic acids. Oxalic acid forms neutral and acid salts with monovalent metals and ammonia. Oxalic acid forms a number of oxalates or salts including calcium oxalate. potassium oxalate, sodium oxalate, strontium oxalate, magnesium oxalate, and the like. Oxalic acid also inhibits the activity of a number of enzymes possibly due to the competition between oxalate and a structurally similar substrate of the enzyme. Precipitation as the calcium salt is the classical method of separating oxalic acid from other substances. Although calcium oxalate is generally considered to be an insoluble salt this is a relative term and its solubility in water is actually 6–7 mg/l at room temperature. Biological fluids contain many substances that affect the solubility or rate of crystallization of calcium oxalate or co-precipitate with the salt. For example, magnesium, polyphosphates and other polyelectrolytes affect the solubility or rate of crystallization of calcium oxalate while phosphate and sulphate ions, uric acid and citric acid co-precipitate with the salt.

Also as described in "Oxalic Acid in Biology and Medicine", oxalic acid and its salts are widely distributed among the higher plants. Oxalic acid is sometimes present in plants as the free acid, but more usually, however, it is present as a soluble or insoluble salt, for example, the acid and neutral sodium and potassium salts and the ammonium salt. Calcium oxalate is the most common insoluble salt but relatively large amounts of magnesium oxalate occur together with calcium oxalate in plants such as beet root, spinach, and buckwheat. Under conditions of calcium deficiency, strontium, magnesium, or barium oxalate can be substituted for calcium oxalate in a wide variety of plant species depending upon the mineral environment.

Further, as mentioned in "Oxalic Acid in Biology and Medicine", there have been many studies of the oxalate content of individual foodstuffs (see Tables I–IV), but few estimates have been made of the total daily intake of oxalate by animals or man (see Table V). This is surprising in view of the effect of oxalate on calcium availability and the high incidence of calcium oxalate renal stones in many parts of the world. As shown in Table V, the reported numbers for daily oxalate intake range from 70–980 mg/per day of anhydrous acid for healthy adult males. However, this information was based on the study of diets which contain no oxalate-rich foods other than tea which is the largest single source of the acid in typical English diets. If an average serving (60 g) of spinach or rhubarb had been included then the oxalate intake would have risen to between 400 and 600 mg/day but these levels are not typical for this country. Wide variations in oxalate intake may occur in countries such as India where vegetables rather than dairy products provide the main source of minerals and where many of the plants used as vegetables contain high concentrations of oxalate. Some indication of these variations has been provided by a study which found intakes ranging from 78–2045 mg/day depending on the season in the rural population of Udaipur, India. A relatively high intake was also found among upper-income groups in urban areas and was attributed to a high intake of tea and green, leafy vegetables, compared with lower-income groups.

As reported in "Oxalic Acid in Biology and Medicine", when taken with food, ingested oxalate is poorly absorbed from the gastrointestinal tract. Although oxalate absorption appears to be unaffected by metabolic inhibitors it is reduced by the presence of calcium which lowers the concentration of free oxalate ions. It is well known, for example that calcium oxalate is absorbed less readily than sodium oxalate and absorption is also reduced by the oral administration of cholestyramine (anion exchange resin which has a strong affinity for oxalate ions). Conversely, oxalate absorption is increased when the dietary intake of calcium is reduced and this is reflected in an increased urinary excretion of oxalate. In addition to a low calcium diet, the intake of dysodium ethylenediamine tetra-acetic acid (EDTA) appears to increase the absorption of oxalate by complexing of calcium with EDTA in the intestinal lumen leaving more oxalate free to be absorbed.

Also as reported in "Oxalic Acid in Biology and Medicine", the most important precursors of urinary oxalate in man are ascorbic acid, glycine, and dietary oxalate. Excretion of oxalate is also increased by the ingestion of a variety of substances including glycine, alutamic acid, purines, gelatin, and ascorbic acid. Conversely, excretion has been reported to be reduced by the administration of pyridoxine and magnesium oxide. Less than half of the normal dietary intake of oxalic acid can be accounted for by absorption into the body or excretion in the faeces. The remainder of the normal dietary intake of oxalic acid appears to be destroyed by a bacterial action in the large intestine. With a dietary intake of about 130 mg/day, more than 50 mg/day appears to be destroyed by bacterial action.

Also as reported in "Oxalic Acid in Biology and Medicine", large discrepancies have been reported in the "normal" concentration of oxalic acid in mammalian blood. Early studies obtain values ranging from 2–4 mg/100 ml of blood. Another study indicated that the normal blood concentration is probably less than 1 mg/100 ml of blood. Improved testing methods have given results in normal values within the range of 100 $\mu$g/100 ml to 800 $\mu$g/100 ml. More recent tests of human plasma have produced normal oxalic acid concentration ranging from 11.8–14.3 $\mu$g/100 ml of blood in man and 52.6 to 74.4 $\mu$g/100 ml of blood in sheep (see Table VI). A mean value of 288 $\mu$g of anhydrous oxalic acid/100 ml was reported for normal human blood, a figure which is probably much nearer to the normal value.

Feeding experiments and radioisotope studies have indicated that a considerable number of compounds are precursors of oxalic acid in animals and man, for example, glycine, glyoxylic acid, glycolic acid, ethyleneglycol, ascorbic acid, and tryptophan (Oxalic Acid in Biology and Medicine). Studies with ascorbic acid have shown that the main excretory products of vitamin C in man are oxalate, ascorbic acid, and dehydroascorbic acid. From 17–40 percent of administered ascorbic acid was excreted as oxalic acid.

As reported in "Oxalic Acid in Biology and Medicine", a high oxalate intake reduces the intestinal absorption of calcium because of the formation of insoluble calcium oxalate and prolonged exposure to such a diet may lead to loss of bone mineral, particularly if the diet is also deficient in calcium or vitamin D. This situation is unlikely to occur very often in western countries where there is a plentiful supply of milk and other dairy products and oxalate-rich foods are relative uncommon. However, in developing countries such as India the situation is often quite different because tropical vegetables frequently with a high oxalate content provide the main source of minerals and the total oxalate intake may well exceed the calcium intake in certain seasons. Dietary oxalate is poorly absorbed on a normal diet containing adequate amounts of calcium.

Further, as reported in literature including "Oxalic Acid in Biology and Medicine", poisoning from oxalic acid in animals and man has been recognized since the beginning of the 19th Century. The death rate from oxalate poisoning has declined supposedly because of a decreased use of oxalic acid in domestic cleaning fluids. Examples of chronic poisoning by absorption of oxalic acid through the skin and by inhalation have been reported. The range of lethal doses in acute poisoning is wide, varying between 2 and 30 g and depending upon a variety of factors such as the form in which the acid or its salt is taken and the amount of food, particularly calcium, which is present in the stomach and intestine. Death has occurred as early as 3 minutes and as late as 14 days after ingestion. Symptoms of acute oxalic acid toxicity in man can be divided into those caused by a local corrosive action and those resulting from absorption and excretion of the soluble oxalate. If a high concentration or the solid form is taken, the local effects may be predominant and death may result from acute hemorrhagic gastroenteritis without development of symptoms depending on absorption. If death does not result from local corrosive action then symptoms develop from the systemic effects and from renal insufficiency. The cardiovascular, neuromuscular and central nervous systems are markedly affected. The skin is pale, cold and clammy, the pulse is weak and the blood pressure and temperature are low. Numbness and tingling may develop in the extremities and cramp-like muscular and abdominal pain may be extremely severe. Local or generalized muscular twitchings occur and may progress to marked tetany and convulsive seizures. The central nervous system may show evidence of excitation or depression, varying from an acute maniacal state to stupor and coma. Death results from cardiovascular collapse or depression of the central nervous system. Renal involvement is frequent and even if the patient survives the severe local or systemic effects, death may ultimately occur from renal insufficiency, which dominates the picture from the second day. Oliguria develops and may progress to anuria.

Infection with oxalic acid producing fungi of aspergillus may result in massive deposition of calcium oxalate at the sight of infection and also renal oxalosis, leading to renal failure (Oxalic Acid in Biology and Medicine). Patients undergoing treatment with steroids, immunosuppressive drugs or cytotoxic agents are particularly liable to develop fungal infections and the increasing use of these drugs in malignancy and organ transplantation may be expected to lead to an increased incidence of aspergillosis infection.

Oxamide (ethanediamide, oxalamide, oxalic acid diamide, or ethanedioic acid diamide, or $C_2H_4N_2O_2$) is metabolized in the body to form oxalic acid.

In accordance with the present invention, therapeutically effective amounts of at least one therapeutically effective form of oxalate or oxalic acid including, oxalic acid dihydride, anhydrous oxalic acid, potassium oxalate, sodium oxalate, oxamide, plants or vegetables containing oxalic acid or the potassium salt thereof, or combinations thereof are administered periodically to prevent, control, or treat infectious or pathogenic bacterial, viral, or other microbial diseases or conditions and/or neoplasia, cancers, tumors, neoplasms, and the like. Further, these compounds are administered along with a therapeutically effective reduction in the administration or ingestion of oxalic acid or oxalate blockers such as calcium, potassium, vitamin C, vitamin B6, citric acid, alcohol, or combinations thereof.

Also, in accordance with the present invention, severe gastroenteritis, vomiting, diarrhea, melena, renal disease, renal damage, convulsions, coma, cardiovascular collapse, and the like caused by oxalic acid are treated or prevented by limiting or by reducing oxalic acid or oxalate intake and/or administering therapeutic quantities of oxalic acid or oxalate blockers such as calcium, alcohol, potassium, citric acid, vitamin B6, vitamin C, and combinations thereof.

Oxalic acid dihydrate is commercially available in powdered, granular or crystal form or in liquid form for use as an industrial cleanser or solvent preparation.

In accordance with the present invention, oxalic acid may be present in a free acid, ester, lactone, or salt form. Also, oxalic acid, oxalate or related compound having the desired beneficial effect may be used as a composition, additive, supplement, remedy, and the like alone or in combination to prevent, control, or treat cancer, tumors, neoplasia, neoplasms, infectious or pathogenic bacterial or viral diseases, and the like.

In accordance with the present invention, a therapeutic composition may be formed by adding oxalic acid dihydrate to food or drink to provide for the oral ingestion of a therapeutically effective quantity of oxalic acid.

A therapeutic composition of oxalic acid or oxalate compound of the present invention may be prepared by forming a food or drink including plants or vegetables high in oxalic acid or oxalate, for example carrots, carrot juice, chives, parsley, beets, spinach, or combinations thereof (see Tables I–IV).

A therapeutic composition of the present invention in the form of a daily supplement, pill, gel cap, pharmaceutical, or the like is prepared by placing a therapeutically effective amount of oxalic acid or oxalate compound in pill form for oral ingestion as directed.

A therapeutic composition of the present invention in cream or ointment form for topical administration of oxalic acid is prepared by mixing a dilute concentration of oxalic acid in a solvent such as distilled water, ethanol, acetone, propylene glycol or polysorbate to form a solution which is then mixed in a conventional manner with a commonly available cream or ointment base such as hydrophilic ointment or petrolatum. Therapeutic compositions of the instant invention may also be formulated in gel, lotion, spray, stick or powder form.

It is believed that the therapeutic effect of the oxalic acid or oxalate in treating tumors, cancers, neoplasia, neoplasms, infectious or pathogenic microbial, bacterial or viral diseases, and other disorders affecting humans involves the administration whether it be topical, oral, by injection, suppository, or the like of a therapeutic and beneficial quantity of oxalic acid in one of its free acid, salt, or other forms to cause contact of oxalic acid with the bacteria or virus, and/or to elevate the blood oxalic acid level to between 350 $\mu$g/100 mL and 450 4$\mu$g/100 mL, preferably 425 $\mu$g/100 mL and/or the urine oxalate level to between 40 mg/L and 80 mg/L, preferably 60 mg/L for a 70K human.

Also in accordance with the present invention in the treatment of canines, an oxalic acid or oxalate level chart for canines and felines differs from that for humans in that the desired therapeutic effect can be produced from 14 mg/L to 50 mg/L, preferably 22 mg/L oxalate level in the urine of a 25 K animal as compared with 40 mg/L to 80 mg/L, preferably 60 mg/L in the human urine. Likewise, the normal blood oxalic acid level of an animal such as canine or feline differs from that of humans.

Along this line, it has been determined that about 1 gram per day intake of oxalic acid provides about a 22 mg/L level of oxalate in the urine of a 25 Kilogram (K) canine.

In accordance with one embodiment of the present invention, a multiple vitamin formula having oil and water soluble vitamins with minerals in tablet form with a suggested use to take one tablet daily with a full glass of distilled water preferably within an hour of a meal or as directed by a physician, includes about 100 mg oxalic acid together with 5,000 IU vitamin A, 60 mg vitamin C, 400 IU vitamin D, 30 IU vitamin E, 25 mcg vitamin K, 1.5 mg thiamin (vitamin B1), 1.7 mg riboflavin (vitamin B2), 20 mg niacin, 2 mg vitamin B6, 400 mcg folate, 6 mcg vitamin B12, 30 mcg biotin, 10 mg pantothenic acid, 162 mg calcium, 18 mg iron, 109 mg phosphorus, 150 mcg iodine, 100 mg magnesium, 15 mg zinc, 20 mcg selenium, 2 mg copper, 2.5 mg manganese, 25 mcg chromium, 25 mcg molybdenum, 36.3 mg chloride, 40 mg potassium, 5 mcg nickel, 10 mcg tin, 2 mg silicon, 10 mcg vanadium, and 150 mcg boron. Such a multiple vitamin formula with added minerals provides a 100% daily value of at least vitamin A, vitamin C, vitamin D, vitamin E, vitamin B1, vitamin B2, niacin. vitamin B6, pholate, vitamin B12, pantothenic acid, iron, iodine, zinc, and copper. A daily value has not been established for oxalic acid. Each tablet would contain the following ingredients: oxalic acid or oxalate, oxalic acid dihydrate, anhydrous oxalic acid, or other form of oxalic acid or oxalate, or combinations thereof together with dicalcium phosphate, magnesium oxide, potassium chloride, ascorbic acid, ferrous fumarate, calcium carbonate, gelatin, starch, cellulose, dl-alpha, tocopherol acetate, hydroxypropyl methylcellulose, croscarmellose sodium, sodium starch glycolate, niacinamide, zinc oxide, silicon dioxide, D-calcium pantothenate, sodium metasilicates and oxides, titanium dioxide, hydroxypropyl cellulose, polyethylene glycol 3350, manganese sulfate, magnesium stearate, pharmaceutical glaze, polysorbate 80, pyridoxin hydrochloride, copper oxide, povidone, sodium and potassium borates, riboflavin, vitamin A, acetate, thiamin mononitrate, beta carotene, resin, folic acid, potassium iodide, chromium chloride, ergocalciferol, sodium molybdate, sodium selenate, yellow 6 lake, sodium metavanadate, stannous chloride, nickelous sulfate. phytonadione, biotin (U.S.P. method 2), and cyanocobalamin (U.S.P. method 2). This product would be formulated per official U.S.P. standards to meet disintegration or dissolution, weight, purity, and potency requirements.

An alternative embodiment of the present invention would include a multiple vitamin and mineral tablet or daily supplement including oxalic acid in one of its forms or oxalate together with all the above mentioned vitamins and minerals except those which serve as oxalic acid or oxalate blockers. For example, the inclusion of oxalic acid or oxalate blockers would be eliminated or greatly reduced so as to prevent blocking the beneficial effect of the oxalic acid or oxalate. Such blockers include calcium, potassium, vitamin B6, vitamin C, citric acid, alcohol, magnesium, resin, etc.

In accordance with at least one embodiment of the present invention, oxalic acid or oxalate is used for the treatment of infectious or pathogenic microbial, viral, bacterial, or other diseases of warm-blooded animals including humans, dogs, and the like.

In accordance with a particular embodiment of the present invention, oxalic acid or oxalate is used in a method of therapeutically treating a human including administering a therapeutically effective dosage of oxalic acid, oxalic acid salt, oxalic acid ester, or other therapeutically effective form thereof, in an amount and for a period of time sufficient to provide the desired effect.

The method as described above wherein the oxalic acid is in the form of a free acid.

The method as described above wherein the acid is in salt form.

The method described above wherein the oxalic acid, oxalate or other therapeutically effective form thereof is administered periodically for a period of time sufficient to achieve at least a clinically discernible effect, for example, a reduction in infection or the size of a tumor.

The method as described above wherein the oxalic acid, oxalate or other therapeutically effective form thereof is administered periodically for a period of time sufficient to achieve at least a substantial therapeutic effect, for example the eradication of infection or a tumor.

The method as described above wherein the oxalic acid or oxalate is administered daily.

The method as described above wherein the period of time is at least one month.

The method as described above wherein after one month the oxalic acid is administered on a weekly basis.

The method as described above wherein the oxalic acid, oxalate or other therapeutically effective form thereof is present in a therapeutically acceptable composition including a carrier.

The method as described above wherein the composition is a powder, tablet. gel cap, lotion, cream, gel, ointment, solution, mixture, food, nutritional supplement, formulation, transdermal patch, drops, or combination thereof.

In accordance with one embodiment of the present invention, a therapeutically effective dosage of oxalic acid or oxalate is administered on a periodic basis by the ingestion of one or more foods including oxalic acid in one of its therapeutically effective forms including free acid, salt, ester, lactone, anhydride, dihydrate, diamide, or the like.

In accordance with a particular example, a four pound sourdough bread loaf is made from conventional bread ingredients including flour, water, yeast, and sourdough and has added thereto two rounded tablespoons of dried, chopped parsley which is mixed with the other ingredients to be disbursed throughout the loaf. These two rounded tablespoons of dried parsley provide approximately 2 grams of oxalic acid or oxalate in the loaf of bread. Hence, half of the loaf contains about 1 gram, ¼ of the loaf contains about ½ gram, $\frac{1}{18}$ of the loaf contains ¼ of a gram, and $\frac{1}{16}$ of the loaf contains about ⅛ of a gram of oxalic acid.

In accordance with one embodiment of the present invention, the above described loaf of oxalic acid or oxalate containing sourdough bread is used in a method of therapeutically treating a warm-blooded animal by having the animal periodically ingest a portion of the loaf. For example, in the treatment of an adult male human, he could ingest daily up to about ½ of a loaf of this bread to achieve a dosage of oxalic acid of up to about 1 gram oxalic acid per day. This dosage may be reduced after a period of time and given a certain health condition to ½ gram or less oxalic acid per day, and, as such, ¼ loaf or less of the bread per day.

The above described oxalic acid or oxalate containing sourdough bread does not include any salt, sugar or preservatives since the oxalic acid serves as a preservative.

In using oxalic acid or oxalate as a therapeutic agent, one must be careful to administer the proper dosage given certain health conditions or in order just to maintain a healthy condition since an overdose of oxalic acid or oxalate can cause indigestion, heartburn, backache, or severe problems such as renal failure, heart failure, diarrhea, vomiting, convulsions, melena, and the like. It is believed that a proper balance should be maintained between oxalic acid, oxalate and their blocking agents such as potassium, barium, calcium, copper, magnesium, silver, strontium, alcohol, citric acid, vitamin B6, vitamin C, and the like. If a high dosage of oxalic acid or oxalate would reduce calcium levels, potassium levels, magnesium levels, and the like necessary for proper heart functioning, it is necessary to limit the administration of oxalic acid or oxalate to the minimum dosage necessary to provide the desired therapeutic effect without causing undesired side effects or health problems.

In accordance with the present invention, the dosage of oxalic acid or oxalate is monitored and altered as necessary by monitoring the oxalic acid or oxalate levels in the urine and/or blood in the patient, whether that patient be a human, canine, or the like. Also in accordance with the present invention, the amount of blockers such as calcium, vitamin B6, vitamin C, citric acid, alcohol, or combinations thereof are monitored in the urine and/or blood of the patient.

It has been discovered that the body of an animal such as human or canine is a complex chemical factory which requires a particular balance of compounds, chemicals, vitamins, minerals, nutrients, and the like to provide for and maintain optimum health of the animal. It is believed that too little oxalic acid or oxalate in the animal may allow for the advent of neoplasia, tumors, cancers, growths, neoplasms, bacterial or viral disease, and the like, while too much oxalic acid or oxalate may cause back pain (due to kidney trouble), heartburn, indigestion, heart trouble, nerve trouble, and the like. Thus, it is recommended that each individual case be studied and that the proper dosage of a therapeutically effective amount of oxalic acid, oxalate, enhancers, and/or blockers be administered on a periodic basis at one level to maintain proper health by preventing neoplasia, tumors, growths. neoplasms, bacterial or viral disease, and the like, at a different level to treat, combat, control, or eradicate tumors, growths, cancers, neoplasia, bacterial or viral disease, or to cleanse the blood, and at a third intermediate level once the blood is clean and relatively free of infectious or pathogenic bacteria or viruses, cancer, tumor, neoplasm or neoplasia cells, to combat, reduce the size of, or treat an existing tumor, cancer, growth, neoplasm or infectious bacterial or viral disease. or the like. Since each person or animal is different. and their body chemistries operate in at least some small fashion differently than other persons or animals, the administration of a therapeutically effective dosage of oxalic acid, oxalate, enhancers, and/or blocking agents should be reevaluated and monitored on a regular basis by, for example, physical examination, X-ray, CAT scan, MRI imaging, sonogram. biopsy, blood analysis, urine analysis, fecal analysis, as well as other conventional diagnostic techniques. It is believed that a proper balanced diet including foods containing oxalic acid in one of its forms including oxalate which may be metabolized by a human or other warm-blooded animal can serve to maintain proper health, extend life, increase the quality of life, increase energy, increase cranial activity, prevent neoplasia, tumors, cancers, neoplasms, infectious bacterial, viral, or microbial disease, etc., help to combat viruses, bacteria, improve the immune system, and provide other beneficial short term and long term health effects.

Some forms of oxalic acid or oxalate which may prove beneficial to humans and other warm-blooded animals, include ethanedioic acid (free acid), ethanedioic acid anhydride, ethanedioic acid tri-potassium salt, ethanedioic acid barium salt, ethanedioic acid copper salt, ethanedioic acid diamide, ethanedioic acid diamonium salt, ethanedioic acid diethyl ester, ethanedioic acid dimethyl ester, ethanedioic acid disodium salt, ethanedioic acid magnesium salt, ethanedioic acid silver salt, ethanedioic acid strontium salt, ethanedioic acid dihydrate, dicarboxylic acid. as well as other forms of oxalic acid or oxalate which may be metabolized by the body, injected into the circulatory system, administered by transdermal patch, administered by suppository, administered by topical application, wash, gargle, ointment, and the like, to provide the desired therapeutic effect. Although one or more of the above may be considered poisons to humans or other warm-blooded animals. the proper administration of a selected dosage is believed to be therapeutically effective and instrumental in the treatment, prevention, and control of disease, and maintenance of good health. It is not uncommon for an agent which is a poison to provide a beneficial effect. Aspirin is one of the myriad of hundreds or thousands of poisons which provide a beneficial effect to warm-blooded animals when administered in a proper dosage.

It is believed that oxalic acid or oxalate may be one of the primary causes of the onset of osteoporosis. Too much oxalic acid or oxalate in the diet may reduce the calcium in the body to a point of causing or aggravating osteoporosis. Hence, the treatment and prevention of osteoporosis is the control of the oxalic acid, oxalate and calcium levels. Women in a high risk group for osteoporosis should be careful to increase calcium intake and decrease oxalic acid or oxalate intake to prevent, treat, or control osteoporosis.

It is believed that oxalic acid or oxalate may be a blood purifying agent which in addition to controlling, treating, or eradicating infectious bacteria or viruses and abnormal cells, oxalic acid in the blood may control cholesterol and plaque or fat buildup. Thus, the periodic or daily administration of a certain quantity of oxalic acid in one of its therapeutically effective forms including oxalate may serve to not only purify the blood, but also control, treat, or effect cholesterol, plaque, and fat buildup in the cardiovascular system or in the brain, and in so doing improve and maintain good cardiovascular health and operation.

It is believed that oxalic acid or oxalate may also be an effective treatment for parvo. Also, oxalic acid or oxalate may be used as a hemostatic and antiseptic agent in and on animals.

It is believed that oxalic acid or oxalate should be administered following exposure to X-ray radiation, X-rays, mammograms, radiation therapy, CAT-scans, nuclear or atomic exposure, radiation therapy, chemotherapy, radioactive pellet treatment, and the like, to prevent infectious or pathogenic bacterial or viral disease, or the formation of neoplasms, tumors, cancers, neoplasia by counteracting the destruction of oxalic acid or oxalate caused by the exposure or treatment.

It is believed that a dosage of oxalic acid or oxalate may also provide a reserve of energy or nutrients. Hence, a food or beverage containing oxalic acid or oxalate could be ingested prior to strenuous activity in order to increase energy, stamina, strength and/or mental activity.

It is also believed that oxalic acid or oxalate may prevent or relieve muscle soreness by helping eliminate lactic acid.

It is also believed that oxalic acid or oxalate should be administered after exposure to specific oxalic acid or oxalate decomposing bacteria to prevent infectious bacterial or viral disease or the onset of tumors. For example, workers at poultry houses may take oxalic acid or oxalate to maintain a normal level of oxalic acid or oxalate to prevent tumor development and counteract exposure to bacteria.

In addition to the administration or ingestion of oxalic acid or oxalate, it is believed that one should limit the intake of dairy products since these tend to counteract the beneficial effect of the oxalic acid or oxalate.

It is believed that oxalic acid or oxalate should be administered prior to a transplant operation to purify the blood and improve the immune system. However, it is also possible that just prior to a transplant operation the body should be purged of oxalic acid to prevent aspergillus fungi infection.

It is believed that strong magnetic fields, MRI imaging, computer terminals, power lines, cellular telephones, electronic equipment, microwave ovens, etc. may decompose oxalic acid or oxalate in the body and blood and allow the spread of infectious bacterial or viral disease and the formation of tumors, growths, cancers, etc. Hence, those subjected to strong magnetic fields and the like should increase their oxalic acid or oxalate intake to counteract such decomposition.

It is also believed that the administration of oxalic acid or oxalate may delay, prevent, control, or treat the onset of Alzheimer's Disease, lessen the effects of the disease, or improve the quality of life of a person suffering from Alzheimer's Disease.

It is also believed that oxalic acid or oxalate may be a control, treatment, remedy, or preventative for viral or auto immune-related diseases such as AIDS, HIV, SLE, BSE, CFS, and the like by preventing, lessening, or controlling the destruction of the bodies immune system. Hence, the administration, ingestion, injection, etc. of an effective amount of oxalic acid in one of its therapeutically effective forms including oxalate may serve to treat, prevent, or control the debilitating effects of auto-immune related diseases, viral diseases, bacterial infections, and the like.

As described in "Oxalic Acid in Biology and Medicine", normal human blood typically has a mean value of about 288 $\mu$g of anhydrous oxalic acid per 100 ml of blood. In accordance with the present invention, if a subject's blood is tested and their oxalic acid level is below this mean value, it is believed that they should be administered oxalic acid in one of its forms including oxalate, easily metabolized by the body to increase their blood oxalic acid level. Also it is believed that if someone is suffering from cancer, tumors, AIDS, bacterial, viral, or microbial infection, etc. that they should be administered oxalic acid or oxalate in order to increase their blood oxalic acid level to a higher value than the typical mean value.

In accordance with one embodiment of the present invention, a new scale is developed for canine and feline urine oxalate level. Since a typical human scale will not work for a canine or feline due to their different body structures and metabolism, a need exists for a canine and/or feline scale which will provide a quick-ready reference for a veterinarian or pet owner to test urine oxalate levels and adjust the oxalic acid intake in the diet accordingly.

Oxalic acid is believed to be a reducing agent, bactericidal agent, sterilizing agent, disinfectant, bacteriostatic agent, chemopreventive, chemotherapeutic agent, curative drug, antimicrobial agent, and may be an antioxidant.

In accordance with the present invention, it is believed that five or more items unnaturally constantly consumed are responsible for at least some bacterial or viral infectious disease, tumors or cancers, and the like. These items, calcium, vitamin B6, vitamin C, citric acid, and alcohol are believed to be oxalic acid or oxalate blockers. It is interesting to note that a variety of prepared foods eaten every day including cookies, cakes, canned foods, salad dressings, and the like, contain these items. Further, it is interesting to note that certain articles have proposed that persons on a low-fat diet showed less tumors or showed tumor reduction. Since red meat such as beef or liver contains vitamin B6 (pyridoxine hydrochloride) it follows that reduction or elimination from the diet also serves as a reduction or elimination of a blocker of oxalic acid or oxalate. Tables VII–XI list the pyridoxine hydrochloride content of meats and other foods.

Although others have indicated that vegetables are cancer fighters, they have listed the cancer fighting agents as antioxidants, beta carotene, or citric acid. The literature is void of a reference to oxalic acid as being a cancer fighter or preventer.

The literature suggests that tumors occur when the immune system fails to eliminate abnormal cells not consumed as a normal biological function of the body systems. In accordance with the present invention, it is believed that a low intake of oxalic acid or oxalate or a high intake of oxalic acid or oxalate blockers including alcohol, citric acid, ascorbic acid, and pyridoxine hydrochloride weakens the immune system or the body's natural cancer and disease fighting ability to the point where the body cannot control abnormal cell growth, tumors, cancer, neoplasms, bacterial or viral infectious disease, and the like. Changing the diet to include an increase in the intake of oxalic acid or oxalate and eliminating or drastically reducing the intake of oxalic acid or oxalate blockers, allows the body's immune system or natural cancer and disease fighting systems to function and eliminate abnormal cells and prevent disease.

It is believed that carrots, spinach, parsley, chives, beet leaves, garlic, collards, radishes, carrot juice, and the like are relatively high in oxalic acid or oxalate and should be eaten or consumed in order to build a high concentration of oxalic acid or oxalate in the body. It is believed that if one can maintain a balanced diet and assure an adequate level of oxalic acid or oxalate in the system then the body's natural protection mechanisms, immune system, and the like can prevent, treat, and control tumors, growths, cancers, viral or bacterial diseases, chemical toxins, and the like.

Over the years, many claims have been made regarding the beneficial health effects of many fruits, vegetables, plants, molds, etc. Recently, it has been claimed that garlic is believed to fight infection, cancer, bacteria, virus, and heart disease, strawberries are believed to help prevent prostate cancer, and tomatoes or spaghetti sauce are believed to prevent cancer and heart attacks. A recent study indicated that two cups of coffee a day can prevent suicide in women who work.

On the other hand, plants, vegetables and chemicals which contain high levels of oxalic acid or oxalate are according to conventional wisdom thought to be poisons and to be eliminated from the diet or use. For example, those suffering from kidney stones are told to stay away from rhubarb leaves, spinach, Swiss chard, lambs quarter, and beet leaves which contain high amounts of oxalates. Also, they are told to stay away from black and green teas, and coffee which also contain oxalic acid. Further, nuts, chocolate and strawberries are cited by some as containing high-oxalate.

Opposite conventional thinking, in accordance with the present invention. it is believed that oxalic acid or oxalate is the "miracle bullet", "silver bullet", "hall monitor", or "brevet boule" that treats, kills, controls, manages, or prevents infectious bacterial or viral disease, abnormal, tumor, cancer or unspecialized cells and, thereby, treats cancers, tumors, neoplasms, infectious or pathogenic bacterial, viral, or other microbial diseases, and maintains good health. Further, it has been discovered that a high oxalic acid or oxalate intake causes a disease or cancer patient to be more talkative, verbal, have increased dexterity, physical ability, mental ability, and appear invigorated, happier and more outgoing.

The conventional treatments for cancer, tumors, growths and the like can themselves cause cancer, tumors, growths, infectious bacterial or viral disease, and the like. For example, X-rays can trigger malignant growths in certain people. Further, in accordance with the present invention, decomposition or reduction of oxalic acid or oxalate in the body caused by exposure or treatment of X-rays, CAT-scans, strong electromagnetic waves or fields, electron bombardment, microwaves, and the like reduce the level of oxalic acid or oxalate in the body and further increase the chance of growths, tumors, cancers, and bacterial or viral disease. Hence, it is believed that one should not only increase the intake of oxalic acid or oxalate, but also avoids exposure to or treatment of radiation, X-rays, electromagnetic fields and the like which tend to decompose or reduce the amount of oxalic acid or oxalate in the body.

Along this same line, it is believed that conventional testing techniques, such as the testing of carcinogens on mice may provide faulty results in that the first step typically in such testing is to irradiate the mice with radiation to weaken their immune system so that they are more susceptible to disease and carcinogens. The radiation to weaken the immune system also causes a reduction or elimination of the oxalic acid or oxalate in the mice. In accordance with the present invention, it is believed that a normal level of oxalic acid or oxalate is required in the body to prevent cancers, growths, tumors, bacterial or viral disease. Brand the like. Hence, the researchers unknowingly introduced additional cancer and disease causing factor into the testing.

In accordance with the present invention, an improved testing method would involve determining the normal oxalic acid or oxalate level of the test animal, weakening the immune system of the animal using radiation, and then administering or feeding to the animal a sufficient quantity of oxalic acid or oxalate to bring their oxalic acid or oxalate levels back up to normal prior to further testing.

Also, in accordance with the present invention, it is believed that testing, research, and examinations which include X-rays or electronic scans to insure no cancer is present or to check on the size or location of the cancer can themselves bring on disease or cancer by decomposing oxalic acid or oxalate and irritating the skin or tissue. Further, if test animals are fed a diet high in oxalic acid or oxalate blockers such as calcium, vitamin B6, vitamin C, citric acid, and the like the effective level of oxalic acid or oxalate in the animal is reduced and the test results may be skewed and possibly not representative of the natural normal animal biochemistry or system. Hence, it is believed that improved human examination and animal testing involves a reduction in the use of X-ray or electronic scans, and the incorporation of a balanced diet containing oxalic acid or oxalate and a reduction in oxalic acid or oxalate blockers.

In accordance with another embodiment of the present invention, an improved method of testing for disease or cancer includes the elimination of the use of X-rays or electronic scans during the testing process.

In accordance with another embodiment of the present invention, an improved method of testing for disease or cancer allows for the use of X-rays or electronic scans to detect the presence or absence of disease or cancer, but requires that the oxalic acid or oxalate decomposed or reduced by the X-ray or electronic scan be replaced.

In accordance with another embodiment of the present invention, an improved method of testing for disease or cancer employs the use of an improved animal feed which includes at least one form of oxalic acid or oxalate and with a reduced amount of oxalic acid or oxalate blockers from that of conventional feed.

If one is to administer and ingest oxalic acid in one of its harsher forms such as oxalic acid dihydrate, for example, a gel cap filled with 500 milligrams to 2 grams of oxalic acid dihydrate, this should be taken one hour before or after a meal and with a sufficient quantity of water such as 10 or more ounces of distilled water. In order to further reduce the possibility of harm or irritation to the digestive system, one can line the stomach before taking such an oxalic acid pill or gel cap using PeptoBismol, Tagamet, or Zyntec.

In accordance with another aspect of the present invention, workers exposed to X-rays, CAT-scans, electromagnetic fields or waves, microwaves, radar, high voltage power lines, electronic equipment and the like are given sufficient quantities of foods, beverages, supplements, treats or the like containing an effective amount of at least one beneficial form of oxalic acid or oxalate to compensate for the decomposition or reduction caused by their working environment and thereby prevent the development of tumors, cancers, infections bacterial or viral disease, other diseases, poor health, etc. which may otherwise be caused by their work environment.

In recent history, there has been an increase in breast cancer in women in the United States. In accordance with the present invention, it is believed that this increase in breast cancer may be due in part to the use of microwave ovens which emit microwaves (usually at about chest height), which when used in cooking or heating decompose the oxalic acid or oxalate in the food or beverage, the use of a myriad of electronic equipment including radios, televisions, computers, etc., and the consumption of processed foods which contain oxalic acid or oxalate blockers such as calcium, citric acid, vitamin C, vitamin B6, and the like.

In recent history, there has been an increase in throat and mouth cancer in men in the United States. In accordance with the present invention, it is believed that this increase in throat and mouth cancer may be due in part to the use of microwave ovens which, when used in cooking or heating, decompose the oxalic acid or oxalate in the food or beverage, the use of a myriad of electronic equipment including electric blankets, electric razors, electric hair blowers or dryers, radios, televisions, computers, cell phones, and the like, as well as the consumption of processed foods which contain oxalic acid or oxalate blockers such as calcium, citric acid, vitamin C, vitamin B6, and combinations thereof, and an increased consumption of alcoholic beverages.

In accordance with the present invention, it is respectfully believed that oxalic acid or oxalate is a natural chemopreventive, chemotherapeutic, bactericidal, viricidal, antiviral, and disease preventing, treating, and controlling agent. Because it is natural, it destroys, kills, and/or controls "bad" or harmful bacteria, viruses, microbes, cancer cells, abnormal cells, growths, and the like, while allowing "good" or healthy bacteria, viruses, microbes, cells, and tissues to thrive. For example, if one kills all the bacteria in the mouth of a human or other animal, they can develop a fungus or fungal infection referred to as thrush. Using the natural therapeutic oxalic acid or oxalate solution as a mouth rinse or gargle only kills the "bad" or infectious bacteria and, therefore, does not lead to an unwanted fungal infection. Further, since oxalic acid or oxalate in one of its therapeutic forms is believed to be a natural disease and cancer preventing, controlling, or treating agent, it is believed that the diseases or cancers being treated, controlled, or prevented, do not become immune to the oxalic acid or oxalate.

In accordance with another embodiment of the present invention, a person who believes they have been subjected to radiation, strong electromagnetic waves or fields, microwaves, radar, strong TV or radio waves, or work in a dangerous environment where they may be subjected to X-rays or other elements which can decompose or reduce the oxalic acid or oxalate in the body, can test their blood, plasma or urine oxalic acid or oxalate level and if they find it is below normal, treat themselves with food, beverages, supplements, pills, capsules, and the like containing oxalic acid or oxalate to bring their level back up to a normal healthy level. Further, such a person can pre-treat themselves prior to exposure with oxalic acid or oxalate to reduce the chance that their levels will drop below normal levels. This should prevent or reduce the increased risk to developing cancers, tumors, viral or bacterial and viral diseases, and the like caused by having below normal oxalic acid or oxalate levels in the body.

Solutions of oxalic acid are decomposed by radiation. This has been the basis of a method for measuring radiation dosage in the sterilization of food and medical products. The absorbed dose is determined from the decrease in oxalic acid concentration which Reoccurs during irradiation (FIG. 1).

In addition to the information provided in Table IV, nuts contain high concentrations of calcium, magnesium, iron and relatively high concentrations of oxalate. For example, almond, cashew, peanut, pecan, and walnut all contain oxalic acid concentrations ranging from 200 mg/100 g–600 mg/100 g. Forage grasses and other pasture plants frequently contain high concentrations of minerals but many of them also contain high concentrations of oxalate. Further, many beverages including beers, wines, and fruit drinks contain low concentrations of oxalate but tea, coffee, cocoa, and chocolate contain relatively high concentrations of oxalate. Tea, in fact, is listed as being the largest single source of oxalate in English diets.

According to Occupational Health Services, Inc. (OHS), oxalic acid has a CAS number: 144-62-7A a RTECS number: R0245000, trade names or synonyms ethanadoic acid, aktisal, aquisal, dicarboxylic acid, phosphotex 760 grain refiner, $C_2H_2O_4$, and OHS17360. Oxalic acid is in the chemical family carboxylic acid, aliphatic and is listed as a poison with a level three out of a scale 0–3 for health, and a level 1 fire rating.

In accordance with the present invention it is believed that conventional wisdom that the cause of acorn poisoning is tannic acid is wrong and that it is instead the oxalic acid which is extremely damaging to renal tissues. It is believed that the oxalic acid or oxalate level in oak trees is very high, especially in mold that grows on the bark.

Also, it is believed that the treatment for oxalic acid or oak poisoning is to increase oxalic acid or oxalate blockers, such as pyridoxine hydrochloride, citric acid, calcium, magnesium, and alcohol such as ethanol to eliminate or carry the oxalic acid through the renal system.

Oxalate nephrosis is probably the most common cause of toxic death in dogs. Typically, the source of oxalate poisoning is ethylene glycol (antifreeze). The ethylene glycol is metabolized to oxalate and oxalic acid by an enzyme called alcohol dehydrogenase. Ethylene glycol by itself is not toxic, but when the enzyme, alcohol dehydrogenase, works on it to produce a toxic material (oxalate), then it becomes toxic. Antifreeze poisoning is treated with alcohol (ethanol) to keep the alcohol dehydrogenase enzyme busy so that the antifreeze can be eliminated, unaltered, and in a non-toxic state. A major contributor to death is also metabolic acidosis caused by oxalic acid accumulation. It is almost as important to control the acid-based status as it is worrying about the accumulation of oxalate.

There are several other causes of oxalate nephrosis which are extremely rare. Overdoses of vitamin C have been shown to cause oxalate nephrosis in humans, and in at least one goat. Vitamin B6 (pyridoxine hydrochloride) deficiency and methoxyflurane anesthesia may also induce the condition. Aspergillus sp. fungi also produces high levels of oxalate and these fungi are almost ubiquitous and grow on many feed stuffs. There are a variety of plants other than oak, for example halogenten, greasewood, sorrel, dock, setaria grass, sugar beets, and several others that contain oxalic acid.

Oxalate nephrosis produces a very specific lesion in the kidney when viewed under the microscope. You can actually see the oxalate crystals. A pathologist who is unaware of primary hyperoxaluria would obviously draw the conclusion that the kidney lesions were the result of oxalate nephrosis.

Typically, cancer, tumors, growths, and the like are treated by invasive unnatural techniques, such as surgery, biopsy, X-ray radiation, oncological chemotherapy, and the like. In accordance with the present invention, it is believed that the primary treatment for cancer should be the all natural. non-invasive, use, administration, and the like of oxalic acid in one of its therapeutically effective forms including oxalate in a sufficient quantity and on a periodic basis to provide the desired therapeutic effect.

Essiac tea was tested and found to have a pH of about 4.79 when the powder was added to boiling distilled water.

The inventor continued to search for other uses of the "miracle bullet" oxalic acid or oxalate compositions for treating the body and immune system. The inventor used a dental hygiene composition of oxalic acid and distilled water (150 mg diluted in 300 ml of distilled water) on a disciplined daily schedule and noticed that besides the removal of and prevention of any build up of tarter or plaque in the mouth, that there was also a remarkable improvement in the condition of his gums and mouth tissue, including the tongue surface. There was no more occasional bleeding of the gums during daily brushing, and the surface of the tongue appeared to be more smooth with an even coloring across the surface.

On another occasion, the inventor formulated a cream of powdered oxalic acid and a hydrophilic cream to topically treat small tumors on the skin surface of the inventors toy poodle. Following examination and application of the composition to 3 tumors on the poodle, the veterinarian applied the cream to a sore on his own hand having a red appearance and soreness of infection. Following one application of the cream the infection in the sore on the hand was eliminated and the sore healed quickly.

During a veterinarian dental examination of the inventor's pet dogs, one dog had a moderate build up of tarter and plaque on the teeth and gingivitis in the upper gums, both sides of the mouth. At the completion of the exam, rather than treat the gingivitis with an injection of antibacterial medication followed by oral medication, it was agreed the inventor would commence daily brushing of the dog's teeth. The formula used for the brushing was a mix of 150 mg. of oxalic acid in 300 ml of distilled water. The inventor began a daily brushing of the dog's teeth paying particular attention to the upper gums. The brushing was done first thing in the morning before the dog had anything to eat or drink. After the fourth day of brushing, the inventor/owner of the dog, noticed the redness of the gingivitis was disappearing and after one week returned the dog to the veterinarian for a follow-up exam. The exam revealed no more evidence of gingivitis and no tarter but moderate plaque remained. The veterinarian recommended cleaning one side of the dogs upper teeth and continuing with the daily brushing routine.

On another occasion, the inventor's pet poodle had torn a toenail which became infected. The infection was in an advanced stage which was extremely sensitive and the poodle would not use the leg while walking. The poodle was examined by the veterinarian, received an injection of a antibiotic, and oral capsules were to be given. The inventor began an immediate soaking of the paw in a composition or solution of 150 mg of oxalic acid in 300 ml of distilled water twice a day. After just two soakings the infection had improved dramatically, and the poodle used the leg without any signs of a limp.

On another occasion while visiting the veterinary clinic, the inventor noticed the receptionist had symptoms of a cold, and upon questioning the receptionist learned she was treating a cold which was into the start of the second week. When the inventor suggested the receptionist use the solution formulated for dental hygiene as a remedy for the cold, the receptionist agreed to do so. The inventor advised the receptionist that, each morning immediately upon rising, and prior to any other substance being put into the mouth, she should take approximately one teaspoon of the solution in her mouth, holding it for a minimum of two minutes, swishing the solution gently around the mouth, then discarding the solution and rinsing the mouth with warm water two or three times. The procedure began Friday night and the following Monday morning the cold was gone.

On another occasion the inventor's private attorney reported that canker sores (ulcers) inside his mouth which he had been experiencing over an extended period of time, disappeared one week after he began using the inventor's dental hygiene rinse on a once-a-day use of the composition. Also of significance was the attorney's Q-Tip application of the composition to a persistent sore on the inside of a nostril of his nose, and the sore healed.

On yet another occasion a subject who complained of continuously being prescribed antibiotic pills without any improvement in continuous flu and cold-like symptoms began the present method of mouth rinse and gargle first thing each morning and last thing at night before retiring each day and reported experiencing significant improvement in the symptoms after three days of following the recommended usage. The dilute solution was the bench mark solution.

On still another occasion a pharmacist, consultant to the inventor, awoke at 2:30 a.m. with a very sore throat, unable to swallow without severe pain, remembered the inventor's description of his own experience, mixed two teaspoons of the bench mark mixture and two teaspoons of warm water, held the mixture in the mouth for two minutes and gargled well. After a 15-minute wait, repeated the procedure and then retired. Upon arising at 6:30 a.m., repeated the procedure one time before leaving for the pharmacy. The pharmacist reported that at 11:30 a.m. all symptoms of the sore throat and flu virus were gone.

On yet another occasion, a veterinarian associate on a call to a horse ranch for the birth of a foal encountered some complications during delivery and required assistance by the veterinarian and an extended stay following the birth and a delay in effecting personal hygiene which resulted in staph infection in scratches and skin abrasions which were treated by a topical application of a cream composition of Velvachol cream and oxalic acid and the disease and soreness was relieved.

Two cases are recorded where use of the present dilute solution or oxalic acid and distilled water composition showed remarkable reduction of the effects of the flu virus. Rinsing of the mouth for a minimum of two minutes followed by a lengthy gargle three times a day for a period of four days completely removes all soreness of throat and nose and periodic use of a teaspoon of dried parsley placed between the lower lip and teeth, as one would use snuff, acted immediately as a decongestive agent to relieve soreness and congestion of the chest and further acted as an expectorant of heavy phlegm and an agent for drying of mucus.

150 mg of oxalic acid in solution in 300 ml of distilled water is the preferred and bench mark solution or composition in the uses described above. In accordance with the present invention, an oxalic acid and distilled water solution or composition may contain anywhere from greater than zero to less than about 500 mg of oxalic acid per 300 ml of distilled water, preferably 50 to 425 mg of oxalic acid dihydrate per 300 mls of distilled water. Depending on the disease or condition being treated, the amount of oxalic acid may be increased or reduced from the bench mark solution of 150 milligrams of oxalic acid in solution in 300 ml liters of distilled water. For example, in treating a strong flu, one may dissolve 400 milligrams of oxalic acid in a solution of 300 milliliters of distilled water. In treating a normal cold, one may use the bench mark solution of 150 mg of oxalic acid in solution in 300 ml of distilled water. For treating an infectious bacterial condition or disease, such as infection of a small cut or sore, one may use 50 to 75 mg of oxalic acid in solution in 300 ml of distilled water. Although there is mention of the use of a particular amount of 150 mg of oxalic acid in solution in 300 ml of distilled water to form the bench mark solution, it is to be understood that one may use, for example, 250 mg of oxalic acid in solution in 500 ml of distilled water and have the same concentration of oxalic acid in solution.

Also in accordance with the present invention, it is contemplated that one may use 0.05 percent oxalic acid in a distilled water solution for use as eye drops, nose spray, and topical or cream applications. Also, a high level of 8 grams of oxalic acid in solution may be used in intravenous injection over a 24-hour period. The bench mark mouth rinse having 150 mg of oxalic acid in 300 ml of distilled water has a pH of about 2.3. In accordance with the present invention, a mouth rinse may have a pH of about 6 to 1 depending on the application. Further, gelcaps and pills can be filled with from 1 mg in a pill to about 1 gram of oxalic acid and dihydrate (gr) in a gelcap. The exact concentration of oxalic acid required for treatment depends on the particular person being treated, the particular viral or bacterial infection, the stage of infection or treatment, and the like.

If one undergoing treatment with oxalic acid or oxalate in one of its therapeutically effective forms experiences symptoms or believes that they have ingested too high a dosage of oxalic acid, they may eat 2 to 3 spoons of crushed pineapple to reduce heartburn or indigestion.

In accordance with the present invention, it is preferred to use pure carrot juice as a dietary supplement or composition for administering oxalic acid to one undergoing treatment. One brand of frozen pure carrot juice has a pH of about 6.2. Another brand of canned pure carrot juice has a pH of 5.5.

In accordance with another embodiment of the present invention, an oxalic acid or oxalate composition takes the form of a gelcap or capsule containing an effective amount of dried parsley in a fatty acid such as oleic and linoleic fatty acids like emu oil.

In accordance with the present invention, it is believed that an adult human may be treated with an effective amount of oxalic acid or oxalate ranging from about 0.05 mg to about 8.0 gr per 24-hour period.

In accordance with the present invention, those undergoing treatment with oxalic acid or oxalate in one of its therapeutic effective forms experience a return of good color to the skin, a boosting in the immune system. an increased vigor.

Some forms of oxalic acid or oxalate which may prove beneficial to humans and other warm-blooded animals, include ethanedioic acid (free acid), ethanedioic acid anhydride, ethanedioic acid tri-potassium salt, ethanedioic acid barium salt, ethanedioic acid cooper salt ethanedioic acid diamide, ethanedioic acid diamonium salt, ethanedioic acid diethyl ester, ethanedioic acid diethyl ester, ethanedioic acid disodium salt, ethanedioic acid magnesium salt, ethanedioic acid silver salt, ethanedioic acid strontium salt, ethanedioic acid dihydrate, dicarboxylic acid as well as other forms of oxalic acid or oxalate which may be metabolized by the body, injected into the circulatory system, administered by transdermal patch, administered by suppository, administered by topical application, or administered orally, and the like, to provide the desired therapeutic effect. Although one or more of the above may be considered poisons to humans and other warm-blooded animals, the proper administration of a selected dosage is believed to be therapeutically effective and instrumental in the treatment, prevention, control, and cure of infectious bacterial, viral or microbial disease and the maintenance of good health. It is not uncommon to provide a beneficial effect from an agent which is known as a poison. There is a myriad of hundreds or thousands of poisons which provide a beneficial effect to warm-blooded animals when administered in a proper dosage.

In accordance with the present invention, a method of impeding the apoptosis of CD4 cells and persons infected with human immunodeficiency virus includes the steps of externally feeding or otherwise administering to the infected person or other animal a nutritional product which contains oxalic acid or oxalate in a therapeutic quantity sufficient to impede apoptosis of CD4 cells.

In accordance with another embodiment of the present invention, oxalic acid or oxalate compositions and methods are used to treat, prevent, or control AIDS and HIV infection in humans and other animals by administering a therapeutic quantity of oxalic acid or oxalate composition. source of oxalic acid or oxalate, nutritional product, supplement. solution, agent, curative, control, impediment, food, feed stuff, rinse, mouthwash, mouth rinse, wash, formulation, dosage, pharmaceutical agent, dietary supplement, intermediate, product, composition, anti-AIDS or anti-HIV agent, vaccine, immune system stimulant, substance, drug, chemopreventive, chemical, chemosurgical agent, chemotherapy agent, chemotherapeutic agent, solution, solute, slurry, mixture, medicine, remedy, medication, salve, ointment, balm, cream, analgesic, medicinal agent, treating agent, preventing agent. retarding agent, impeding agent, delaying agent, controlling agent, anabolic agent, health improving agent, health-supplementary food, enriched fraction, oncological or oncologic agent, tumor treating agent, disease treating agent, infection treating agent, fungal treatment, remedy, antimicrobial agent, microbial treatment, bacterial treatment, and the agent for treating, controlling, improving, preventing, the symptoms of pathological diseases such as bacterial, viral, and the like, as well as a supplemental composition or treatment to be used in conjunction with conventional compositions and treatments, or the like.

In accordance with still another embodiment of the present invention, oxalic acid or oxalate compositions and methods are used to improve sustained energy and as anabolic compositions and methods in humans and other warm-blooded animals. Oxalic acid or oxalate compositions provide for sustained energy and nutrition to support an anabolic physiological state in humans and other animals by providing or otherwise administering to the human or other animal a therapeutic quantity of oxalic acid or oxalate. The oxalic acid or oxalate compositions and methods may supplement other conventional compositions and methods such as lipids, bio-available minerals in the form of amino acid chelates, anabolic nutrients, vitamins, antioxidants, and lipotropic agents to provide an optimal sustained energy and anabolic nutrition formulation. When administered, it is believed that the oxalic acid or oxalate compositions facilitate sustained energy and delivery of nutrients to appropriate sites within the body for efficient utilization in the anabolic physiology.

The Human Immunodeficiency Virus (HIV) causes AIDS. The virus attacks certain white blood cells, called T-cells and weakens the body's immune system. Acquired Immunodeficiency Syndrome (AIDS) occurs when an HIV-infected person develops a life-threatening condition or their number of disease fighting T-cells becomes dangerously low. Current data indicates that among persons age 25–44 years old, HIV infection is now the leading cause of death in men and is the third leading cause of death in women in the U.S. In 1995, approximately 40,000 Americans contracted HIV. Worldwide, one million people died from AIDS last year and reported cases increased by 19 percent.

It has been about 15 years since the HIV/AIDS virus was first identified. Tragically the AIDS epidemic has claimed 4.5 million lives, worldwide. Today, significant strides are being made in understanding the virus and ways to battle the disease. There are 42 approved medicines and over 120 drugs currently being developed by pharmaceutical companies to fight HIV/AIDS.

One promising advance in newly developed pharmaceuticals for fighting HIV/AIDS is a new class of medicines called protease inhibitors. Studies show that when a protease inhibitor is combined with one or more of the established HIV/AIDS medicines, they work A together to attach the HIV virus at different stages of its progression. This combination or "cocktail" therapy has been shown to reduce the level of HIV in the bloodstream by up to 99 percent in some patients and, thereby. potentially halting or slowing the advancement of the disease.

In accordance with the present invention, oxalic acid or oxalate compositions are used alone or combined with one or more of the established HIV/AIDS medicines to work together to inhibit, impede, fight, or the like, the HIV virus at one or more stages of its progression or development. Hence, a new combination or "cocktail" therapy includes protease inhibitors, established HIV/AIDS medicines, and oxalic acid or oxalate compositions.

Also in accordance with the present invention, oxalic acid or oxalate compositions alone or together with established HIV/AIDS medicines can be used to treat the symptoms of HIV/AIDS infection including swollen lymph glands, fever or night sweats, weight loss, fatigue, diarrhea, skin problems, sores in the mouth, cough, shortness of breath, vaginal yeast infections, and the like. Further, oxalic acid or oxalate compositions can be used to treat the serious illnesses that occur with AIDS including pneumonia, pneumocystis carinii pneumonia (PCP), kaposi's sarcoma (KS), skin cancer, organ tumors, infections of the nervous system which can damage the brain and spinal cord, opportunistic infections, including fungal, parasitic, viral, and bacterial infections, tuberculosis, and the like.

Also in accordance with the present invention, oxalic acid or oxalate compositions are used as vaccines, immunomodulators, or immunosystem stimulant that help strengthen the immune system, thus helping the body fight off HIV/AIDS infection. Further, oxalic acid or oxalate compositions and methods are used as antimicrobial agents, antibacterial agents. anti-virals, therapies, anti-infectives, anti-microbials, and anti-cancer drugs or agents to treat the diseases and opportunistic infections associated with HIV/AIDS.

It is believed that the oxalic acid and oxalate compositions and methods of the present invention will help HIV/infected people and other animals to be able to live longer, more productive and relatively symptom-free lives.

In accordance with another embodiment of the present invention, a solution or mixture has a dilute concentration of oxalic acid or oxalate as the solute in distilled water. Such a solution of a dilute concentration of oxalic acid or oxalate in distilled water can be bottled and sold as a health improving, disease preventing, disease treating, controlling, impeding, delaying, or the like agent, pharmaceutical, supplement, chemotherapy, etc. Such a dilute oxalic acid or oxalate solution can be administered or given to, for example, astronauts prior to space travel, HIV or AIDS patients, persons or other animals suffering from bacterial, viral, microbiological, or other conditions or diseases, cancer patients, tumor patients, persons subjected to high levels of radiation or electric fields, and the like. The concentration of oxalic acid or oxalate in the solution is determined by the use of the solution or disease being treated, controlled, impeded, delayed, and the like.

In accordance with another embodiment of the present invention, bottled water, sports drinks, electrolyte solutions, fruit drinks and the like are improved by adding a dilute concentration of oxalic acid or oxalate therein. The oxalic acid or oxalate is added to either counteract some of the negative effects of the items contained in these drinks and/or to supplement or improve the healthful benefit of such drinks.

In accordance with another aspect of the present invention, oxalic acid or oxalate compositions and treatments are used in canine care by dissolving a therapeutic quantity of oxalic acid in distilled water to form an oxalic acid treatment solution for treating gingivitis, tartar build-up on the teeth, general health of teeth and gums, and as a topical antiseptic or antibiotic. For example, a half dachshund and half beagle canine was examined and found to have a build up of tartar on the teeth and gingivitis active with a slight pocket with one tooth with pus. The canine's teeth and gums were brushed regularly with the oxalic acid solution for dental hygiene and was returned to the veterinarian for examination.

In accordance with another example, a poodle having a torn toenail which has become infected received an injection of antibiotic and capsules of AMP-250 to be given three times daily. Also, the poodle's injured paw was soaked three times daily in an oxalic acid/distilled water solution the same strength as the dental hygiene solution.

In accordance with still yet another embodiment of the present invention, it is believed that oxalic acid or oxalate compositions can be used to prevent strokes in humans and other animals. An Oct. 29, 1996 ABC Evening News Report indicated that a group of seniors over age 60 had a very low rate of strokes compared to the national average. This group of some 80 people were reported to have been on a special diet high in fruit and vegetables which were high in potassium. The report theorized that the potassium was responsible for a lower level of blood pressure in the diet group and thus a lower incidence of strokes. In accordance with the present invention, it is respectfully believed that the lower incidents of strokes was due to oxalic acid in the special diet high in fruit and vegetables rather than the potassium. Potassium oxalate and potassium oxalate monohydrate contain large amounts of oxalic acid which in accordance with the present invention the oxalic acid serves as the "hall monitor" of the blood system keeping the blood en clean of plaque and abnormal cells. Hence, it is believed that the high level of oxalic acid in the potassium rich diet high in fruit and vegetables which led to the very low rate of strokes compared to the national average.

In accordance with the present invention, oxalic acid or oxalate compositions and methods are used to treat, prevent, impede, delay, control, or the like strokes in humans and other warm-blooded animals by administering a therapeutic quantity of oxalic acid or oxalate on a periodic basis, for example, daily.

In accordance with another embodiment of the present invention, an adult female human has been following a diet protocol to assist in the absorption of calcium to prevent osteoporosis. The female has also had operations to remove breast tumors which also required removal of the thyroid gland. The following protocol is designed to take calcium supplements and to add oxalic acid to a normal daily diet intake.

Calcium supplements are taken in the morning with water only. No foods or beverages containing oxalic acid are taken for two hours to allow for maximum calcium absorption without inhibiting by oxalic acid. The normal diet each day allows for vegetables and beverages (such as carrots, carrot juice, parsley) with oxalic acid in significant amounts to assure a constant normal or above normal oxalic acid level in the blood to prevent the growth of tumors.

An elderly adult female with severe arthritis and low level of bone mineral (described as looking like Swiss cheese) began following a diet protocol to assist in the absorption of calcium to prevent osteoporosis and to increase bone mineral buildup. The elderly female reduced protein intake and increased carbohydrate intake using corn oil as a supplement for the carbohydrate intake.

In accordance with another embodiment of the present invention, an oxalic acid cream made up of Velvachol cream plus 10% oxalic acid solution is used for topical application for removing, for examples, growths, lesions. from the skin in warm-blooded animals including dogs.

Also, in accordance with the present invention, a liquid-subcue injection solution of 0.1% oxalic acid in distilled water is used for subcutaneous injection treatment of, for example, skin lesions, tumors, infections, and the like, in warm-blooded animals including dogs.

In accordance with a particular example of the present invention, a 10% oxalic acid cream was used to treat a poodle.

In accordance with another particular example of the present invention, a 0.1% oxalic acid injection solution was used to treat a quarter horse.

In accordance with another particular example of the present invention, a horse with benign skin tumors was treated by adding parsley to the feed and carrots separately.

In accordance with another particular example of the present invention, a horse with two viral tumors was treated by treating one tumor with direct injection of 30 cc of a mixture of 500 miligrams oxalic acid in 500 milliliters of distilled water, the other tumor was treated with direct injection of a prescription drug.

In accordance with another particular example of the present invention, two adult humans are using a mouthwash mixture of 150 milligrams oxalic acid in 300 milliliters of distilled water as a dental cleaner.

In accordance with another embodiment of the present invention, a mouth rinse, wash, mouthwash, cleanser solution, gargle, or the like, contain about 150 milligram of oxalic acid dihydrate (from Chem One) dissolved in 300 milliliters of distilled water. This solution is produced by heating the distilled water to boiling, mixing in the 150 milligrams oxalic acid with the warm water to form the solution. The solution is placed in sterile containers for later use.

In accordance with another embodiment of the present invention, a therapeutically effective form of oxalic acid or oxalate may be used in treating AIDS, HIV, bacterial disease, viral disease, or the like when the disease, condition, or symptoms have become immune to other conventional treatments.

In accordance with another embodiment of the present invention, an oxalic acid solution of 150 milligrams of oxalic acid dihydrate dissolved in 300 milliliters of distilled water is used as a topical agent, mouth rinse or wash, dental cleanser, or the like for treating the flu, common cold, sore throat, bronchitis, and other infections, viral or bacterial diseases.

The second weekend of November, 1997, a woman properly in her early 60's agreed that she would go on the oxalic acid diet of the present invention as near to 100% as possible. She had cancer of the pancreas and the liver. In both of these cancers, her prognosis was very poor. This woman had been through the conventional treatments and nothing more held any hope for her. At the time she started on the diet, she was showing a very slight yellowing of the skin. On Jan. 26, 1998, there was a call from a gentleman to report that she is doing just great. Her color has returned to normal, a very recent test showed the liver at 60% of normal and the tumors are in regression and her blood is clean. She told the gentleman who called to say she had passed the 600 pound mark of carrots. One more success for the present invention.

In accordance with another embodiment of the present invention, astronauts and other space travellers who will be subjected to extreme magnetic forces, radiation, solar radiation, and the like, are given an effective amount of a therapeutically effective form of oxalic acid or oxalate prior to, during, and after space travel to maintain normal or above normal oxalic acid blood levels and thereby counteract the decomposition of oxalic acid caused by space travel, exposure to radiation, and the like.

A man described a condition currently existing with his one year old child which sounded like the typical child's persistent low level cold. Mild chest congestion that would interfere with normal breathing at night, congested cough in the morning and persistent runny nose. We talked about what might help relieve the cold and discussed the possibility of a small amount of freeze-dried parsley placed in the child's mouth to work as a decongestant and an anti-viral biotic. It was agreed that having the child take a small amount of the parsley without water before going to sleep would be an effective way of providing oxalic acid without any side effects.

He called on October 24 to tell me that on the 18th he did have success with having his daughter eat with him a small amount of the dried parsley and has done so each night since the 18th. There is no more congestion or running nose and the child is sleeping peacefully through the night. We agreed that he should discontinue the procedure to avoid irritating the membrane of the mouth or throat. And if the symptoms do not return in the next couple of days the viral infection was cleared.

We also discussed his using the procedure with an amount of 2 teaspoons every third night during the flu season as a protective measure.

An adult male who has Hepatitis C has recently started on a high oxalic acid diet and trying hard to avoid the blockers. He has been infected for some time and knows the symptoms preceding the times when he has periods of effects from the virus. With careful monitoring, we will be able to tell if the oxalic acid is having the effect of killing the virus by either the period between attacks are longer or the effects themselves are less severe, or both.

Also, his wife was diagnosed with viral pneumonia by X-ray examination. She was given antibiotics to ward off infections because of a weakened immune system. On Friday, September 26, she was provided the mouthwash of 150 mg of oxalic acid (OA) in 300 ml of distilled water. She started the recommended procedure of approximately 2 teaspoons of wash, holding in mouth for 2 minutes then gargle, spit out wash, then rinsing mouth at least twice with warm tap water. The procedure was repeated first thing in the morning immediately after rising and before anything else was put in mouth. It was done mid-day with nothing in mouth one hour prior to wash. At night, the procedure was repeated as the last item before retiring. By Sunday afternoon, the wife experienced nearly complete relief from the effects of the viral pneumonia.

The following is a procedure using a mouth rinse of distilled water with oxalic acid dihydrate in solution. The rinse is used to brush the teeth and dentures to remove tartar and eliminate bacteria in the mouth and gums. The procedure being followed is, each morning immediately after rising, a small amount of solution (approximately 2 teaspoons) is held in the mouth and swished around teeth for a minimum of 2 minutes, removable dentures are removed, retaining maximum amount of rinse in mouth, teeth are then brushed outside and inside, specifically between teeth and at gum line, and the tongue is brushed. The rinse is then discarded and the mouth flushed 2 or more times with tap water. A denture brush is then used to clean the denture. Full dentures, upper and lower, may be cleaned using the rinse then removing the dentures to clean. Initially, the solution was 500 mg oxalic acid, 500 ml distilled water, gradually reduced to 250 mg oxalic acid in 500 ml distilled water.

George, an adult male, is a special case because he has just finished his first week of radiation and chemotherapy treatments at the Mayo Clinic, Rochester Minn. He has a malignant tumor about grape size by an inner ear at the back of the skull. He receives 15 seconds of radiation from each side of his face and 30 seconds through the back of his throat and he will receive the treatment for 7 weeks, 5 treatments per week, with 6 chemotherapy treatments spaced through the same period. George started the oxalic acid diet on October 9, had his first radiation on October 14, and began the oxalic acid rinse procedure on October 25. George is keeping a detailed log of his diet and will document any side effects and will ask the doctors each week about the progress in eliminating the tumor. I believe the tumor will be reduced more rapidly than the rate calculated by the radiologist and the doctor.

A very significant item happened Thursday, October 24. On the evening news, there was an announcement that in clinical testing, nicotine may remove plaque in the brain and may reduce the effects of loss of memory of Alzheimer victims. We describe that oxalic acid may remove plaque from the blood. It is reported in Oxalic Acid in Biology and Medicine that tobacco contains oxalic acid.

On Apr. 4, 1997, I had a visit with two gentlemen, Ken and his friend, Jon. They found out about the present research on oxalic acid. Jon had bone cancer and wanted the diet information. I told them I would not provide it unless they were willing to spend the time to not only listen, but to read the applicable research data also. They agreed. We spent 4 hours reviewing the data, and in questions and answers. Jon's bone cancer was verified by MRI and he had just previously had the first chemo treatment from his oncologist. And, in his words, "very painful and debilitating", and he did not want to take any more if it could be avoided. He was provided with the diet and lists of food and drink with oxalic acid, and list of foods with B6. Also, he was given a large container of Tone's dried parsley, cans of carrots and beets and advised to start immediately on the diet. In fact, while we were continuing to talk, he started eating the parsley and washing it down with distilled water.

I then called Jon each subsequent Saturday morning to check on his feelings and to remind him of the diet, specifically the blockers. He delayed a scheduled second treatment and did tell his doctor he was on a diet, not what diet, and he wanted to see the results. He scheduled an MRI for the May 16. I called him May 17 and he was a very happy person. The technician, in Jon's words, "could not find the spots he was looking for". Another MRI was done later the afternoon of the 16th, with a higher radiation factor. Following the second MRI the technician told Jon, he could not give him the results, the "developer had troubles". The trouble was, he still could not find the spots and wanted to tell the oncologist first.

I called Jon later and heard in his words "the SPOTS ARE GONE". His oncologist tried to get him to take another chemo treatment, saying the cancer had probably metastasized.

He is continuing on the diet to make sure the blood is clean and the oxalic acid blood level is increased, and once a week will just before retiring with nothing taken for one hour before, take a calcium supplement to build up bone minerals.

On CNN Prime Time News, there was a very short news item about a recent study that showed people with strong bones had a higher incident of cancer than people with weak bones.

The study is very significant because oxalic acid inhibits calcium absorption by the body. High calcium absorption is necessary for development and maintenance of strong bones, and would not be possible if the body was high in oxalic acid. However, high oxalic acid in the body system would not only inhibit calcium absorption but also would prevent the development of cancer.

Too high levels of oxalic acid could mean weak bones and osteoporosis.

First, my dog Missy, half dachshund and half beagle, had a dental exam and found to have a build up of tartar on the teeth and gingivitis active with a slight pocket by one tooth with pus. Her teeth and gums will be brushed daily with the solution used for human dental hygiene and returned to the veterinarian for examination weekly.

Second, my poodle, Turk, had a torn toenail which had become infected. He received an injection of an antibiotic, and capsules of Amp-250 to be given 3 times daily. Also, his injured paw will be soaked 3 times daily in an oxalic acid solution the same strength as the dental hygiene solution.

During the week following May 16, 1996, an adult female who is assisting me in documenting the history of my discovery, has been following a diet protocol as follows to assist in the absorption of calcium to prevent osteoporosis. She has also had operations to remove breast tumors which also required removal of the thyroid gland. The protocol is designed to add calcium supplements to a normal daily diet intake.

Calcium supplements are taken in the morning with water only. No foods or beverages containing oxalic acid are taken for 2 hours to allow maximum calcium absorption without inhibiting by oxalic acid. The normal diet each day allows for vegetables and beverages with oxalic acid in significant amounts to assure a constant normal or above oxalic acid level in the blood to prevent the growth of tumors.

On Sep. 20, 1996, her mother with severe arthritis and low level of bone mineral (described as looking like Swiss cheese) was started on the above protocol as related to calcium and oxalic acid to increase bone mineral build up and was advised to reduce protein intake and increase carbohydrate intake using corn oil as a supplement for the carbohydrate intake.

I received another call from a woman who went on the oxalic acid diet Jan. 3, 1998 because there is an unidentified mass in her breast. She called today to tell me that she was diagnosed a year ago last October (1997) with diverticulitis and has had irritable bowel syndrome most of her life. She has not had attacks from eating foods now that before would cause diverticula attacks prior to starting on the diet. Her husband has been troubled for years with reflux from a hiatal hernia and constantly consumed Rolaids. He went on the oxalic acid diet with his wife to lose some weight and has discovered the reflux has disappeared and he has stopped using Rolaids. Oxalic acid must be clearing up any bacteria in both husband and wife. This stuff is amazing.

The present invention is directed to oxalic acid or oxalate compositions and methods and formula for producing such compositions and for the utilizing oxalic acid or oxalate compositions including solutions, mixtures, products, creams, rinses, and the like, in the management, control, prevention, or the like, of infectious bacterial and infectious viral diseases or conditions in humans and other animals.

Even though a viral origin for cancer has not been demonstrated in man, the inventor conducted investigative research on oncogenic viruses and their relationship to man, during development of U.S. patent application Ser. No. 08/629,538. *Medical Microbiology* by Jawets, Melnick & Adelbert, 8th Edition, 1968, writes on the general properties of tumor viruses. The tumor inducing viruses can be classified into two main groups, those which contain RNA as their generic material and those that contain DNA. DNA papilloma viruses as benign warts and molluscum contagiosum have been classed as natural tumors in man and serve as models in the quest for knowledge of viral carcinogenesis in man.

When the inventor discovered the bactericidal activity of oxalic acid in the gingivitis reduction in his pet dog. The entire spectrum of the effect of oxalic acid in application for infectious bacterial and infectious viral conditions was studied, and many case studies were conducted with human volunteers among his peers. The observed interaction of oxalic acid and the infectious bacteria and infectious virus during these studies reveals that oxalic acid is indeed bactericidal and viricidal. It is stated in *Medical Microbiology* that the fundamental principal of chemotherapy is the principal of selective toxicity, which may be stated as follows, "In order to be useful for systemic treatment of infectious disease, a substance must be harmful to parasites but relatively innocuous to host cells."

Oxalic acid as a natural chemotherapy meets the stated principle. It can be administered at therapeutically acceptable levels sufficient to kill the bacterial and viral organisms and be completely innocuous to the host cells. Oxalic acid can be administered at the therapeutically acceptable levels for the time necessary to kill the organisms without any effect on host cells. It is believed that oxalic acid penetrates the encasing shell of the host cell and kills the viral nucleic acid core.

In accordance with the present invention, antimicrobial oxalic acid or oxalate compositions and methods of treatment of warm-blooded animals including humans and pets is provided which includes at least one therapeutically effective form of oxalic acid or oxalate for controlling treating, or managing bacterial diseases and viral diseases caused by germs of infectious bacteria and infectious virus. The present invention encompasses treatment of the following: Bacterial diseases caused by Gram-Positive Cocci such as Staphylococcal infections of Pneumonia, Bacteremia, Osteomyelitis, Enterocolitis, and the like. Streptococcal infections such as Hemolytic, Viridans, Enterococci, Lactic, and the like. pneumococcal infections such as Pneumonia. Sinusitis, Otitis, Meningitis, and the like. Also bacterial diseases caused by Gram-Negative Cocci, Neisseria Aerobic infections such as Meningococcus, Gonococcus, and the like. Also bacterial diseases caused by Gram-Positive Bacilli infections such as Erysipelothricosis, Listeriosis, Anthrax, Nocardiosis, and the like.

Also bacterial diseases caused by Gram-Negative Bacilli infections such as Enterobacteriaceae Salmonella, Shigellosis, Hemophilus, Tularemia, Plaque, Melioidosis, Bartonellosis, Campylobacter, and Noncholera Vibrio, and the like. Also bacterial diseases caused by Anaerobic Bacilli infections such as Clostridium Botulinum, Clostridium Tetany, Clostridia of Gas Gangrene Bacteroides, Mixed Anaerobic, Actinomycosis, and the like.

Also diseases caused by Mycobacteria, infections such as Tuberculosis and Leprosy, and the like.

Also bacterial diseases caused by Spirochetes such as Leptospirosis Lyme Disease, and Endemic Treponematoses.

Further in accordance with the present invention, oxalic acid or oxalate composition and methods of treatment for infectious nucleic acid type Viral diseases such as deoxyribonucleic acid types (DNA), and ribonucleic acid (RNA), with natural cycle chiefly in humans, spread by person-to-person contact, and transmitted from nature to man and may also infect animals. Also, diseases such as Human Immunodeficiency Virus infection (HIV) and Acquired Immunodeficiency Syndrome (AIDS).

Also Respiratory Tract Viral diseases, all serotypes, caused by Influenza, A, B. and C, Parainfluenza viruses 1–4, Rhonoviruses (common cold), Mumps virus, Adenoviruses, Reoviruses, and Epstein-Barr virus, and Infants and Adult Syncytial virus, also primary Atypical pneumonias and others.

Also Nervous System Viral diseases, all serotypes, such as Polioviruses, Coxsackieviruses, Echoviruses and high numbered viruses, Epidemic gastroenteritis viruses, Rubeola virus, Rubella virus, Varicella-zoster virus, Herpes simplex, Human herpes virus type 6, Human Parvovirus B19, Cytomegalovirus, Hepatitis viruses Types A, B, C, D, Human Papillomavirus, Molluscum contagiosum virus, and also viruses transmitted from nature to man such as the Arboviruses, togaviruses, alphaviruses, flaviviruses, bunyaviruses, and the Orbivirus, Rabies virus, Herpesvirus simiae, Arenaviruses, Filoviruses, and the like.

By way of general definition, "cancer" is any of various malignant neoplasms, a "tumor" is a neoplasm or abnormal growth of tissue, and a "neoplasm" is an abnormal new growth of tissue, or a tumor. Hence, it is respectfully believed that the words neoplasm and tumor are essentially synonymous and that a cancer is essentially any of various malignant neoplasms, tumors, or growths.

As described in the present application, oxalic acid in one of its beneficial forms was used in connection with the treatment, management, control, or the like of a growth on a thigh, a growth on an eyebrow, polyps, abdominal cancer, bladder cancer, prostate cancer, mouth tumor, melanoma (skin cancer), oral tumor, cervical cancer, brain tumor, lymph node tumors, uterine tumor, bone cancer, stomach cancer, and breast cancer. Further, as described in the Examples of the present application, oxalic acid in one of its beneficial forms is used in connection with the treatment, control, management, or prevention of tumors, brain tumors, cancers, neoplasia, acne, skin cancer, growths, breast cancer, cervical cancer, and the like. It is respectfully believed that oxalic acid in one of its therapeutic forms is a natural chemotherapy which can be used to treat all types of tumors, growths, neoplasms, infectious bacteria! or viral diseases, and the like, in warm-blooded animals, regardless of location or classification thereof. The oxalic acid diet of the present invention provides a natural chemotherapy which has been beneficial in the treatment, control, management, or prevention of growths, tumors, cancers, leukemia, bronchitis, and bacterial and viral infections. In other words, it is believed that oxalic acid in one of its therapeutic forms is a general or non-selective chemotherapeutic or chemopreventive agent, factor, or compound. In a recent Cancer Treatments publication, "chemoprevention" is described as an exciting new area of pharmaceutical cancer research that focuses on the prevention of cancer through a diverse group of natural and synthetic agents. It is respectfully believed that this publication indicates that chemoprevention is new and that prior to the invention by Applicant, one of ordinary skill in the art would not have known of the use of oxalic acid as a chemoprevention and it would not have been obvious to use oxalic acid as a chemoprevention.

Further, if the use of oxalic acid as a cancer treatment or cure were known prior to the invention by Applicant, why will more than 1.3 million cases of cancer be diagnosed this year, why has over a trillion dollars been spent on trying to find a cure for cancer, and why did the U.S. commit itself to waging a "war" on cancer with the National Cancer Act of 1971. As described in the recent Cancer Treatments publication, a so-called "magic bullet"-a single medicine or treatment-that will cure cancer has not been found. Applicant respectfully believes that oxalic acid in one of its therapeutic forms may be the "magic bullet" that is being sought and may improve and extend lives when it is used as described in the present application. Although the activity of oxalic acid is not completely understood, Applicant respectfully believes that oxalic acid attacks the nucleic acid center of tumor, cancer, neoplasm, or growth cells or tissues and thereby kills or prevents the growth of the tumor, cancer, neoplasm, growth, or the like. Applicant respectfully believes that warm-blooded animals including humans, dogs, cats, horses, and the like will benefit from the use of oxalic acid in one of its therapeutic forms as described in the present application including as a composition, nutritional supplement, diet, food additive, dental prophylactic, preventative, control factor, treatment agent, or the like.

Even further, in accordance with the present invention, it is contemplated that many different oxalic acid or oxalate containing compounds, foods, vegetables, and the like may be used in the controlling, managing, treatment, prevention, or the like of neoplasms, Neoplasia, cancers, tumors, growths, abnormal cells and tissues, infectious bacterial or viral diseases, and vascular disorders, diseases, and other conditions. For example, oxalic acid dihydrate, dried parsley, dried chives, foods containing these items, nutritional supplements containing these items, juices such as carrot juice containing these items, and combinations thereof may be used to provide the desired chemotherapeutic affect In accordance with the Detailed Description of the Invention, the following case studies confirm the therapeutic action of oxalic acid and oxalates on vascular disorders, diseases, and other conditions.

In one case, the spouse of a patient on the diet also followed the diet. The spouse was very pleased to learn from later blood tests, a condition of high blood pressure, high cholesterol, and abnormal platelets was normal, bad cholesterol levels were down, good cholesterol levels were up, and the platelet level was steady and within the desired value. The spouse was able to stop taking medicine she had taken for several years.

In another case, a patient learned of the diet when the inventor recommended a diet schedule for the patient's dog. The patient was ill with artherosclerosis and had received relief from bypass surgery. The patient was taking drug therapy for a condition of 80 percent blockage of an artery. Approximately three months after following the diet, an arteriography test revealed the blockage was reduced to 53 percent. The patient is continuing the diet In another case, a veterinarian used an oxalic acid cream solution in treating viral oral plaques in the ears of horses. It is the only treatment he has found to be successful. Following removal of the plaque, the skin was normal, healthy, and pink in texture.

In several cases, patients suffering for years with rheumatoid arthritis who were taking drug therapy, received total relief by following the diet procedure. Complete mobility was restored in joints whereas mobility had been severely restricted.

The decalcification of calcareous matter by oxalic acid has been repeatedly demonstrated. There is no drug therapy currently available capable of removing plaque and restoring the inner lining of the artery to a healthy condition.

Applicant respectfully believes that oxalic acid in at least one of its therapeutically effective forms is a general, nonselective, chemotherapeutic or chemopreventive agent, factor, or compound and has described numerous compositions, methods, protocols, regimens, diets nutritional supplements, rinses, washes, topical ointments, and the like for supplying oxalic acid in an effective amount and a beneficial form to patients.

The following are illustrative examples of methods, formulations and compositions according to the present invention. Although the examples utilize only selected compounds and formulations, it should be understood that the following examples are illustrative and are not limiting. Therefore, any of the aforementioned oxalic acids, oxalate, or related compounds may be substituted according to the teachings of the present invention in the following examples.

EXAMPLE 1

A therapeutic composition in the form of a nutritional supplement or multi-vitamin tablet containing an effective amount of oxalic acid, 8 grams (g) or less, preferably 500 milligrams (mg) or less of oxalic acid, together with conventional ingredients such as vitamins and minerals.

EXAMPLE 2

A treatment regimen or method including the oral administration of one such tablet, pill, multi-vitamin or supplement of Example 1 daily.

EXAMPLE 3

The therapeutic composition of Example 1 including 1 gram or less, preferably 500 milligrams or less of oxalic acid, together with conventional quantities of other vitamins and minerals except that one or more of the oxalic acid blockers, including vitamin C, vitamin B6, calcium, citric acid, alcohol, resin, and the like are reduced or eliminated altogether from the pill, vitamin, multi-vitamin, supplement, etc.

EXAMPLE 4

A composition rinse, or gargle for rinsing the interior surfaces of the mouth and throat made of a dilute solution of oxalic acid in distilled water, preferably less than 500 mg of oxalic acid in 300 ml of distilled water.

EXAMPLE 5

A method of treating patients including the steps of testing the blood or urine oxalic acid or oxalate levels, administering an effective amount of oxalic acid, oxalate or blockers thereof, and monitoring the levels to determine if adjustments are necessary to achieve a desired level.

EXAMPLE 6

A single medicine, "silver bullet" or "magic bullet", composition for controlling, treating or managing vascular disorders, diseases, and other conditions or for otherwise therapeutically treating patients and including an effective amount of at least one therapeutically effective form of oxalic acid or oxalate.

EXAMPLE 7

The composition as described in Example 6 wherein the therapeutically effective form of oxalic acid or oxalate is selected from the group of oxalic acid in a free acid, ester, lactone or salt form, oxalate including sodium oxalate, a nutritional supplement containing at least one form of oxalic acid or oxalate, oxalic acid dihydrate, anhydrous oxalic acid, oxamide, oxalate salts, and combinations thereof.

EXAMPLE 8

The composition as described in Example 6 wherein the composition is oxalic acid dihydrate.

EXAMPLE 9

The composition as described in Example 6 further having a pharmaceutically acceptable carrier or diluent for the therapeutically effective form of oxalic acid or oxalate.

EXAMPLE 10

The composition as described in Example 9 wherein the carrier or diluent is at least one of a gel cap and distilled water.

EXAMPLE 11

A method for controlling, treating, or managing vascular disorders, diseases, and other conditions in patients having the steps of periodically administering a therapeutically effective dosage of the composition of Example 6.

EXAMPLE 12

The method as described in Example 11 wherein the composition is administered orally or sublingually in at least one of a gel cap, tablet, powder, food additive, food, drops, liquid, beverage, pill, and capsule form.

EXAMPLE 13

A method as described in Example 11 wherein the composition is administered by injection including venous injection.

EXAMPLE 14

The method as described in Example 11 wherein the composition is administered internally by at least one of inhalation, suppository, or subcutaneous deposit.

EXAMPLE 15

The method described in Example 11 wherein the composition is administered at last once a day at a dosage of 50 mg to 6 g for patients.

EXAMPLE 16

The method as described in Example 11 further having the steps of reducing the intake of oxalic acid or oxalate blockers and/or increasing the intake of oxalic acid or oxalate enhancers.

EXAMPLE 17

The method as described in Example 16 wherein the blockers are selected from the group of citric acid, ascorbic acid, pyridoxine hydrochloride, calcium, alcohol, resins, clays, and combinations thereof.

EXAMPLE 18

The method as described in Example 16 wherein the blockers are selected from the group of dairy products containing calcium, fruits, coconut, beverages containing alcohol, ascorbic acid or citric acid including beverages such as beer, wine, vodka, gin, and the like, fruit juice based beverages, soda pop or soft drinks containing ascorbic acid or citric acid, other sports drinks, beverages or refreshments containing ascorbic acid or citric acid, red meats, or white meat of fowl including chicken, turkey, pheasant and the like containing pyridoxine, or other foods or beverages containing alcohol, citric acid, ascorbic acid or pyridoxine hydrochloride including breads or grains, resins, and combination thereof

EXAMPLE 19

A diet for treating, controlling, and managing or preventing vascular disorders, diseases, and other conditions in patients having the steps of adding to the regular diet a dietary supplement of an effective amount of at least one therapeutically effective form of oxalic acid or oxalate.

EXAMPLE 20

The diet as described in Example 19 wherein the effective form of oxalic acid or oxalate is selected from the group of oxalic acid in a free acid, ester, lactone, or salt form, oxalate including sodium oxalate, a nutritional supplement containing at least one form of oxalic acid or oxalate, oxalic acid dihydrate, anhydrous oxalic acid, oxamide, oxalate salts, natural or processed foods including plants or vegetables including parsley, chives, garlic, beets, carrots, spinach, and the like containing at least one form of oxalic acid or oxalate, beverages, liquids or juices such a carrot juice containing at least one form of oxalic acid or oxalate, and combinations thereof.

EXAMPLE 21

The diet as described in Example 19 further having the steps of reducing the intake of oxalic acid or oxalate blockers.

EXAMPLE 22

The diet as described in Example 21 wherein the blockers are selected from the group of dairy products containing calcium, fruits, coconut, beverages containing alcohol, ascorbic acid, or citric acid including adult beverages such as beer, wine, vodka, gin, and the like, fruit juice based beverages, soda pop or soft drinks containing ascorbic acid or citric acid, other sports drinks, beverages or refreshments containing ascorbic acid or citric acid or pyridoxine hydrochloride including breads or grains, resins, and combinations thereof.

EXAMPLE 23

A method of treating vascular disorders, diseases, and other conditions including the steps of reducing or eliminating the ingestion or administration of oxalic acid or oxalate blockers, administering or ingesting high dosages of oxalic acid or oxalate to raise the blood or urine oxalic acid or oxalate level above normal, and, after cleansing the infectious microbial, bacteria or virus infected blood, reducing or eliminating the administration or ingestion of oxalic acid or oxalate to maintain a normal blood or urine oxalic acid or oxalate level.

EXAMPLE 24

A therapeutic composition for purifying the blood, controlling, treating or eradicating infectious or pathogenic microbial, bacterial or viral disease from the cardiovascular system or in the brain, and maintaining good cardiovascular health and operation, having a therapeutically effective amount of at least one therapeutically effective form of oxalic acid or oxalate.

EXAMPLE 25

A pharmaceutical composition to be administered orally to patients of a mixture of a non-toxic ingestible carrier and an effective amount of a therapeutically effective form of oxalic acid or oxalate.

EXAMPLE 26

The pharmaceutical composition as described in Example 25 wherein the composition is provided in a form selected from the group of pills, powders, granules, tablets, microcapsules, gel capsules nutritional supplements, processed foods, liquids, drops, beverages, additives, and solutions.

EXAMPLE 27

A method of enhancing the beneficial effects of oxalic acid or oxalate in patients including the steps of eliminating the use of strong magnetic fields or radiation in the examination, treatment or diet (heating of food or drink) of the patient to prevent decomposition or reduction in the amount of oxalic acid or oxalate during treatment.

EXAMPLE 28

A mouthwash, gargle or oral rinse containing a dilute solution of oxalic acid and having a pH of 2.67.

EXAMPLE 29

The mouthwash, gargle or oral rinse of Example 28 containing a dilute solution of 150 mg of oxalic acid dihydrate per 300 ml of distilled water.

EXAMPLE 30

A method of treating terminally ill patients including the steps of administering a high dosage of oxalic acid or oxalate to cleanse the blood and treat the condition or disease.

EXAMPLE 31

The method of Example 30 further including the steps of stopping other chemical treatments to prevent weakening of the body or prevent the reduction of oxalic acid or oxalate in the body.

EXAMPLE 32

The method of Example 30 further including the steps of reducing the dosage of oxalic acid or oxalate after the blood has been cleansed and the condition or disease has improved.

EXAMPLE 33

The method of Examples 30, 31, 32, further including the steps of reducing the intake of oxalic acid or oxalate blockers and increasing the intake of oxalic acid or oxalate enhancers.

EXAMPLE 34

A therapeutic composition for treating vascular disorders, diseases and other conditions made up of pure carrot juice which is administered orally in 2 ounce servings to provide between 4 and 6 ounces of carrot juice daily to provide the desired therapeutic effect and desired oxalic acid or oxalate blood or urine level.

EXAMPLE 35

The carrot juice of Example 34 is mixed with other juices and flavoring agents such as tomato juice, salt, pepper, parsley, and/or celery to enhance the flavor thereof.

EXAMPLE 36

A therapeutic composition in the form of a nutritional supplement or multi-vitamin, multi-mineral tablet containing a small quantity of oxalic acid, preferably 500 milligrams or less of oxalic acid, together with conventional ingredients such as vitamins and minerals.

EXAMPLE 37

A treatment regimen or method including the oral administration of one such tablet, pill, multi-vitamin, or supplement of Example 36 daily.

EXAMPLE 38

The therapeutic composition of Example 36 including 8 grams or less, preferably 500 milligrams or less oxalic acid, together with conventional quantities of other vitamins and minerals except that one or more of the oxalic acid blockers, including vitamin C, vitamin B6, calcium, citric acid, resins, and the like, are reduced or eliminated altogether from the pill, vitamin, multi-mineral, supplement, etc.

EXAMPLE 39

A therapeutic composition or remedy for the maintenance of good health, prevention, treatment, or control of vascular disorders, diseases, and other conditions is made up of a food item such as bread, cereal, or other prepared food including oxalic acid or plant or vegetable containing oxalic acid like parsley or chives, in a sufficient quantity to provide the desired therapeutic effect.

EXAMPLE 40

A composition for improving and maintaining good health in patients and having a composition selected from oxalic acid, oxalate, oxalic acid dihydrate, a nutritional supplement containing oxalic acid, a nutritional supplement containing oxalate, a nutritional supplement containing oxalic acid dihydrate, or combinations thereof.

EXAMPLE 41

A flavor enhancer including at least one form of oxalic acid.

EXAMPLE 42

A preservative including at least one form of oxalic acid.

EXAMPLE 43

In a prepared food product, the improvement including an effective amount of at least one form of oxalic acid.

EXAMPLE 44

In a prepared food product, the improvement including the elimination of citric acid and the addition of an effective amount of at least one form of oxalic acid.

EXAMPLE 45

In a diet for promoting good health in warm-blooded animals including humans, the improvement including increasing the quantity of oxalic acid or oxalate-containing foods, and reducing the intake of oxalic acid or oxalate blockers.

EXAMPLE 46

A method for inhibiting, preventing, treating, or controlling the deleterious effects of diarrhea, indigestion, damage to digestive tract, kidney damage, or renal failure caused by high levels of oxalic acid including the steps of at least one of reducing the ingestion or administration of oxalic acid, oxalate, oxalic acid dihydrate, a nutritional supplement containing oxalic acid, a nutritional supplement containing oxalate, a nutritional supplement containing oxalic acid dihydrate, foods containing oxalic acid, foods containing oxalate, foods containing oxalic acid dihydrate, carrot juice, and combinations thereof, increasing the ingestion or administration of oxalic acid or oxalate blockers including crushed pineapple, monitoring the levels of oxalic acid or oxalate in the blood or urine, adjusting the ingestion or administration of oxalic acid or oxalate-containing compounds and the ingestion or administration of oxalic acid or oxalate blockers to achieve the desired oxalic acid or oxalate levels.

EXAMPLE 47

A method of counteracting, inhibiting, treating, controlling, or reducing the deleterious effects of high levels of oxalic acid including the steps of administering or ingesting a therapeutically effective amount of vitamin B6, vitamin B6-containing nutritional supplements, foods containing vitamin B6, or combinations thereof.

EXAMPLE 48

A method of treating a patient including the steps of determining the oxalic acid blood level or oxalate urine level of the patient comparing this level with a scale indicating below normal, normal, and above normal oxalic acid or oxalate levels, increasing the administration or ingestion of oxalic acid or oxalate if the level is below normal, reducing the ingestion or administration of oxalic acid or oxalate blockers if the level is below normal, maintaining current ingestion or administration of oxalic acid or oxalate if the oxalic acid or the oxalate level is normal, reducing the ingestion or administration of oxalic acid or oxalate if the level is above normal, or increasing the ingestion or administration of oxalic acid or oxalate blockers if the level is above normal.

EXAMPLE 49

The method as described in Example 48 wherein the oxalic acid or oxalate level scale has differing below normal, normal, and above normal level categories for different health conditions.

EXAMPLE 50

In a multi-vitamin and mineral supplement, the improvement including the addition of at least one therapeutically effective form of oxalic acid.

EXAMPLE 51

The multi-vitamin and mineral supplement as described in Example 50 further including the improvement of the reduction or elimination of oxalic acid or oxalate blockers therein.

EXAMPLE 52

An oxalic acid treatment method including the step of mixing carrot juice with other juices and flavoring agents such as tomato juice, salt, pepper, parsley, celery, and the like to enhance the flavor thereof.

EXAMPLE 53

A therapeutic composition of sourdough bread made from flour, water, yeast, sourdough starter, and an additional oxalic acid ingredient selected from the group of dried chopped parsley, freeze-dried chives, oxalic acid, oxalate, foods containing oxalic acid, foods containing oxalate, vegetable juice such as carrot juice, or combinations thereof to provide approximately 2 g. of oxalic acid per 4 lb. Loaf of sourdough bread.

EXAMPLE 54

A method of therapeutically treating a patient having the steps of periodically administering a portion of the sourdough bread of Example 53 to provide a dosage of oxalic acid of up to about 1 g. oxalic acid per day.

EXAMPLE 55

A method of delaying, preventing, controlling, or treating the onset of Alzheimer's Disease lessening the effects of the disease, or improving the quality of life of a person suffering from the disease having the steps of periodically administering a therapeutically effective amount of at least one therapeutically effective form of oxalic acid or oxalate.

EXAMPLE 56

A method of treating or preventing oxalate nephrosis in patients including periodically administering a therapeutically effective amount of at least one oxalic acid or oxalate blocker.

EXAMPLE 57

A test kit for detecting the oxalate level in urine of patients having a sample holder and a liquid reagent which upon addition of a selected quantity of reagent to a sample of urine in the sample holder provides a colormetric indication of the presence or absence of oxalate.

EXAMPLE 58

The Relationship Between Oxalic Acid and Blockers

A Program For Tumor Reduction

Improved Dietary Procedure Plan

This Dietary Procedure Plan is drawn from research data in the United States patent application for Oxalic Acid or Oxalate Composition and Method of Treatment for Tumors. Oxalic acid is considered to be a natural chemotherapy in the reduction and prevention of tumor growth.

Certain vegetable such as carrots, carrot juice, spinach, parsley, chives, beets and beet leaves, garlic, collards, and radishes are high among vegetables containing oxalic acid and should be eaten or drank in order to build a high concentration of oxalic acid in the body fluids. Almonds, cashews, peanuts, walnuts, and many other nuts and seeds contain oxalic acid and may be eaten. Especially walnuts, which are high in oleic and linoleic fatty acids and increase oxalic acid absorption in the lower intestine, should be eaten. Coffee, tea, cocoa made with distilled water, and natural fruit juices are acceptable for drinking, especially cocoa which is very high in oxalic acid content. All beverages should be free of citric acid.

There are certain items in the normal diet that are blockers to absorption of oxalic acid which reduces the acid available in the system to treat vascular disorders, diseases and other conditions. These items are citric acid, calcium, pyridoxine (vitamin B6), alcohol, and in certain instances ascorbic acid (vitamin C), soda pop, thirst-quenchers, sport drinks and flavored drinking waters, should absolutely be avoided as they are high in citric acid. All dairy products must be avoided as calcium prevents absorption of oxalic acid, and when combined form calcium-oxalate kidney stones. All red meats, chicken and turkey breast (generally white meat) are high in pyridoxine (B6), and should be avoided. No alcohol should be consumed. Excessive intake of ascorbic acid should be avoided. It is absolutely necessary to read the ingredients on all food and drink items consumed while on the diet. Citric and ascorbic acids are widely used as a preservative in many products, including frozen and bakery goods.

As oxalic acid is built up in the system, one may experience indigestion known as heartburn or a nagging backache. These are indicators that the acid is being ingested in too large a quantity, or the system is absorbing the acid at a rate faster than it can be utilized. Indigestion or heartburn can be relieved by taking 2 or 3 teaspoonfuls of crushed pineapple. Relief for the backache can be accomplished by taking one (1) 100 mg B6 pill. You will learn a slight moderation of the diet will avoid either of the above conditions. Maximum effect of oxalic acid on tumor reduction would be accomplished if an acid level can be maintained just below the discomfort level. Research shows that 5 to 7 days after the start of the diet, an increase in energy may be experienced. Some people notice a body weight loss.

Improvement in condition of visible tumors may be noticed after 12 to 15 days. If there are multiple tumors, the newest tumors will regress first, and the core (first) tumor will require a longer diet time. Once tumors begin to shrink and disappear and when finally all trace of cancer has been cleared in the blood system, a balanced diet of all foods may be resumed while being sure to maintain an adequate level of oxalic acid in the system to prevent resumption of tumor growth.

The microwave should not be used for cooking or heating any foods or beverages in the diet because it reduces the strength of the acid. Also, do not use electric blankets, electric razors, and electric hair blower/dryers because strong electric fields can reduce the acid. Avoidance of excessive and/or extended use of a cellular phone should also be exercised.

This same procedure can be used to treat vascular disorders, diseases, and other conditions.

EXAMPLE 59

A dietary supplement for everyday optimum nutritional balance having between 0.5 to 1.5 g. of oxalic acid.

EXAMPLE 60

A test kit for detecting the presence and quantity of oxalic acid in a blood sample of a patient having a sample support surface, a reagent, and a mixing container for mixing together the blood sample and reagent to allow the reagent to undergo a color change and provide a colormetric determination of the presence and quantity of oxalic acid in the sample.

EXAMPLE 61

A method of treating patients including the steps of testing the blood or urine oxalic acid or oxalate levels, administering oxalic acid, oxalate or blockers thereof, and monitoring the levels to determine if adjustments are necessary to achieve a desired level.

EXAMPLE 62

A composition for controlling, treating or managing vascular disorders, diseases, and other conditions for preventing new swelling or enlargement of tissues, or for otherwise therapeutically treating patients and including at least one therapeutically effective form of oxalic acid or oxalate.

EXAMPLE 63

The composition as described in Example 62 wherein the therapeutically effective form of oxalic acid or oxalate is selected from the group of oxalic acid in a free acid, ester, lactone or salt form, oxalates including sodium oxalate, a nutritional supplement containing at least one form of oxalic acid or oxalate, oxalic acid dihydrate, anhydrous oxalic acid, oxamide, oxalate salts, natural or processed foods including molds, plants or vegetables including parsley, chives, garlic, beets, carrots, spinach, and the like containing at least one form of oxalic acid or oxalate, beverages, liquids or juices such as carrot juice containing at least one form of oxalic acid or oxalate, additives containing at least one form of oxalic acid or oxalate, and combinations thereof.

EXAMPLE 64

A method for controlling, treating or managing vascular disorders, diseases, and other conditions for preventing new swelling or enlargement of tissues, or for otherwise therapeutically treating patients having the steps of periodically administering a therapeutically effective dosage of the composition of Example 62

EXAMPLE 65

The method as described in Example 64 further having the steps of reducing the intake of oxalic acid or oxalate blockers.

EXAMPLE 66

A diet for treating, controlling, and preventing vascular disorders, diseases, and other conditions in patients having the steps of adding to the regular diet a dietary supplement of at least one therapeutically effective form of oxalic acid or oxalate.

EXAMPLE 67

The diet as described in Example 66 wherein the therapeutically effective form of oxalic acid or oxalate is selected from the group of oxalic acid in a free acid, ester, lactone or salt form, oxalates including sodium oxalate, a nutritional supplement containing at least one form of oxalic acid or oxalate, oxalic acid dihydrate, anhydrous oxalic acid, oxamide, oxalate salts, natural or processed foods including molds, plants or vegetables including parsley, chives, garlic, beets, carrots, spinach, and the like containing at least one form of oxalic acid or oxalate, beverages, liquids or juices such as carrot juice containing at least one form of oxalic acid or oxalate, additives containing at least one form of oxalic acid or oxalate, and combinations thereof.

EXAMPLE 68

The diet described in Example 66 further having the steps of reducing the intake of oxalic acid or oxalate blockers.

EXAMPLE 69

The diet as described in Example 68 wherein the blockers are selected from the group of citric acid, ascorbic acid, pyridoxine hydrochloride, calcium, alcohol, resins, clays, and combinations thereof.

EXAMPLE 70

The diet as described in Example 68 wherein the blockers are selected from the group of dairy products including calcium, fruits, coconut, beverages containing alcohol, ascorbic acid or citric acid including adult beverages such as beer, wine, vodka, gin, and the like, fruit juice based beverages, soda pop or soft drinks containing ascorbic acid or citric acid, other sports drinks, beverages containing alcohol, citric acid, ascorbic acid or pyridoxine hydrochloride including breads or grains, resins, and combinations thereof.

EXAMPLE 71

A veterinary composition for controlling, treating or managing vascular disorders, diseases, and other conditions, for preventing disease, or for otherwise therapeutically treating warm-blooded animals of a composition including at least one therapeutically effective form of oxalic acid or oxalate.

EXAMPLE 72

The veterinary composition as described in Example 71 wherein the therapeutically effective form of oxalic acid or oxalate is selected from the group of oxalic acid in a free acid, ester, lactone or salt form, oxalates including sodium oxalate, a nutritional supplement containing at least one form of oxalic acid or oxalate, oxalic acid dihydrate, anhydrous oxalic acid, oxamide, oxalate salts, natural or processed foods including molds, plants or vegetables including parsley, chives, garlic, beets, carrots, spinach, and the like containing at least one form of oxalic acid or oxalate, beverages, liquids or juices such as carrot juice containing at least one form of oxalic acid or oxalate, additives containing at least one form of oxalic acid or oxalate, and combinations thereof.

EXAMPLE 73

The veterinary composition as described in Example 72 wherein the composition is oxalic acid dihydrate.

EXAMPLE 74

The veterinary composition as described in Example 72 wherein the composition is at least one of carrots, boiled carrots, carrot juice, and dried parsley.

EXAMPLE 75

The veterinary composition as described in Example 72 further having a pharmaceutically acceptable carrier or diluent for the therapeutically effective form of oxalic acid or oxalate.

EXAMPLE 76

The veterinary composition as described in Example 75 wherein the carrier or diluent is a gel cap or distilled water.

EXAMPLE 77

A composition for counteracting the decomposition or reduction of oxalic acid or oxalate caused by radiation exposure, radiation treatment, X-rays, strong electromagnetic waves or fields, microwaves, and the like or for returning the body's oxalic acid or oxalate level to at least a normal level following radiation treatment, X-rays, CAT-scans, MRI-scans, and the like including a therapeutically effective amount of at least one therapeutically effective form of oxalic acid or oxalate.

EXAMPLE 78

A method for counteracting the decomposition or reduction of oxalic acid or oxalate caused by radiation exposure, radiation treatment, X-rays, strong electromagnetic waves or fields, microwaves, and the like or for returning the body's oxalic acid or oxalate level to at least a normal level following radiation treatment, X-rays, CAT-scans, MRI-scans, and the like having the steps of administering a therapeutically effective amount of the composition of Example 77 following the treatment or exposure.

EXAMPLE 79

The method as described in Example 78 further including the steps of administering a therapeutically effective amount of the composition of Example 77 prior to the treatment or exposure.

EXAMPLE 80

A method of enhancing the therapeutic effect of oxalic acid or oxalate including the steps of decreasing or eliminating the ingestion or administration of one or more of oxalic acid or oxalate blockers.

EXAMPLE 81

The method as described in Example 80 wherein the blockers are selected from the group of calcium, alcohol, citric acid, ascorbic acid, pyridoxine hydrochloride, resins, and combinations thereof.

EXAMPLE 82

A method of manufacturing a dry processed dog food containing at least one form of oxalic acid or oxalate including the steps of mixing a slurry of conventional dog food ingredients together with a dilute solution of oxalic acid or oxalate in heated water to form an oxalic acid or oxalate containing slurry, forming the slurry into pellets and drying the pellets.

EXAMPLE 83

The method as described in Example 82 wherein the oxalic acid is oxalic acid dihydrate and each pellet contains approximately 1 mg of oxalic acid so that one pound of dry dog food contains about 1 g of oxalic acid.

EXAMPLE 84

A dietary supplement for treating a patient diagnosed with vascular disorders, diseases, and other conditions having about 1 g to 6 g, preferably 2 g to 4 g of oxalic acid per day based on 70 kilograms of body weight and a pharmaceutically acceptable carrier or diluent.

EXAMPLE 85

A pharmaceutical composition to be administered orally to humans of a mixture of a non-toxic ingestible carrier and a therapeutically effective form of oxalic acid or oxalate.

EXAMPLE 86

The pharmaceutical composition as described in Example 85 wherein the composition is provided in a form selected from the group of pills, powders, granules, tablets, microcapsules, gel capsules, nutritional supplements, processed foods, liquids, juices, drops, beverages, additives and solutions.

EXAMPLE 87
Treatment For Vascular Disorders, Diseases, And Other Conditions

Our research indicates the following as a treatment for vascular disorders, diseases, and other conditions:

Carrots, carrot juice, spinach, parsley, chives, beets and beet leaves, garlic, collards and radishes are high among vegetables containing Oxalic Acid and should be eaten or drank in order to build a high concentration of acid in the body fluids. Almonds, cashews, peanuts, and, especially walnuts which are high in oleic and linoleic fatty acids and increase oxalic acid absorption may be eaten.

Red meats, chicken and turkey breasts, (generally white meat) are considered high in Pyridoxine (Vitamin B6), and should be avoided during the treatment. Alcohol and products containing citric acid (soda pop, other soft drinks, and thirst quenchers are generally high in citric acid), and ascorbic acid (Vitamin C) are considered blockers of oxalic acid and should be avoided since they retard the build up of oxalic acid in the system. It is absolutely necessary to read the ingredients on all food and drinks consumed while on the treatment Citric and ascorbic acids are widely used as a preservative in many products, including frozen and bakery goods.

All dairy products should also be avoided while following the treatment. Calcium inhibits oxalic acid and when combined can form calcium oxalate stones (kidney).

Coffee, cocoa, regular tea made with distilled water, and natural fruit juices are acceptable for drinking. All beverages should be free of citric acid.

As oxalic acid is built up in the system one may experience indigestion known as heartburn or a nagging backache. These indicate that the acid is being ingested in too large a quantity or the system is digesting the acid at a rate faster than it can be absorbed. Indigestion can be relieved by taking 2 or 3 teaspoons of crushed pineapple. Relief for the backache can be accomplished by taking one (1) 100 mg Vitamin B6 pill. A slight reduction of the intake of oxalic acid will avoid either of the above conditions. Maximum effect of vascular disorders, diseases, and other conditions treatment would be accomplished if an acid level can be maintained just below the discomfort level.

Our research shows that five to seven days after the start of the treatment, an increase in energy will be experienced. Some people notice a body weight loss.

The microwave oven should not be used for cooking or heating any foods or beverages in the diet because it reduces the strength or amount of the oxalic acid.

EXAMPLE 88

A method of counteracting the deleterious effects of a mammogram, CAT-scan, X-ray, and the like, exposure or treatment including the steps of about 3 weeks prior to the exposure increasing the intake of oxalic acid or oxalate, continuing the increased oxalic acid or oxalate during the treatment and for 3 weeks following treatment Thereafter, checking the blood or urine oxalic acid or oxalate levels of the patient and if they are normal, continuing with that level of intake of oxalic acid or oxalate, if they are above normal, reducing the intake of oxalic acid or oxalate, and if they are below normal, increasing the intake of oxalic acid or oxalate. Thereafter, monitoring the levels and adjusting the intake on a periodic basis.

EXAMPLE 89

An oxalic acid or oxalate containing bread including about 1 gram of oxalic acid or oxalate per loaf of bread.

EXAMPLE 90

The bread of Example 89 wherein the oxalic acid is oxalic acid dihydrate dissolved in distilled water prior to being added to the bread during manufacturing of the loaf.

EXAMPLE 91

The bread of Example 90 further containing about 2 cups of trail mix including nuts, dried fruits, and the like, per loaf of bread with the trail mix being added during the manufacture of the loaf.

EXAMPLE 92

A dry dogfood is prepared with 300 lbs. Of dry dogfood having added thereto 10 ½ ounces of oxalic acid dihydrate to provide about 1 gram of oxalic acid per pound of dry dogfood. The oxalic acid dihydrate powder is added to 90 degree Celsius distilled water and mixed into the conventional dogfood slurry.

EXAMPLE 93

The dogfood of Example 92 with the exception that any Vitamin B6 is removed from the conventional dry mix.

EXAMPLE 94

An oxalic acid intake adult management control plan includes four phases. In the first phase, the adult is administered about 1 ¾ to 2 grams of oxalic acid or oxalate per day, for 5 to 7 days to cleanse the blood of the patient for a 70-kilogram weight adult. For larger adults, the dosage would have to be increased. Also, oxalic acid and oxalate levels are checked in the blood, plasma and/or urine to determine the exact amount of oxalic acid or oxalate required for the individual subject. In the second phase of the treatment, the subject is given about ¾ gram of oxalic acid or oxalate for an additional 15 to 20 days until the vascular disorder, disease or other condition shows improvement by change in blood pressure and/or laboratory tests. In the third phase the subject is given about ½ gram of oxalic acid or oxalate per day to continue correction of the vascular disorder, disease, or other condition, or until the disease is eliminated. In the fourth phase or maintenance phase, the subject is given about 50 mg of oxalic acid or oxalate per day for maintenance of good health. Again, these dosages are provided for an average 70-kilogram adult and the individual's oxalic acid or oxalate levels need to be checked periodically and the dosages adjusted as necessary.

EXAMPLE 95

The control plan of Example 94 wherein a computer model of the chemical balance of the human body is used in addition to the oxalic acid and oxalate level information to determine the proper dosage for that individual.

EXAMPLE 96

A method of enhancing the beneficial effects of oxalic acid or oxalate in patients including the steps of eliminating the use of microwave cooking for heating food or drink of the patient to prevent the decomposition or reduction in the amount of oxalic acid or oxalate in their food or drink.

EXAMPLE 97

The method of Example 96 further including the step of eliminating the use of the microwave oven for cooking or heating to prevent exposure to microwaves and thereby prevent decomposition or reduction in oxalic acid or oxalate in the patient being exposed.

EXAMPLE 98

The method of Example 97 further including the steps of eliminating the use of radiation, X-ray, CAT-scan, mammogram, strong electromagnetic waves, excessive heat, or other exposures or treatments which would decompose or reduce the amount of oxalic acid or oxalate in the patient.

EXAMPLE 99

A mouthwash containing a dilute solution of oxalic acid and having a pH of about 2.3.

EXAMPLE 100

An oxalic acid or oxalate containing drink including carrot juice have a pH of about 5.5.

EXAMPLE 101

A mouthwash or oral rinse containing a dilute solution of 500 milligrams or less of oxalic acid dihydrate per 500 milliliters of distilled water.

EXAMPLE 102

A method of treating terminally ill patients including the steps of administering a high dosage of oxalic acid or oxalate to cleanse the blood and treat the vascular disorder, disease, or other condition.

EXAMPLE 103

The method of Example 102 further including the steps of stopping conventional oncological chemotherapy treatments to prevent the weakening of the body and prevent the decomposition or reduction of oxalic acid or oxalate in the body.

EXAMPLE 104

The method of Example 102 further including the steps of reducing the dosage of oxalic acid or oxalate after the blood has been cleansed and the vascular disorder, disease, or other condition has improved.

EXAMPLE 105

The method of Examples 102, 103, or 104 further including the step of reducing the intake of oxalic acid or oxalate blockers and increasing the intake of oxalic acid or oxalate enhancers.

TABLE I

Oxalic Acid Content of Selected Vegetables

| Vegetable | Oxalic Acid (g/100 g) |
|---|---|
| Amaranth | 1.09 |
| Asparagus | .13 |
| Beans, snap | .36 |
| Beet leaves | .61 |
| Broccoli | .19 |
| Brussels sprouts | .36 |
| Cabbage | .10 |
| Carrot | .50 |
| Cassava | 1.26 |
| Cauliflower | .15 |
| Celery | .19 |
| Chicory | .21 |
| Chives | 1.48 |
| Collards | .45 |
| Coriander | .01 |
| Corn, sweet | .01 |
| Cucumbers | .02 |
| Eggplant | .19 |
| Endive | .11 |
| Garlic | .36 |
| Kale | .02 |
| Lettuce | .33 |
| Okra | .05 |
| Onion | .05 |
| Parsley | 1.70 |
| Parsnip | .04 |
| Pea | .05 |
| Pepper | .04 |
| Potato | .05 |
| Purslane | 1.31 |
| Radish | .48 |
| Rutabaga | .03 |
| Spinach | .97 |
| Squash | .02 |
| Sweetpotato | .24 |
| Tomato | .05 |
| Turnip | .21 |
| Turnip greens | .05 |
| Watercress | .31 |

TABLE II

Oxalic Acid Contents of Foods

| Food | Method of Preparation | Oxalic acid[a] (mg/100 g of fresh material) |
|---|---|---|
| Vegetables | | |
| Asparagus | Fresh | 1.7 |
| Bean, runner | Boiled | 7.2–61.8 |
| Beet root | Boiled | 96.8–121.0 |
| Brussels sprouts | Boiled | 2.1–3.6 |
| Cabbage | Boiled | 0.6–2.0 |
| Carrot | Boiled | 7.4–22.7 |
| Cauliflower | Boiled | 1.1 |
| Celery | Fresh | 13.0–17.5 |
| Chive | Fresh | 1.1 |
| Lettuce | Fresh | 1.7–2.7 |
| Marrow | Fresh | 0.5 |
| Mushroom | Fresh | 2.0 |
| Onion | Boiled | 3.0 |
| Parsley | Fresh | 166.0 |
| Pea, green | Boiled | 0.8–1.3 |
| Potato | Boiled | 2.3–7.1 |
| Radish | Fresh | 0.3 |
| Rhubarb | Stewed | 260–620 |
| Spinach | Boiled | 356–780 |
| Tomato | Fresh | 5.3 |
| Turnip | Boiled | 0.8 |
| Fruit | | |
| Apple | Fresh | 1.5 |
| Apricot | Fresh | 2.8 |
| Banana, ripe | Fresh | 0.7 |
| Gooseberry | Stewed | 2.6 |
| Grapefruit | Fresh | 0.0–6.6 |
| Melon | Fresh | 2.7 |
| Orange | Fresh | 6.2 |
| Peach | Canned | 1.2–3.7 |
| Pear | Canned | 1.3–1.7 |
| Pineapple | Canned | 0.0–3.7 |
| Plum | Stewed | 1.1–3.4 |
| Raspberry | Fresh | 2.2 |
| Strawberry | Fresh | 1.9–11.5 |
| Preserves | | |
| Jam, red plum | — | 0.5 |
| Jam, strawberry | — | 9.4 |
| Marmalade | — | 4.5–10.8 |
| Meat | | |
| Bacon, streaky | Fried | 0.6–3.3 |
| Beef | Roasted | 0.2 |
| Beef, corned | Fresh | 0.2 |
| Chicken | Roasted | 0.3–1.9 |
| Ham | Steamed | 0.4–1.6 |
| Kidney | Braised | 1.6–5.1 |
| Liver | Braised | 3.6–7.1 |
| Mutton | Roasted | 1.6 |
| Pork | Roasted | 1.7 |
| Soups | | |
| Chicken (Fray Bentos) | Heated | 3.0 |
| Oxtail (Fray Bentos) | Heated | 1.0 |
| Dairy products | | |
| Butter | Fresh | 0.0 |
| Cheese, Cheshire | Fresh | 0.0 |
| Eggs, whole | Boiled | 0.0–0.9 |
| Margarine | Fresh | 0.0 |
| Milk, cow | Fresh | 0.5–0.9 |
| Fish | | |
| Haddock | Boiled | 0.2 |
| Plaice | Boiled | 0.3 |
| Sardines | Canned | 1.6–4.8 |
| Cereals | | |
| Biscuits (Marie) | — | 4.5–13.8 |
| Bread, white | Fresh | 4.9–8.6 |
| Bread, Allinson's | Fresh | 15.8–26.3 |
| Cake, fruit | — | 11.8 |
| Cake, sponge | — | 7.4 |
| Cornflakes | — | 4.4–5.6 |
| Corn cob | Fresh | 9.1 |
| Oatmeal porridge | Cooked | 1.0 |
| Rice pudding | Cooked | 0.0 |
| Chocolate | | |
| Cadbury's plain | — | 123.5 |
| Cadbury's milk | — | 56.2 |
| Beverages | | |
| Beer, mild | Draught | 0.9–1.6 |
| Beer, bitter | Draught | 0.9–1.9 |
| Beer (Double Diamond) | Draught | 0.8 |
| Beer (Double Diamond) | Bottled | 1.9–2.0 |
| Beer (Guinness) | Draught | 1.4 |
| Beer (Guinness) | Bottled | 2.8–3.9 |
| Cocoa (Rowntree's) | Powder | 623.0 |
| Coca Cola | Canned | 1.12 |
| Coffee, infusion | 2 g per 100 ml, infused 5 min. | 1.0 |
| | 4.4 g per 100 ml, infused 13 min. | 7.3 |
| Coffee essence (Camp) | Undiluted | 9.0 |
| Coffee (Nescafe) | Powder | 57.0–230.0 |
| Dandelion coffee | Powder | 25.0 |
| Horlicks | Powder | 4.1 |
| Lager (Skol) | Draught | 0.6 |
| Lemon squash (Robertson's) | — | 1.5 |
| Lucozade | — | 0.1 |
| Orange squash (Robertson's) | — | 1.2 |
| Ovaltine | Powder | 45.9 |
| Oxo cubes | — | 1.6 |
| Tea, leaves | Fresh, dried | 375–1,450 |
| Tea, infusion | 1 g per 100 ml, infused 2 min. | 4.6 |
| | 2.0 g per 100 ml, infused 2 min. | 7.0–10.8 |
| | 2.0 g per 100 ml, infused 5 min. | 10.1–14.5 |
| | 2.0 g per 100 ml, infused 10 min. | 11.5–16.1 |
| | 2.0 g per 100 ml, infused 15 min. | 12.6–17.2 |
| Wine, Beaujolais | — | 3.1 |

[a]Expressed as the anhydrous acid $(COOH)_2$.
From Oxalic Acid in Biology and Medicine, Pgs.196–199.

TABLE III

Oxalate Content of Foods per 100 GM. EDIBLE PORTION

| FOOD | OXALATE mg. |
|---|---|
| Cereal and Cereal Products | |
| Bread, white | 4.9 |
| Cake, fruit | 11.8 |
| Cake, sponge | 7.4 |
| Cornflakes | 2.0 |
| Crackers, soybean | 207.0 |
| Egg noodle (chow mein) | 1.0 |
| Grits (white corn) | 41.0 |
| Macaroni, boiled | 1.0 |
| Oatmeal, porridge | 1.0 |
| Spaghetti, boiled | 1.5 |

TABLE III-continued

Oxalate Content of Foods per 100 GM. EDIBLE PORTION

| FOOD | OXALATE mg. |
|---|---|
| Spaghetti in tomato sauce | 4.0 |
| Wheat germ | 269.0 |
| Milk and Milk Products | |
| Butter | 0.0 |
| Cheese, cheddar | 0.0 |
| Margarine | 0.0 |
| Milk | 0.15 |
| Meats and Eggs | |
| Bacon, streaky fried | 3.3 |
| Beef, canned corned | 0.0 |
| Beef, topside roast | 0.0 |
| Chicken, roast | 0.0 |
| Eggs, boiled | 0.0 |
| Fish: | |
|    Haddock | 0.2 |
|    Plaice | 0.3 |
|    Sardines | 4.8 |
| Ham | 1.6 |
| Hamburger, grilled | 0.0 |
| Lamb, roast | trace |
| Liver | 7.1 |
| Pork, roast | 1.7 |
| Vegetables | |
| Asparagus | 5.2 |
| Beans, green boiled | 15.0 |
| Beans in tomato sauce | 19.0 |
| Beet root, boiled | 675.0 |
| Beet root, pickled | 500.0 |
| Broccoli, boiled | trace |
| Brussels sprouts, boiled | 0.0 |
| Cabbage, boiled | 0.0 |
| Carrots, canned | 4.0 |
| Cauliflower, boiled | 1.0 |
| Celery | 20.0 |
| Chard, Swiss | 645.0 |
| Chive | 1.1 |
| Collards | 74.0 |
| Corn, yellow | 5.2 |
| Cucumber, raw | 1.0 |
| Dandelion greens | 24.6 |
| Eggplant | 18.0 |
| Escarole | 31.0 |
| Kale | 13.0 |
| Leek | 89.0 |
| Lettuce | 3.0 |
| Lima beans | 4.3 |
| Mushrooms | 2.0 |
| Mustard greens | 7.7 |
| Okra | 146.0 |
| Onion, boiled | 3.0 |
| Parsley, raw | 100.0 |
| Parsnips | 10.0 |
| Peas, canned | 1.0 |
| Pepper, green | 16.0 |
| Pokeweed | 476.0 |
| Potatoes, white boiled | 0.0 |
| Potatoes, sweet | 56.0 |
| Radishes | 0.3 |
| Rice, boiled | 0.0 |
| Rutabagas | 19.0 |
| Spinach, boiled | 750.0 |
| Spinach, frozen | 600.0 |
| Squash, summer | 22.0 |
| Tomatoes, raw | 2.0 |
| Turnips, boiled | 1.0 |
| Watercress, early fine curled | 10.0 |
| Fruits | |
| Apples, raw | 3.0 |
| Apricots | 2.8 |
| Avocado | 0.0 |
| Banana, raw | trace |
| Berries: | |
|    Black | 18.0 |
|    Blue | 15.0 |
|    Dew | 14.0 |
|    Green goose | 88.0 |
|    Raspberries, black | 53.0 |
|    Raspberries, red | 15.0 |
|    Strawberries, canned | 15.0 |
|    Strawberries, raw | 10.0 |
| Cherries: | |
|    Bing | 0.0 |
|    Sour | 1.1 |
| Currants: | |
|    Black | 4.3 |
|    Red | 19.0 |
| Fruit salad, canned | 12.0 |
| Grapes: | |
|    Concord | 25.0 |
|    Thompson, seedless | 0.0 |
| Lemon Peel | 83.0 |
| Lime Peel | 110.0 |
| Mangoes | 0.0 |
| Melons: | |
|    Cantaloupe | 0.0 |
|    Casaba | 0.0 |
|    Honeydew | 0.0 |
|    Watermelon | 0.0 |
| Nectarines | 0.0 |
| Orange, raw | 4.0 |
| Peaches: | |
|    Alberta | 5.0 |
|    canned | 1.2 |
|    Hiley | 0.0 |
|    Stokes | 1.2 |
| Pears: | 3.0 |
|    Bartlett, canned | 1.7 |
| Pineapple, canned | 1.0 |
| Plums: | |
|    Damson | 10.0 |
|    Golden gage | 1.1 |
|    Green gage | 0.0 |
| Preserves: | |
|    Red plum jam | 0.5 |
|    Strawberry jam | 9.4 |
| Prunes, Italian | 5.8 |
| Rhubarb: | |
|    canned | 800.0 |
|    stewed, no sugar | 860.0 |
| Nuts | |
| Peanuts, roasted | 187.0 |
| Pecans | 202.0 |
| Confectionery | |
| Chocolate, plain | 117.0 |
| Jelly, with allowed fruit | 0.0 |
| Marmalade | 10.8 |
| Sweets, boiled (plain candies) | 0.0 |
| Beverages, Non-alcoholic | |
| Barley water, bottled | 0.0 |
| Coca-Cola | trace |
| Coffee (0.5 g Nescafe/100 ml) | 3.2 |
| Lemon Squash drink (lemonade) | 1.0 |
| Lucozade, bottled (soda) | 0.0 |
| Orange Squash drink (orangeade) | 2.5 |
| Ovaltine drink, 2 gm in 100 ml | 10.0 |
| Pepsi-Coia | trace |
| Ribena, concentrate (black currant drink) | 2.0 |
| Tea, Indian: | |
|    2 min.intusicn | 55.0 |
|    4 min.infusion | 72.0 |

TABLE III-continued

Oxalate Content of Foods per 100 GM. EDIBLE PORTION

| FOOD | OXALATE mg. |
|---|---|
| 6 min.infusion | 78.0 |
| Tea, rosehip | 4.0 |
| Juices | |
| Apple juice | trace |
| Cranberry juice | 6.6 |
| Grape juice | 5.8 |
| Grapefruit juice | 0.0 |
| Orange juice | 0.5 |
| Pineapple juice | 0.0 |
| Tomato juice | 5.0 |
| Beverages, alcoholic | |
| Beer: | |
|   bottled | 0.0 |
|   draft | 1.0 |
|   Lager draft, Tuborg Pilsner | 4.0 |
|   Stout, Guiness Draft | 2.0 |
| Cider | 0.0 |
| Sherry, dry | trace |
| Wine: | |
|   Port | trace |
|   Rose | 1.5 |
|   White | 0.0 |
| Miscellaneous | |
| Cocoa, dry powder | 623.0 |
| Coffee powder (Nescafe) | 33.0 |
| Chicken noodle soup | 1.0 |
| Lemon juice | 1.0 |
| Lime juice | 0.0 |
| Ovaltine, powder canned | 35.0 |
| Oxtail soup | 1.0 |
| Pepper | 419.0 |
| Tomato soup | 3.0 |
| Vegetable soup | 5.0 |

From: Krause & Mahen, Food, Nutritient Diet Therapy, 7th ed., 1984, W. B. Saunders, Phila.

TABLE IV

Concentrations of oxalic acid, calcium and magnesium in foods

| Food | Oxalic Acid (mmol/kg fresh wt) | Calcium (mmol/kg fresh wt) | Magnesiutn (mmol/kg fresh wt) |
|---|---|---|---|
| Vegetables | | | |
| Cabbage | 0.11 | 16.2 | 8.5 |
| Cauliflower | 0.12 | 5.9 | 6.4 |
| Onion | 0.33 | 7.1 | 4.8 |
| Potato | 0.25 | 2.2 | — |
| Lettuce | 0.19 | 6.5 | 4.1 |
| Rhubarb | 28.9 | 3.1 | 4.0 |
| Beet root | 13.5 | 4.7 | 15.5 |
| Spinach | 86.6 | 27.7 | 31.6 |
| Fruit | | | |
| Apple | 0.17 | 0.85 | 2.05 |
| Orange | 0.69 | 0.87 | 5.70 |
| Pear | 0.19 | 1.0 | 1.85 |
| Plum | 0.38 | 3.57 | 3.33 |
| Strawberry | 0.21 | 4.10 | 4.73 |
| Tomato | 0.59 | 2.50 | 4.11 |
| Meat, fish and dairy products | | | |
| Beef, roasted | 0.04 | 1.92 | 11.7 |
| Fish (haddock) | 0.02 | 4.22 | 11.6 |
| Milk (cow) | 0.005 | 28.7 | 4.3 |
| Cereals | | | |
| Bread, white | 0.54 | 27.0 | 10.0 |
| Cornflakes | 0.62 | 2.2 | 14.8 |
| Beverayes | | | |
| Ovaltine, powder | 5.1 | 31.5 | 13.6 |
| Tea (1 g/100 ml, infused for 2 min) | 0.51 | 0.07 | 0.25 |
| Tea (1.5 g/100 ml, infused for 6 min) | 0.92 | 0.13 | 1.03 |

Zarembski and Hodgkinson (1962b).

TABLE V

Dietary intake of oxalate by man and animals

| | Oxalic acid (anhydrous) mg/kg day | | | | |
|---|---|---|---|---|---|
| Description | Mean | Range | Mean | Range | Reference |
| Man | | | | | |
| British | 920 | 850–980 | 12.3 | 10.1–13.6 | Archer et al. (1957a) |
| British | 97 | 70–150 | 1.4 | 1.0–2.1 | Zarembski and Hodgkinson (1962b) |
| British | — | 145–175 | — | — | Anderson et al. (1971) |
| Indian on hospital diet | 139.4 | — | — | — | Singh et al. (1972) |
| Indian on common rural diet | 77.8 | — | — | — | Singh et al. (1972) |
| Indian on seasonal rural diet | 2045.0 | — | — | — | Singh et al. (1972) |

TABLE V-continued

Dietary intake of oxalate by man and animals

| | Oxalic acid (anhydrous) mg/kg day | | | | |
|---|---|---|---|---|---|
| Description | Mean | Range | Mean | Range | Reference |
| Indian on urban diet, lower income group | 168.5 | — | — | — | Singh et al. (1972) |
| Indian on urban diet, upper income group | 606.4 | — | — | — | Singh et al. (1972) |
| Indian from Kashmir | — | 260–450 | — | — | Dhar and Kaul (1973) |
| Sheep | — | 2160–5000 | — | 31.7–73.5 | Brune (1955) |
| Cow (Heifer) | — | 60700 | — | 243–286 | Talapatra et al. (1942) |
| Rat | — | 71500 | — | | Talapatra et al. (1942) |
| Wistar (300 g) | — | 14–28 | — | 46–92 | Hodgkinson (unpublished results) |
| Sand rat (200 g) | — | 300–500 | — | 1500–2500 | Shirley and Schmidt-Nielsen (1967) |

*Oxalic Acid in Biology and Medicine, pg. 160.

TABLE VI

Some recent estimates of the concentration of oxalic acid in human and aniinal blood

| | Oxalic acid ($\mu$g anhydrous acid/100 ml) | | |
|---|---|---|---|
| Analytical method | Mean | Range | Reference |
| Man | | | |
| Fluorimetry | 146.0 | 100–235[a] | Hodgkinson and Zarembski (1968) |
| | 169.0 | 127–254[c] | |
| Fluorimetry | 256.0 | 150–480[a] | Endo (1969) |
| Chemical kinetics | 124.0[b] | | Eswara-Dutt and Mottola (1974) |
| Enzymic Decarboxylation | 118.0 | 80–140[b] | Knowles and Hodgkinson (1972) |
| Enzymic decarboxylation | 130.4 | 73–199[b,d] | Hatch et al. (1977) |
| | 261.1 | 136–465[b,e] | |
| Ion exchange and colorimetry | – | 117–250[a] | Krugers Dagneaux et al. (1976) |
| [$^{14}$C]oxalic acid | 16.5 | — | Williams et al. (1971) |
| [$^{14}$C]oxalic acid | 13.0 | 11.8–14.3[a] | Hodgkinson and Wilkinson (1974) |
| Sheep | | | |
| [$^{14}$C]oxalic acid | – | 52.6–74.4[a] | McIntosh and Belling (1975) |

*Oxalic Acid In Biology and Medicine, pg. 174.
[a]Plasma
[b]Serum
[c]Whole blood
[d]Male
[e]Female

TABLE VII

Vitamin B-6 (Pyridoxine) Content of Pork and Pork Products

| Pork | Raw | Cooked Broiled/Braised | Cooked Roasted | Cooked Pan Fried |
|---|---|---|---|---|
| Composite of Retail Cuts All Lean and Fat | .445 | .394 | | |
| Leg, Loin & Shoulder Composite of Retail Cuts All Lean and Fat | .508 | .434 | | |
| Leg (Ham) Whole Lean and Fat | .401 | .402 | | |
| Leg (Ham) Whole Lean Only | .500 | .400 | | |

TABLE VII-continued

Vitamin B-6 (Pyridoxine) Content of Pork and Pork Products

| Pork | Raw | Cooked Broiled/Braised | Cooked Roasted | Cooked Pan Fried |
|---|---|---|---|---|
| Loin Whole Lean and Fat | .472 | .460 | .382 | |
| Loin Whole Lean Only | .527 | .492 | .404 | |
| Back Ribs Lean and Fat | .395 | | .307 | |
| Loin Chops Lean and Fat | .370 | .297 (braised) .381 (broiled) | | .337 |
| Bacon Cured | .14 | .27 | | |
| Canadian Style, Bacon Unheated | .38 (unheated) | .45 | | |
| Ham, Boneless Extra Lean & Regular | .38 (unheated) | | .35 | |
| Ham, Boneless (11% Fat) Extra Lean and Regular | .34 (unheated) | | .31 | |

Source: U.S. Department of Agriculture
Agriculture Handbook 8–10 Rev. 1992

TABLE VIII

Vitamin B-6 (Pyridoxine) Content of Beef and Beef Products

| | All Grades | | Good | | Choice | | Prime | |
|---|---|---|---|---|---|---|---|---|
| Beef | Raw | Cooked | Raw | Cooked | Raw | Cooked | Raw | Choice |
| Composite Retail Cuts Lean and Fat | .36 | .31 | .37 | .32 | .36 | .31 | .34 | .29 |
| Composite Retail Cuts Lean Only | .43 | .38 | .44 | .38 | .43 | .38 | .43 | .38 |

| Beef | Raw | Roasted | Broiled |
|---|---|---|---|
| Large Ribs Lean and Fat | .28 | .22 | .26 |
| Rib-Eye Small Ribs Lean and Fat | .38 | .32 | .36 |
| Whole Prime Ribs Lean and Fat | .30 | .25 | .29 |

| Beef | Mg/100 Grams |
|---|---|
| Beef Cured Frankfurter | .12 |
| Lebanon Bologna | .24 |
| Pastrami | .18 |
| Sausage Cooked and Smoked | .11 |
| Beef Cured and Corned | .13 |
| Liver Pan Fried | 1.43 |
| Kidney Cooked | .52 |
| Ground Lean Fried | .28 |
| Ground Lean Baked | .20 |

Source: U.S Department of Agriculture
Agriculture Handbook 8–13 1986

TABLE IX

Vitamin B-6 (Pyridoxine) Content of Veal and Lamb

| Meat | Raw | Cooked |
|---|---|---|
| Veal All Retail Cuts Lean and Fat | .41 | .31 |
| Lamb All Retail Cuts Lean and Fat | .13 | .13 |
| Lamb All Retail Cuts Lean | .16 | .16 |

Source: USDA Department of Agriculture Agriculture Handbook 8-17-1989

TABLE X

VITAMIN B-6 (PYRIDOXINE) CONTENT OF CHICKEN

| Chicken | Raw | Fried Batter-Dipped | Fried Flour Dipped | Roasted | Stewed |
|---|---|---|---|---|---|
| Broilers or Fryers All Meat with Skin | .34 | .32 | .42 | .38 | .22 |
| Broilers or Fryers All Meat Flesh Only | .43 | .48 | .53 | .47 | .26 |
| Broilers or Fryers Light Meat with Skin | .48 | .39 | .54 | .52 | .27 |
| Broilers or Fryers Light Meat Flesh Only | .54 | .63 | .65 | .60 | .26 |
| Broilers and Fryers Dark Meat with Skin | .25 | .25 | .32 | .31 | .17 |
| Broiler and Fryers Thigh with Skin | .26 | .26 | .33 | .31 | .17 |
| Broiler and Fryers Leg with Skin | .29 | .27 | .34 | .33 | .18 |
| Ground Turkey | .35 | .39 (Cooked) | | | |

Source: U.S. Department of Agriculture
Agriculture Handbook 8-5-1976

TABLE XI

VITAMIN B-6 (PYRIDOXINE) CONTENT OF SELECTED BAKED GOODS

| Breads | Mg/100 G |
|---|---|
| Bagels: Plain, Onion, Poppy Seed, Sesame | .051 |
| Bagels, Date Bran | .000 |
| Bagels, Egg | .084 |
| Bagels, Cinnamon Raisin | .000 |
| Biscuits, Commercially Baked Plain or Buttermilk | .047 |
| Cornbread | .113 |
| Cracked Wheat Bread | .304 |
| French and Vienna Bread | .043 |
| Italian Bread | .048 |
| Mixed Grains 7 Bread | .333 |
| Oat Bran Bread | .000 |
| Pumpernickel | .126 |
| Rye Bread | .075 |
| Wheat Bran Bread | .064 |
| Whole Wheat Commercial Bread | .179 |

Source: U.S. Department of Agriculture Agriculture Handbook 8–18 Rev 1992

TABLE XII

Dry Dog Food, Test Run Data

| E325 Processing Conditions: | Run #1 | Comment |
|---|---|---|
| Product | Dry Dog Food | |
| Feeder Speed (RPM) | 11 rpm (420 lbs/hr) | |
| Feeder Speed (Hertz) | 34.7 | |
| Cond. Cyl. Temp (° F.) | 206 | |
| Cond. Cyl. Water (% gauge) | 10 | |
| Extruder Speed (RPM) | 421 | |
| Extruder Current (Amps) | 24 | |
| Extruder Water (% gauge) | 0 | |
| Extruder Steam Injection | 0 | |
| #2 Head Temp. (CW or ST) | CW | |
| #3 Head Temp. (CW or ST) | CW | |
| #4 Head Temp. (CW or ST) | CW | |
| #5 Head Temp. (° F.) | CW 79 deg F | |
| #6 Head Temp. (° F.) | CW 129 deg F | |
| Die Pressure (PSI) | 350 | |
| Knife Speed (Hertz) | 55.9 | |

TABLE XII-continued

Dry Dog Food, Test Run Data

| E325 Processing Conditions: | Run #1 | Comment |
|---|---|---|
| Dryer Temperature (° F.) | 223 | |
| Dryer Retention (minutes) | 17.9 | |
| Formula: | See Dry Feed formula | 2.7# OA to 100# water |
| Comments: | 2.2% Oxalic acid solution added at 0.7 lbs/min | |
| | The oxalic acid solution was made up in hot water (160° F.) and pumped into the conditioning cylinder | |
| Screw Configuration: | | |
| #1 Screw | Single Flight Tapered Inlet | Straight Rib Head |
| #1 Steamlock | Spacer | |
| #2 Screw | Single Flight Uncut | Spiral Rib Head |
| #2 Steamlock | Spacer | |
| #3 Screw | Single Flight Uncut | Spiral Rib Head |
| #3 Steamlock | Spacer | |
| #4 Screw | Single to Double Flight Uncut | Straight Rib Head |
| #4 Steamlock | Small | |
| #5 Screw | 2 Flight cut flight | Straight Rib Head |
| #5 Steamlock | Large | |
| #6 Screw | 2 Flight cut flight cone | Spiral Rib Cone Head |
| Die Configuration: | | |
| Spacer | 1" thick | |
| Backup Die | No | |
| Dieplate | 1 ¼" central insert die | #825440-3 |
| Insert | ¼" round hole | #101-509 |

I claim:

1. A hemotherapeutic chemopreventative composition for treating vascular diseases of at least one of arteriosclerosis; atheroslerosis; endocarditis, treating plaque, fatty buildup, microbial infections, and calcerous conditions, in the cardiovascular system, or the brain, and maintaining good cardiovascular health in patients sensitive to treatment comprising a composition having an effective amount of at least one therapeutically effective form of at least one of oxalic acid and oxalate and at least one of a carrier and diluent for said at least one of oxalic acid and oxalate, wherein said effective amount is less than a lethal dosage of oxalic acid and oxalate wherein said hemotherapeutic composition is adapted to be administered to patients on a periodic basis in less than a lethal dosage.

2. The composition as recited in claim 1 wherein said therapeutically effective form of at least one of oxalic acid and oxalate is selected from the group of oxalic acid in a free acid, ester, lactone, and salt form.

3. The composition as recited in claim 1 wherein said therapeutically effective form of at least one of oxalic acid and oxalate is selected from the group of natural foods, processed foods, molds, plants, vegetables and beverages, juices, and liquids containing an effective amount of at least one therapeutically effective form of at least one of oxalic acid and oxalate.

4. The composition as recited in claim 1 wherein said therapeutically effective oxalic acid, oxalate composition is selected from a natural food or beverage source of at least one of oxalic acid, and oxalate.

5. The hemotherapeutic composition as recited in claim 1, wherein said composition is oxalic acid dehydrate and at least one of a carrier and diluent.

6. The hemotherapeutic composition for treating vascular disease, fatty buildup, microbial infections, and calcerous conditions as recited in claim 1 wherein said at least one of distilled water, saline solution, gel cap, tablet, powder, drops, liquid, pill, capsule, lozenge, cough drops, transdermal patch, rinse, mouthwash, food additive, beverage, and gel for periodically administering a therapeutically effective dosage of at least one of topically, orally, nasally, parenteral, intravenously, and subcutaneously in less than a lethal dosage.

7. The method of producing the hemotherapeutic composition as recited in claim 5 comprising the steps of mixing at least one therapeutically effective form of oxalic acid wherein said acid is oxalic acid dihydrate which is dissolved in distilled water to produce at least one of a mixture of a mixture, solution, rinse, mouthwash, mouth rinse, and wash adapted for periodically administering a hemotherapeutically effective dosage of at least one of topically, orally, nasally, parenterally, intravenously and subcutaneously in less than a lethal dosage.

8. A method of treating vascular diseases, plaque, microbial infections, fatty buildup, and calcification in patients sensitive to treatment comprising the steps of periodically administering a therapeutically effective dosage of the hemotherapeutic composition of claim 1.

9. The method as recited in claim 8 wherein said hemotherapeutic composition is administered by at least one of orally and sublingually.

10. The method as recited in claim 8 wherein said hemotherapeutic composition is administered by injection.

11. The method as recited in claim 8 wherein said hemotherapeutic composition is administered topically.

12. The method as recited in claim 8 wherein said hemotherapeutic composition is administered internally.

13. The method as recited in claim 8 wherein said hemotherapeutic composition is administered at least once a day at a dosage of at least one of up to 8 grams for humans and up to 4 grams for warm blooded animals other than humans.

14. A method for treating diseases of the vascular system, and the brain in patients sensitive to treatment comprising of the steps of adding to the regular diet a dietary supplement having an effective amount less than a lethal dose of at least one hemotherapeutic form of at least one of oxalic acid and oxalate in less than a lethal dosage.

15. The method as recited in claim 14 wherein said hemotherapeutic effective form of at least one of oxalic acid and oxalate is selected from the group of oxalic acid in a free acid, ester, lactone, or salt form.

16. The method as recited in claim 14 wherein said at least one of oxalic acid and oxalate is administered at least once a day at a dosage of at least of up to 8 grams for humans and up to 4 grams for warm-blooded animals other than humans.

17. The method as recited in claim 14 further comprising the steps of reducing the intake of oxalic acid or oxalate blockers.

18. The method as recited in claim 17 wherein said blockers are selected from the group of citric acid, ascorbic acid, pyridoxine, calcium, alcohol, resins, clays, and combinations thereof.

19. The method as recited in claim 17 further comprising the steps of reducing the intake of oxalic acid or oxalate blockers selected from at least one of dairy products containing calcium, beverages containing alcohol, ascorbic acid (vitamin C), citric acid, pyridoxine hydrochloride (vitamin B6), foods containing calcium, ascorbic acid or citric acid, red meat, or white meat of fowl containing pyridoxine hydrochloride, and foods, beverages, or nutritional supplements containing oxalic acid or oxalate blockers.

20. A method for treating vascular diseases, plaque, microbial infections, fatty buildup, and calcerous conditions of the vascular system and the brain in patients sensitive to treatment comprising the steps of reducing or eliminating the ingestion or administration of oxalic acid or oxalate blockers, administering or ingesting high dosages in less than a lethal dosage of at least one of oxalic acid and oxalate to raise the blood or urine oxalic or oxalate level above normal, and, after cleansing the blood of diseases and other conditions administering or ingesting a more moderate level of at least one of oxalic acid and oxalate to maintain a normal blood or urine level of oxalic acid or oxalate.

\* \* \* \* \*